(12) United States Patent
Lannutti et al.

(10) Patent No.: US 9,945,824 B2
(45) Date of Patent: Apr. 17, 2018

(54) CORE-SHELL NANOFIBER-BASED SENSORS

(71) Applicant: OHIO STATE INNOVATION FOUNDATION, Columbus, OH (US)

(72) Inventors: John Lannutti, Grove City, OH (US); Ruipeng Xue, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/777,035

(22) PCT Filed: Mar. 17, 2014

(86) PCT No.: PCT/US2014/030559
§ 371 (c)(1),
(2) Date: Sep. 15, 2015

(87) PCT Pub. No.: WO2014/145745
PCT Pub. Date: Sep. 18, 2014

(65) Prior Publication Data
US 2016/0041135 A1 Feb. 11, 2016

Related U.S. Application Data

(60) Provisional application No. 61/788,639, filed on Mar. 15, 2013.

(51) Int. Cl.
*G01N 31/22* (2006.01)
*G01N 21/77* (2006.01)
(Continued)

(52) U.S. Cl.
CPC ....... *G01N 31/225* (2013.01); *G01N 21/6408* (2013.01); *G01N 21/6428* (2013.01);
(Continued)

(58) Field of Classification Search
CPC .... G01N 31/225; G01N 31/223; G01N 31/22; G01N 31/00; G01N 21/77; G01N 21/75
(Continued)

(56) References Cited

U.S. PATENT DOCUMENTS

| 5,047,627 | A | 9/1991 | Yim et al. |
| 2005/0038498 | A1* | 2/2005 | Dubrow ................ A61L 31/14 623/1.15 |
| 2011/0027127 | A1* | 2/2011 | Simpson ............ A61B 5/14532 422/82.01 |

FOREIGN PATENT DOCUMENTS

| WO | 2012061724 A2 | 5/2012 |
| WO | 2012064287 A1 | 5/2012 |

OTHER PUBLICATIONS

Acosta, Miguel A., et al. "Fluorescent microparticles for sensing cell microenvironment oxygen levels within 3D scaffolds." Biomaterials 30.17 (2009): 3068-3074.
(Continued)

*Primary Examiner* — Christine T Mui
(74) *Attorney, Agent, or Firm* — Meunier Carlin & Curfman LLC

(57) ABSTRACT

Nanofiber-based sensors for the rapid detection, identification, and/or quantification of analytes, including gaseous analytes such as oxygen, are provided. The nanofiber-based sensors can comprise core-shell nanofibers. The core-shell nanofibers can comprise (a) a core comprising a first polymer and an sensor dispersed therein; and (b) a shell disposed coaxially around the core, comprising a second polymer.

23 Claims, 37 Drawing Sheets

(51) Int. Cl.
    G01N 21/64    (2006.01)
    G01N 21/78    (2006.01)
    G01N 21/75    (2006.01)
(52) U.S. Cl.
    CPC ........... *G01N 21/77* (2013.01); *G01N 21/783* (2013.01); *G01N 21/6458* (2013.01); *G01N 2021/6432* (2013.01); *G01N 2021/7786* (2013.01)
(58) Field of Classification Search
    USPC ................................ 436/127, 136; 435/27, 4
    See application file for complete search history.

(56)           References Cited

OTHER PUBLICATIONS

Alford, Peter C., et al. "Luminescent metal complexes. Part 5. Luminescence properties of ring-substituted 1, 10-phenanthroline tris-complexes of ruthenium (II)." Journal of the Chemical Society, Perkin Transactions 2 5 (1985): 705-709.
Amao, Yutaka. "Probes and polymers for optical sensing of oxygen." Microchimica Acta 143.1 (2003): 1-12.
Bacon, J. R., and J. N. Demas. "Determination of oxygen concentrations by luminescence quenching of a polymer-immobilized transition-metal complex." Analytical Chemistry 59.23 (1987): 2780-2785.
Bao, Shideng, et al. "Glioma stem cells promote radioresistance by preferential activation of the DNA damage response." nature 444. 7120 (2006): 756-760.
Bedlek-Anslow, Joanne M., et al. "Micro-heterogeneous oxygen response in luminescence sensor films." Langmuir 16.24 (2000): 9137-9141.
Bellail, Anita C., et al. "Microregional extracellular matrix heterogeneity in brain modulates glioma cell invasion." The international journal of biochemistry & cell biology 36.6 (2004): 1046-1069.
Brown, J. Martin, and William R. Wilson. "Exploiting tumour hypoxia in cancer treatment." Nature Reviews Cancer 4.6 (2004): 437-447.
Carmeliet, Peter, et al. "Role of HIF-1α in hypoxia-mediated apoptosis, cell proliferation and tumour angiogenesis." Nature 394. 6692 (1998): 485-490.
Carraway, E. R., et al. "Photophysics and photochemistry of oxygen sensors based on luminescent transition-metal complexes." Analytical chemistry 63.4 (1991): 337-342.
Casciari, Joseph J., Stratis V. Sotirchos, and Robert M. Sutherland. "Variations in tumor cell growth rates and metabolism with oxygen concentration, glucose concentration, and extracellular pH." Journal of cellular physiology 151.2 (1992): 386-394.
Central Brain Tumor Registry of the United States. (2005). Statistical report: primary brain tumors in the United States, 1998-2002. Hinsdale (Illinois): Central Brain Tumor Registry of the United States.
Chen, J., D. F. Farson, and S. I. Rokhlin. "Experimental study of femtosecond laser-stimulated electrical discharges in small gaps and surface modifications." Journal of Applied Physics 105.1 (2009): 013302.
Chen, Guo, and Andre F. Palmer. "Hemoglobin-based oxygen carrier and convection enhanced oxygen transport in a hollow fiber bioreactor." Biotechnology and bioengineering 102.6 (2009): 1603-1612.
Cho, Jung-Ho, Dave F. Farson, and Matt J. Reiter. "Analysis of penetration depth fluctuations in single-mode fibre laser welds." Journal of Physics D: Applied Physics 42.11 (2009): 115501.
Cho, Jung-Ho, et al. "Weld pool flows during initial stages of keyhole formation in laser welding." Journal of Physics D: Applied Physics 42.17 (2009): 175502.
Choi, Hae-Woon, et al. "Ultrashort pulsed laser machining for biomolecule trapping." Journal of the Optical Society of Korea 13.3 (2009): 335-340.
Chu, Cheng-Shane, and Yu-Lung Lo. "Highly sensitive and linear calibration optical fiber oxygen sensor based on Pt (II) complex embedded in sol-gel matrix." Sensors and Actuators B: Chemical 155.1 (2011): 53-57.
Clark Jr, L. C. "Monitor and control of blood and tissue oxygen tensions." ASAIO Journal 2.1 (1956): 41-48.
Csete, Marie. "Oxygen in the cultivation of stem cells." Annals of the New York Academy of Sciences 1049.1 (2005): 1-8.
Curcio, Efrem, Paolo Macchiarini, and Loredana De Bartolo. "Oxygen mass transfer in a human tissue-engineered trachea." Biomaterials 31.19 (2010): 5131-5136.
DeGraff, B. A., and J. N. Demas. "Luminescence-based oxygen sensors." Reviews in Fluorescence 2005. Springer US, 2005. 125-151.
Demas, J. N., and B. A. DeGraff. "Design and applications of highly luminescent transition metal complexes." Analytical Chemistry 63.17 (1991): 829A-837A.
Denko, Nicholas C. "Hypoxia, HIF1 and glucose metabolism in the solid tumour." Nature Reviews Cancer 8.9 (2008): 705-713.
Drilling, Sarah, Jeremy Gaumer, and John Lannutti. "Fabrication of burst pressure competent vascular grafts via electrospinning: effects of microstructure." Journal of biomedical materials research Part A 88.4 (2009): 923-934.
Fathallah-Shaykh, Hassan M. "Darts in the dark cure animal, but not human, brain tumors." Archives of neurology 59.5 (2002): 721-724.
Florescu, Monica, and Andreas Katerkamp. "Optimisation of a polymer membrane used in optical oxygen sensing." Sensors and Actuators B: Chemical 97.1 (2004): 39-44.
Gallego-Perez, Daniel, et al. "High throughput assembly of spatially controlled 3D cell clusters on a micro/nanoplatform." Lab on a chip 10.6 (2010): 775-782.
Gaumer, J., et al. "Source-to-ground distance and the mechanical properties of electrospun fiber." Acta Biomater 5 (2009): 1552-1561.
Gaumer, Jeremy, et al. "Structure-function relationships and source-to-ground distance in electrospun polycaprolactone." Acta Biomaterialia 5.5 (2009): 1552-1561.
Georges, Penelope C., et al. "Matrices with compliance comparable to that of brain tissue select neuronal over glial growth in mixed cortical cultures." Biophysical journal 90.8 (2006): 3012-3018.
Gillanders, R. N., et al. "Thin film dissolved oxygen sensor based on platinum octaethylporphyrin encapsulated in an elastic fluorinated polymer." Analytica chimica acta 502.1 (2004): 1-6.
Grist, Samantha M., Lukas Chrostowski, and Karen C. Cheung. "Optical oxygen sensors for applications in microfluidic cell culture." Sensors 10.10 (2010): 9286-9316.
Gundersen, Sharon I., and Andre F. Palmer. "Hemoglobin-based oxygen carrier enhanced tumor oxygenation: A novel strategy for cancer therapy." Biotechnology progress 24.6 (2008): 1353-1364.
Gundersen, Sharon Irene, Guo Chen, and Andre Francis Palmer. "Mathematical model of NO and O 2 transport in an arteriole facilitated by hemoglobin based O 2 carriers." Biophysical chemistry 143.1 (2009): 1-17.
Guo, Liangqia, et al. "A novel sensor based on the porous plastic probe for determination of dissolved oxygen in seawater." Talanta 74.4 (2008): 1032-1037.
Hanahan, Douglas, and Robert A. Weinberg. "The hallmarks of cancer." cell 100.1 (2000): 57-70.
Harris, Adrian L. "Hypoxia—a key regulatory factor in tumour growth." Nature Reviews Cancer 2.1 (2002): 38-47.
Harris, David Raphael, and Andre Francis Palmer. "Modern crosslinking strategies for synthesizing acellular hemoglobin-based oxygen carriers." Biotechnology progress 24.6 (2008): 1215-1225.
Hartmann, Paul, Marc JP Leiner, and Max E. Lippitsch. "Luminescence quenching behavior of an oxygen sensor based on a Ru (II) complex dissolved in polystyrene." Analytical Chemistry 67.1 (1995): 88-93.
Hartmann, Paul, Marc JP Leiner, and Max E. Lippitsch. "Response characteristics of luminescent oxygen sensors." Sensors and Actuators B: Chemical 29.1 (1995): 251-257.

(56) References Cited

OTHER PUBLICATIONS

Hartmann, Paul, and Wolfgang Trettnak. "Effects of polymer matrices on calibration functions of luminescent oxygen sensors based on porphyrin ketone complexes." Analytical chemistry 68.15 (1996): 2615-2620.

Hartmann, Paul, Marc JP Leiner, and Petra Kohlbacher. "Photobleaching of a ruthenium complex in polymers used for oxygen optodes and its inhibition by singlet oxygen quenchers." Sensors and Actuators B: Chemical 51.1 (1998): 196-202.

He, Huarui, et al. "Selection of silicone polymer matrix for optical gas sensing." Sensors and Actuators B: Chemical 29.1 (1995): 246-250.

Holland, Eric C. "Glioblastoma multiforme: the terminator." Proceedings of the National Academy of Sciences 97.12 (2000): 6242-6244.

Hu, Bin, et al. "The proteoglycan brevican binds to fibronectin after proteolytic cleavage and promotes glioma cell motility." Journal of Biological Chemistry 283.36 (2008): 24848-24859.

Hu, Bin, et al. "Fibulin-3 is uniquely upregulated in malignant gliomas and promotes tumor cell motility and invasion." Molecular Cancer Research 7.11 (2009): 1756-1770.

Huang, Zheng-Ming, et al. "A review on polymer nanofibers by electrospinning and their applications in nanocomposites." Composites science and technology 63.15 (2003): 2223-2253.

Johnson, Jed, Anirban Ghosh, and John Lannutti. "Microstructure-property relationships in a tissue-engineering scaffold." Journal of Applied Polymer Science 104.5 (2007): 2919-2927.

Johnson, Jed, et al. "Electrospun PCL in vitro: a microstructural basis for mechanical property changes." Journal of Biomaterials Science, Polymer Edition 20.4 (2009): 467-481.

Johnson, Jed, et al. "Quantitative analysis of complex glioma cell migration on electrospun polycaprolactone using time-lapse microscopy." Tissue Engineering Part C: Methods 15.4 (2009): 531-540.

Jorge, Pedro AS, et al. "Applications of quantum dots in optical fiber luminescent oxygen sensors." Applied optics 45.16 (2006): 3760-3767.

Jovanov-Milošević, Nataša, Vesna Benjak, and Ivica Kostović. "Transient cellular structures in developing corpus callosum of the human brain." Collegium antropologicum 30.2 (2006): 375-381.

Jung, Shin, et al. "Tracking the invasiveness of human astrocytoma cells by using green fluorescent protein in an organotypical brain slice model." Journal of neurosurgery 94.1 (2001): 80-89.

Katta, P., et al. "Continuous electrospinning of aligned polymer nanofibers onto a wire drum collector." Nano letters 4.11 (2004): 2215-2218.

Kielian, Tammy, Nico van Rooijen, and William F. Hickey. "MCP-1 expression in CNS-1 astrocytoma cells: implications for macrophage infiltration into tumors in vivo." Journal of neuro-oncology 56.1 (2002): 1-12.

Kim, Young Bum, Donghwan Cho, and Won Ho Park. "Electrospinning of poly (dimethyl siloxane) by sol-gel method." Journal of applied polymer science 114.6 (2009): 3870-3874.

Kirkpatrick, J. P.; Brizel, D. M.; Dewhirst, M. W., A mathematical model of tumor oxygen and glucose mass transport and metabolism with complex reaction kinetics. Radial Res 2003, 159, (3), 336-44.

Klimant, Ingo, and Otto S. Wolfbeis. "Oxygen-sensitive luminescent materials based on silicone-soluble ruthenium diimine complexes." Analytical chemistry 67.18 (1995): 3160-3166.

Kneas, Kristi A., et al. "Fluorescence microscopy study of heterogeneity in polymer-supported luminescence-based oxygen sensors." Microscopy and Microanalysis 6.06 (2000): 551-561.

Koren, Klaus, et al. "Strongly phosphorescent iridium (III)-porphyrins-new oxygen indicators with tuneable photophysical properties and functionalities." European journal of inorganic chemistry 2011.10 (2011): 1531-1534.

Kühl, Michael, Lars F. Rickelt, and Roland Thar. "Combined imaging of bacteria and oxygen in biofilms." Applied and environmental microbiology 73.19 (2007): 6289-6295.

Lannutti, J., et al. "Electrospinning for tissue engineering scaffolds." Materials Science and Engineering: C 27.3 (2007): 504-509.

Lee, Jeongwu, et al. "Tumor stem cells derived from glioblastomas cultured in bFGF and EGF more closely mirror the phenotype and genotype of primary tumors than do serum-cultured cell lines." Cancer cell 9.5 (2006): 391-403.

Lee, Carol H., et al. "Vascular wall engineering via femtosecond laser ablation: Scaffolds with self-containing smooth muscle cell populations." Annals of biomedical engineering 39.12 (2011): 3031-3041.

Lee, Sang-Kyung, and Ichiro Okura. "Photoluminescent determination of oxygen using metalloporphyrin-polymer sensing systems." Spectrochimica Acta Part A: Molecular and Biomolecular Spectroscopy 54.1 (1998): 91-100.

Levičar, Nataša, R. K. Nutall, and T. T. Lah. "Proteases in brain tumour progression." Acta neurochirurgica 145.9 (2003): 825-838.

Li, Dan, Yuliang Wang, and Younan Xia. "Electrospinning nanofibers as uniaxially aligned arrays and layer-by-layer stacked films." Advanced Materials 16.4 (2004): 361-366.

Li, Dan, and Younan Xia. "Electrospinning of nanofibers: reinventing the wheel?." Advanced materials 16.14 (2004): 1151-1170.

Lim, Yong C., et al. "Micropillar fabrication on bovine cortical bone by direct-write femtosecond laser ablation." Journal of biomedical optics 14.6 (2009): 064021-064021.

Liu, Yanchun, Xiao Zheng Shu, and Glenn D. Prestwich. "Tumor engineering: orthotopic cancer models in mice using cell-loaded, injectable, cross-linked hyaluronan-derived hydrogels." Tissue engineering 13.5 (2007): 1091-1101.

López-Barneo, José, Ricardo Pardal, and Patricia Ortega-Sáenz. "Cellular mechanism of oxygen sensing." Annual Review of Physiology 63.1 (2001): 259-287.

Louis, David N. "Molecular pathology of malignant gliomas." Annu. Rev. Pathol. Mech. Dis. 1 (2006): 97-117.

Maxwell, Patrick H., Christopher W. Pugh, and Peter J. Ratcliffe. "Activation of the HIF pathway in cancer." Current opinion in genetics & development 11.3 (2001): 293-299.

McDonagh, Colette, Conor S. Burke, and Brian D. MacCraith. "Optical chemical sensors." Chemical reviews 108.2 (2008): 400-422.

McDonagh, Colette, et al. "Nanoparticle strategies for enhancing the sensitivity of fluorescence-based biochips." Nanomedicine 4.6 (2009): 645-656.

Mills, Andrew, and Mark Thomas. "Fluorescence-based Thin Plastic Film Ion-pair Sensors forOxygen." Analyst 122.1 (1997): 63-68.

Milosavljevic, B. H., and J. K. Thomas. "Photochemistry of compounds adsorbed into cellulose. 1. Decay of excited tris (2, 2'-bipyridine) ruthenium (II)." The Journal of Physical Chemistry 87.4 (1983): 616-621.

Nam, Jin, et al. "Improved cellular infiltration in electrospun fiber via engineered porosity." Tissue engineering 13.9 (2007): 2249-2257.

Nam, Jin, et al. "Materials selection and residual solvent retention in biodegradable electrospun fibers." Journal of applied polymer science 107.3 (2008): 1547-1554.

Nam, Jin, et al. "Novel electrospun scaffolds for the molecular analysis of chondrocytes under dynamic compression." Tissue Engineering Part A 15.3 (2008): 513-523.

Nam, Jin, et al. "Modulation of embryonic mesenchymal progenitor cell differentiation via control over pure mechanical modulus in electrospun nanofibers." Acta biomaterialia 7.4 (2011): 1516-1524.

Niehaus, Andrew J., et al. "Effects of orthopedic implants with a polycaprolactone polymer coating containing bone morphogenetic protein-2 on osseointegration in bones of sheep." American journal of veterinary research 70.11 (2009): 1416-1425.

Ohnishi, Takanori, et al. "A novel model of glioma cell invasion using organotypic brain slice culture." Cancer research 58.14 (1998): 2935-2940.

Olabarrieta, Idoia, et al. "Transport properties of chitosan and whey blended with poly (ε-caprolactone) assessed by standard permeability measurements and microcalorimetry." Polymer 42.9 (2001): 4401-4408.

Palfi, S., et al. "Correlation of in vitro infiltration with glioma histological type in organotypic brain slices." British journal of cancer 91.4 (2004): 745-752.

(56) References Cited

OTHER PUBLICATIONS

Palmer, Andre F., Guoyong Sun, and David R. Harris. "The quaternary structure of tetrameric hemoglobin regulates the oxygen affinity of polymerized hemoglobin." Biotechnology progress 25.6 (2009): 1803-1809.

Palmer, Andre F., Guoyong Sun, and David R. Harris. "Tangential flow filtration of hemoglobin." Biotechnology progress 25.1 (2009): 189-199.

Pörtner, Ralf, and Oscar BJ Platas Barradas. "Cultivation of mammalian cells in fixed-bed reactors." Animal Cell Biotechnology. Humana Press, 2007. 353-369.

Powis, Garth, and Lynn Kirkpatrick. "Hypoxia inducible factor-1α as a cancer drug target." Molecular Cancer Therapeutics 3.5 (2004): 647-654.

Pouysségur, Jacques, Frédéric Dayan, and Nathalie M. Mazure. "Hypoxia signalling in cancer and approaches to enforce tumour regression." Nature 441.7092 (2006): 437-443.

Rameez, Shahid, Houssam Alosta, and Andre F. Palmer. "Biocompatible and biodegradable polymersome encapsulated hemoglobin: a potential oxygen carrier." Bioconjugate chemistry 19.5 (2008): 1025-1032.

Rao, Jasti S. "Molecular mechanisms of glioma invasiveness: the role of proteases." Nature Reviews Cancer 3.7 (2003): 489-501.

Revsbech, Niels Peter. "An oxygen microsensor with a guard cathode." Limnology and Oceanography 34.2 (1989): 474-478.

Roskelley, Calvin D., and Mina J. Bissell. "The dominance of the microenvironment in breast and ovarian cancer." In Seminars in cancer biology, vol. 12, No. 2, pp. 97-104. Academic Press, 2002.

Reneker, D. H., et al. "Electrospinning of nanofibers from polymer solutions and melts." Advances in applied mechanics 41 (2007): 43-346.

Ruan, Kai, Gang Song, and Gaoliang Ouyang. "Role of hypoxia in the hallmarks of human cancer." Journal of cellular biochemistry 107.6 (2009): 1053-1062.

Schnell, Eva, et al. "Guidance of glial cell migration and axonal growth on electrospun nanofibers of poly-ϵ-caprolactone and a collagen/poly-ϵ-caprolactone blend." Biomaterials 28.19 (2007): 3012-3025.

Shinar, Ruth, et al. "Structurally integrated organic light emitting device-based sensors for gas phase and dissolved oxygen." Analytica chimica acta 568.1 (2006): 190-199.

Sill, Travis J., and Horst A. von Recum. "Electrospinning: applications in drug delivery and tissue engineering." Biomaterials 29.13 (2008): 1989-2006.

Sim, Hosung, Bin Hu, and Mariano S. Viapiano. "Reduced expression of the hyaluronan and proteoglycan link proteins in malignant gliomas." Journal of Biological Chemistry 284.39 (2009): 26547-26556.

Song, Hong, et al. "Spatial composition of prostate cancer spheroids in mixed and static cultures." Tissue engineering 10.7-8 (2004): 1266-1276.

Stranik, Ondrej, et al. "Optimization of nanoparticle size for plasmonic enhancement of fluorescence." Plasmonics 2.1 (2007): 15-22.

Swanson, Kristin R., E. C. Alvord, and J. D. Murray. "A quantitative model for differential motility of gliomas in grey and white matter." Cell proliferation 33.5 (2000): 317-329.

Swanson, Kristin R. "Quantifying glioma cell growth and invasion in vitro." Mathematical and Computer Modelling 47.5 (2008): 638-648.

Teo, W. E., and S. Ramakrishna. "Electrospun fibre bundle made of aligned nanofibres over two fixed points." Nanotechnology 16.9 (2005): 1878-1884.

Thomas, Peter C., et al. "A noninvasive thin film sensor for monitoring oxygen tension during in vitro cell culture." Analytical chemistry 81.22 (2009): 9239-9246.

Tian, Yanqing, et al. "Influence of matrices on oxygen sensing of three sensing films with chemically conjugated platinum porphyrin probes and preliminary application for monitoring of oxygen consumption of *Escherichia coli (E. coli)*." Sensors and Actuators B: Chemical 150.2 (2010): 579-587.

VanMeter, Timothy E., et al. "The role of matrix metalloproteinase genes in glioma invasion: co-dependent and interactive proteolysis." Journal of neuro-oncology 53.2 (2001): 213-235.

Vaupel, P., et al. "Oxygenation of human tumors: evaluation of tissue oxygen distribution in breast cancers by computerized O2 tension measurements." Cancer research 51.12 (1991): 3316-3322.

Veleva, A. N., et al. "Interactions between endothelial cells and electrospun methacrylic terpolymer fibers for engineered vascular replacements." Journal of Biomedical Materials Research Part A 91.4 (2009): 1131-1139.

Viapiano, Mariano S., Russell T. Matthews, and Susan Hockfield. "A novel membrane-associated glycovariant of BEHAB/brevican is up-regulated during rat brain development and in a rat model of invasive glioma." Journal of Biological Chemistry 278.35 (2003): 33239-33247.

Viapiano, Mariano S., et al. "Novel tumor-specific isoforms of BEHAB/brevican identified in human malignant gliomas." Cancer research 65.15 (2005): 6726-6733.

Viapiano, Mariano S., and Russell T. Matthews. "From barriers to bridges: chondroitin sulfate proteoglycans in neuropathology." Trends in molecular medicine 12.10 (2006): 488-496.

Viapiano, Mariano Sebastian, Susan Hockfield, and Russell Thomas Matthews. "BEHAB/brevican requires ADAMTS-mediated proteolytic cleavage to promote glioma invasion." Journal of neuro-oncology 88.3 (2008): 261-272.

Viapiano, Mariano S., and Sean E. Lawler. "Glioma invasion: mechanisms and therapeutic challenges." CNS Cancer. Humana Press, 2009. 1219-1252.

Voraberger, Hannes S., et al. "Novel oxygen optrode withstanding autoclavation: technical solutions and performance." Sensors and Actuators B: Chemical 74.1 (2001): 179-185.

Wang, Xu-dong, et al. "Optical oxygen sensors move towards colorimetric determination." TrAC Trends in Analytical Chemistry 29.4 (2010): 319-338.

Wang, Xu-dong, et al. "Self-referenced RGB colour imaging of intracellular oxygen." Chemical Science 2.5 (2011): 901-906.

Wu, Changfeng, et al. "Ratiometric Single-Nanoparticle Oxygen Sensors for Biological Imaging." Angewandte Chemie International Edition 48.15 (2009): 2741-2745.

Wu, Wanhua, et al. "Enhanced luminescence oxygen sensing property of Ru (II) bispyridine complexes by ligand modification." Sensors and Actuators B: Chemical 149.2 (2010): 395-406.

Xu, Wenying, et al. "Oxygen sensors based on luminescence quenching: interactions of metal complexes with the polymer supports." Analytical Chemistry 66.23 (1994): 4133-4141.

Xu, Hao, et al. "A real-time ratiometric method for the determination of molecular oxygen inside living cells using sol-gel-based spherical optical nanosensors with applications to rat C6 glioma." Analytical chemistry 73.17 (2001): 4124-4133.

Yu, Jian H., Sergey V. Fridrikh, and Gregory C. Rutledge. "Production of submicrometer diameter fibers by two-fluid electrospinning." Advanced Materials 16.17 (2004): 1562-1566.

Zhang, Ning, Honghai Yan, and Xuejun Wen. "Tissue-engineering approaches for axonal guidance." Brain Research Reviews 49.1 (2005): 48-64.

Chu et al. (2011) Review on recent developments of fluorescent oxygen and carbon dioxide optical fiber sensors. Photonic Sensors 1(3): 234-250.

International Search Report and Written Opinion of the U.S. International Searching Authority from Application No. PCT/US2014/030559, dated Jul. 18, 2014, 9 pages.

\* cited by examiner

CORE-SHELL NANOFIBER-BASED SENSORS

CROSS REFERENCE TO RELATED APPLICATIONS

This application is a U.S. National Phase of PCT/US2014/030559, filed Mar. 17, 2014, which claims the benefit of U.S. Provisional Application No. 61/788,639, filed Mar. 15, 2013, which is hereby incorporated by this reference in its entirety.

STATEMENT REGARDING FEDERALLY SPONSORED RESEARCH OR DEVELOPMENT

This invention was made with government support under Grant No. 1033991 awarded by the National Science Foundation. The government has certain rights in the invention.

FIELD OF THE INVENTION

The present disclosure is generally related to nanofiber-based sensors, as well as methods of using thereof for the rapid detection and/or quantification of analytes.

BACKGROUND OF THE INVENTION

Oxygen is a vital component of biological energy metabolism and plays a central role in many cellular processes. In solid tumors, oxygen distributions are highly heterogeneous and are, in general, at much lower levels of oxygen than normal tissues. At these low concentrations of oxygen, cancer cells can resist both radiotherapy and chemotherapeutics. Real-time continuous monitoring of local oxygen content at the cellular level is important for understanding the biophysical properties of migration and sensitivity to chemotherapeutics as related to the surrounding oxygen content.

Conventional Clark electrodes are currently being used for oxygen sensing (Clark, L. C. et al., Transactions American Society for Artificial Internal Organs 2 (1956) 41-48). However, these sensors consume oxygen during measurements, are invasive, and are difficult to miniaturize to provide localized oxygen information. Such sensors are also limited to single-point measurements and cannot reveal either 2D or 3D oxygen distributions in heterogeneous systems. Recently, optical sensors based on luminescence quenching of oxygen sensitive probes (typically organometallic complexes and metallo porphyrins) have attracted a great deal of attention (Wang, X. et al., Trends Anal. Chem. 29 (2010) 319-338). These molecular probes are usually doped within protective polymer matrix materials, commonly in the forms of films, that serve as a solvent for the luminescent molecules, provide mechanical support, help improve selectivity by preventing penetration of interfering specie, as well as adjust the quenching behavior of the sensor by tailoring the probe-matrix interactions (Florescu, M., et al., Sens. Actuators, B, 97 (2004) 39-44). These probes however, are usually not very compatible with standard cell culture devices and in general have longer response times due to a 2D configuration that limits the surface area susceptible to rapid oxygen diffusion. Biological applications further require that these sensors function in an environment in which oxygen concentrations vary over a relatively small range. Therefore, high sensitivities are considered desirable.

There is a need for oxygen sensors that are sensitive, non-invasive, more easily miniaturized, can be integrated with cell culture devices, lack of oxygen consumption, and freedom from electrical interference.

SUMMARY OF THE DISCLOSURE

Nanofiber-based sensors for the rapid detection, identification, and/or quantification of analytes, including gaseous analytes such as oxygen, are provided. The nanofiber-based sensors can comprise core-shell nanofibers. The nanofiber core can comprise a first polymer having a sensor dispersed therein. The nanofiber shell can comprise a second polymer. The first polymer and the second polymer can be selected in view of a number of factors, including the desired application for the nanofibers, the nature of the sensor dispersed in the first polymer, and the nature of the analyte being detected, identified, and/or quantified by the sensor. The first polymer and the second polymer can be of the same or different composition. In certain embodiments, the first polymer can comprise polydimethylsiloxane (PDMS), polyethersulfone (PES), or combinations thereof, and the second polymer can comprise polycaprolactone (PCL).

The sensor can be any suitable molecule or combination of molecules selected to facilitate radiological, magnetic, optical, and/or electrical measurements or observations used to detect, identify, and/or quantify one or more analytes in a sample in contact with the nanofibers. For example, the sensor can comprise chromophore, a luminophore (e.g., a fluorophore or a phosphor), a probe to facilitate electrochemical detection and/or quantification of an analyte, a probe to facilitate the magnetic detection and/or quantification of an analyte (e.g., by electron paramagnetic resonance spectroscopy or magnetic resonance imaging), or combinations thereof. In certain embodiments, the sensor can be a luminophore (e.g., a fluorescent oxygen sensor).

The nanofiber-based sensors can be used to detect, identify, and/or quantify one or more analytes in a sample. Methods for detecting, identifying, and/or quantifying an analyte in a sample can comprise contacting a sample comprising an analyte with a core-shell nanofiber; and interrogating the sensor in the nanofiber to determine the sensor's response to the analyte. Methods can further involve analyzing the sensor's response to elucidate the presence of an analyte, to identity an analyte, to determine the concentration of an analyte, or combinations thereof. Appropriate devices and/or methods for interrogating the sensor and analyzing the one or more sensor responses can be selected in view of a number of factors, including the nature of the sensor present in the nanofiber core.

The nanofiber-based sensors provided herein can be inexpensive, sensitive, robust, efficient, rapid, and can detect low concentrations of analyte. As such, the nanofibers are well suited for use in numerous sensing applications. For example, the nanofibers can be used for real time analysis of analyte concentration, for example oxygen, in a sample.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

FIG. 5A shows the reversibility of the PES (squares) and PCL (circles) fibers in oxygen or nitrogen saturated water. FIG. 5B are Stern-Volmer plots derived from dissolved oxygen exposure of the PES (square) and PCL (circles) fibers.

FIG. 6A shows PES-PCL core shell fibers as characterized by wide-field merged fluorescent images. FIG. 6B shows the response of the fiber to cyclic $N_2$—$O_2$ gas exposures. FIG. 6C shows a comparison photobleaching of various fibers (PES (solid line), PCL (dotted line) and PES-PCL core-shell (dashed line).

FIG. 7A are representative images of CNS1 glioblastoma cells cultured on polycaprolactone (left) or Ru probe containing PCL (right) nanofiber scaffolds (scale bar=100 μm). FIG. 7B includes bar graphs showing the cell density (cells/mm$^2$; left) and percentage of dead cells (right) for glioblastoma cell lines cultured on nanofiber scaffolds for 48 h.

FIGS. 8A-8B are of the S1 fiber; FIGS. 8C-8D are of the S2 fiber; and FIGS. 8E-8F are of the S3 fiber.

FIGS. 9A-9B are of the S1 fiber; FIGS. 9C-9D are of the S2 fiber; and FIGS. 9E-9F are of the S3 fiber.

FIG. 13A are U251 cells and show similar morphology and stretching over PCL and PDMS(PtOEP)-PCL fibers (bar: 50 μm). FIG. 13B are tumorspheres of U251 cells imaged immediately after deposition on randomly-aligned nanofibers and 48 h later (bars: 100 μm).

FIG. 14A shows analysis of cell viability (number of calcein-positive cells/mm2) and cell death (% of PI-positive cells/total cells per well). Both reveal few significant changes, none of which show a consistent trend. FIG. 14B shows analysis of cell migration (dispersion at 48 h compared to the radius of original tumorsphere). The graph indicates that the migratory behavior is not affected by the presence of the Pt porphyrin probe.

DETAILED DESCRIPTION OF THE DISCLOSURE

Figure 1A:
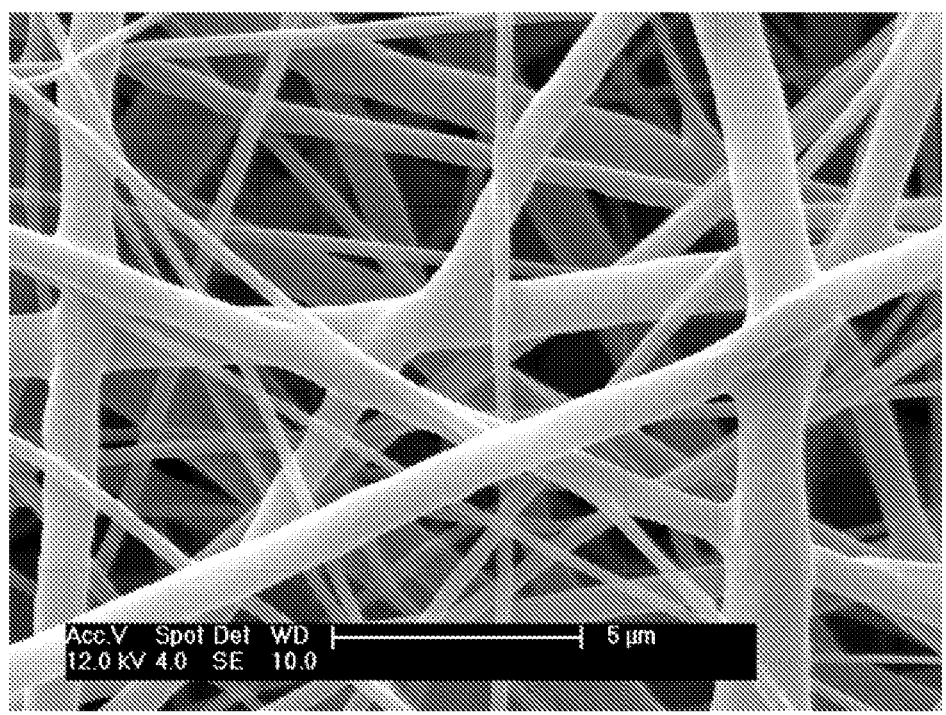
FIGS. 1A-1D are SEM images of a polycaprolactone (PCL) fiber (FIG. 1A), a polyethersulfone (PES) fiber (FIG. 1B), aligned PCL fiber (FIG. 1C), and the fluorescence emitted by random PES fibers in oxygen-free conditions (FIG. 1D). All the fibers contain a Ru oxygen probe.

The present disclosure relates to core-shell nanofibers, methods of making and using the core-shell nanofibers. The present disclosure may be understood more readily by reference to the following detailed description of preferred embodiments of the invention and the Examples included therein and to the Figures and their previous and following description.

As used in the specification and the appended claims, the singular forms "a," "an" and "the" include plural referents unless the context clearly dictates otherwise. Thus, for example, reference to "a nanofiber" includes compositions of two or more such nanofiber, reference to "a oxygen sensor" includes mixtures of two or more such sensors, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Core-Shell Nanofibers

Core-shell nanofibers are disclosed herein. The core-shell nanofibers can comprise a core and a shell. The core can comprise a first polymer and a sensor dispersed therein. The shell can be disposed coaxially around the core, so as to surround the core and form a sheath enclosing the core. The nanofiber shell can comprise a second polymer.

The first polymer and the second polymer can be of the same or different composition. In certain embodiments, the first polymer and the second polymer can be of different compositions. The first polymer and the second polymer can independently be any suitable polymer or mixture of polymers.

Examples of suitable polymers include, but are not limited to, polyolefins; polyethers; polyacrylates; polyesters; polyamides; polyimides; polysulfones; polysiloxanes; polyurethanes; polynitriles; polycarbonates; polyphosphazines; polyvinyl homopolymers and copolymers, such as poly (vinyl chlorides), poly vinyl butyrals), and poly(vinyl alcohols); poly(dienes); fluoropolymers such as polytetrafluoroethylene (PTFE); copolymers thereof, and blends thereof.

In some cases, the first polymer can comprise polydimethylsiloxane (PDMS), polyethersulfone (PES), polystyrene (PS), polyvinyl chloride (PVC), polymethyl(meth)acrylate (PMMA), copolymers thereof, and blends thereof. In certain embodiments, the first polymer can comprise PES, PDMS, or combinations thereof.

In some embodiments, the second polymer can comprise an aliphatic polyester. For example, the second polymer can be selected from the group consisting of poly(lactide), poly(glycolide), poly(lactide-co-glycolide), poly(caprolactone), copolymers thereof, and blends thereof. In certain embodiments, the second polymer can comprise polycaprolactone (PCL).

The molecular weight of the first polymer or the second polymer can be as low as about 1,000 Da; about 3,000 Da; about 6,000 Da; about 10,000 Da; about 12,000 Da; about 15,000 Da; about 20,000 Da; or even as low as about 25,000 Da. The molecular weight can be as high as about 50,000 Da; about 60,000 Da; about 70,000 Da; about 80,000 Da; about 90,000 Da; about 100,000 Da; about 110,000 Da; about 120,000 Da; about 130,000 Da; about 140,000 Da; about 150,000 Da; about 200,000 Da; about 250,000 Da; about 300,000 Da; about 350,000 Da; about 400,000 Da; about 500,000 Da; about 600,000 Da; about 700,000 Da; about 800,000 Da; about 900,000 Da; or even as high as about 1,000,000 Da.

Suitable polymers can be selected in view of a number of factors, including the desired application for the nanofibers, the nature of the sensor dispersed in the first polymer, and the nature of the analyte being detected, identified, and/or quantified by the sensor.

For example, the first polymer and the second polymer can be selected to have a hydrophobicity or hydrophilicity suited for particular applications. In some embodiments, the first polymer can have a hydrophobicity or hydrophilicity effective minimize leaching of the sensor from the nanofiber core when the nonofiber is incubated in a fluid sample. For example, the first polymer can have a hydrophobicity or hydrophilicity selected such that the sensor has a greater affinity for the first polymer than for the fluid sample, such that the sensor does not diffuse from the first polymer to the fluid sample. In some embodiments, the first polymer can have a hydrophobicity or hydrophilicity selected such that the sensor is readily dispersed throughout the first polymer forming the nanofiber core (e.g., such that the sensor is homogenously dispersed throughout the first polymer forming the nanofiber core). In some embodiments, the first polymer and/or the second polymer can be selected to facilitate external monitoring or interrogation of the sensor dispersed in the first polymer. For example, in the case of sensors that exhibit optical responses to the presence of an analyte of interest, the first polymer and/or the second polymer can be selected so as to be at least partially light-transmissive at the wavelengths at which the sensor exhibits a response.

In some embodiments, the first polymer and/or the second polymer can be selected to allow for diffusion of an analyte from the nanofiber exterior to the sensor dispersed in the nanofiber core. By way of example, in some embodiments, the analyte can comprise a gas such as oxygen. The first polymer, the second polymer, or both the first polymer and the second polymer can comprise an oxygen permeable polymer that facilitates diffusion of oxygen from the nanofiber exterior to the sensor dispersed in the nanofiber core.

In some embodiments, the first polymer, the second polymer, or both the first polymer and the second polymer can comprise an oxygen permeable polymer. The term "oxygen permeable" as used herein, refers to a material that can be permeated by oxygen. In certain embodiments, the first polymer, the second polymer, or both the first polymer and the second polymer, when formed into a 1 mil thick film, can have an oxygen transmission rate of greater than 1,000 $cm^3/m^2$ day when measured in accordance with ASTM D 3985-05(2010). In some embodiments, the small diffusion distance associated with the use of a thin (<100 nm) shell surrounding the core allows for rapid diffusion of an analyte, such as oxygen, to the sensor in the nanofiber core, regardless of the bulk polymer oxygen diffusivity.

In some embodiments, the first polymer, the second polymer, or both the first polymer and the second polymer can comprise a polymer having an oxygen diffusivity greater than that of water at room temperature. For example, in certain embodiments, the first polymer, the second polymer, or both the first polymer and the second polymer can comprise a polymer having an oxygen diffusivity of greater than about $2.1 \times 10^5$ $cm^2/s$, greater than about $2.5 \times 10^5$ $cm^2/s$, greater than about $3.0 \times 10^5$ $cm^2/s$, greater than about $3.5 \times 10^5$ $cm^2/s$, greater than about $4.0 \times 10^5$ $cm^2/s$, greater than about $4.5 \times 10^5$ $cm^2/s$, greater than about $5.0 \times 10^5$ $cm^2/s$, greater than about $5.5 \times 10^5$ $cm^2/s$, greater than about $6.0 \times 10^5$ $cm^2/s$, or greater than about $6.5 \times 10^5$ $cm^2/s$. In certain embodiments, the first polymer, the second polymer, or both the first polymer and the second polymer can comprise a polymer having an oxygen diffusivity of about $2.2 \times 10^5$ $cm^2/s$, about $2.4 \times 10^5$ $cm^2/s$, about $2.8 \times 10^5$ $cm^2/s$, about $3.0 \times 10^5$ $cm^2/s$, about $3.3 \times 10^5$ $cm^2/s$, about $3.6 \times 10^5$ $cm^2/s$, about $3.9 \times 10^5$ $cm^2/s$, about $4.1 \times 10^5$ $cm^2/s$, about $4.3 \times 10^5$ $cm^2/s$, or about $4.7 \times 10^5$ $cm^2/s$.

In some embodiments, the first polymer and/or the second polymer can be substantially heat resistant. The term "heat resistance" or "heat resistant," as used herein, refers to the ability of a polymer to withstand a specific thermal condition (such as heat transfer) without significant physical or chemical change. In some embodiments, the first polymer and/or the second polymer are selected such that, after one hour of heating at about 135° C., the nanofiber retains its core-shell structure and its sensory response to a target analyte.

In some embodiments, the second polymer can be selected in view the environment in which the nanofiber will be employed as a sensor. For example, the second polymer can be selected to be compatible with the environment in which the nanofiber will be employed as a sensor (e.g., to be resistant to degradation and/or dissolution in the environment in which the nanofiber will be employed as a sensor). In some embodiments, the second polymer can be selected so as to prevent degradation of the nanofiber in the environment in which the nanofiber will be employed as a sensor. In certain cases, the first polymer can be unstable (e.g., can degrade or dissolve) in the environment in which the nanofiber will be employed as a sensor. In these instances, the second polymer can be stable (e.g., can resist degradation or dissolution) in the environment in which the nanofiber will be employed as a sensor. In this way, the first polymer, along with the dispersed sensor, can be passivated by the second polymer.

In certain embodiments, the first polymer and/or the second polymer can be biocompatible, such that the nanofiber formed from the polymer can be suitable for use in a variety of biological applications. "Biocompatible" and "biologically compatible", as used herein, generally refer to polymers that are, along with any metabolites or degradation products thereof, generally non-toxic to cells and tissues, and which do not cause any significant adverse effects to cells and tissues when cells and tissues are incubated (e.g., cultured) in their presence. In some embodiments, only the second polymer is biocompatible.

As described above, the nanofiber core can comprise a sensor dispersed in the first polymer. The sensor can be any suitable molecule or combination of molecules selected to facilitate radiological, magnetic, optical, and/or electrical measurements or observations used to detect, identify, and/or quantify one or more analytes in a sample. For example, the sensor can comprise chromophore, a luminophore (e.g., a fluorophore or a phosphor), a probe to facilitate electrochemical detection and/or quantification of an analyte, a probe to facilitate the magnetic detection and/or quantification of an analyte (e.g., by electron paramagnetic resonance spectroscopy or magnetic resonance imaging), or combinations thereof, as discussed in more detail below.

The senor can be any suitable molecule or combination of molecules that aid in detection, identification, and/or quantification of an analyte present in a sample contacting the nanofiber. By way of example, the analyte can be a molecule of interest present in a liquid and/or gas sample contacting the nanofiber. In some embodiments, the analyte can be a gas, such as oxygen, carbon monoxide, carbon dioxide, ammonia or other amines, hydrogen sulfide, or sulfur dioxide. The analyte can also be a volatile organic compound (e.g., a volatile amine). The sensor can also be any suitable molecule or combination of molecules that provide for the measurement of one or environmental variables in the region surrounding the nanofiber, such as pH, humidity, and/or temperature. In certain embodiments, the sensor can comprise an oxygen sensor.

In some embodiments, the analyte can be present in a gas sample contacting the nanofiber. The gas sample can be, for example, an environmental sample (e.g., an air quality sample), a process gas, an emission gas (e.g., in an industrial setting or exhaled mammalian breath), or a gaseous fuel stream.

In some embodiments, the analyte can be present in a liquid sample contacting the nanofiber. The liquid sample can be, for example, an aqueous solution, such as a wastewater sample or a liquid biological sample. In some embodiments, the sample can comprise a biological sample (e.g., perspiration, a solution or suspension of cells, an in vitro cell or tissue culture, or tissue in vivo). In some embodiments, the sample can comprise a bodily fluid. "Bodily fluid", as used herein, refers to a fluid composition obtained from or located within a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions, as well as mixtures containing homogenized solid material, such as feces, tissues, and biopsy samples. In some of these embodiments, the analyte can be, for example, a biomarker (i.e., a molecular indicator associated with a particular pathological or physiological state, such as interleukin-6, neuropeptide Y, or cortisol) present in the bodily fluid that can be assayed to identify risk for, diagnosis of, or progression of a pathological or physiological process in a subject.

In some embodiments, the sensor can be selected so as to provide a response in the presence of an analyte that is visible to the naked eye. In some cases, the sensor can exhibit colorimetric and/or fluorometric response in the presence of the analyte of interest. For example, the sensor can include a molecule that becomes colored in the presence of the analyte and/or changes color in the presence of the analyte. In some embodiments, the sensor can be a luminophore. The term "luminophore", as used herein, refers to molecule that manifests luminescence. The sensor can be a luminophore that exhibits changes in its luminescence intensity in the presence of an analyte, a shift of its luminescence in the presence of an analyte, and/or a change the decay time of the luminescence in the presence of an analyte. The luminophore can be a fluorophore or a phosphor. In some embodiments, the luminophore can be a fluorophore. In certain embodiments, the fluorophore can absorb light in the blue region of the spectrum, and fluoresces within the red region of the spectrum. In certain embodiments, the luminophore exhibits an emission peak of from about 570 nm to about 670 nm.

Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru $(dpp)_3$); Ru (II) tris (1,10-phenanthroline) (Ru$(phen)_3$), tris(2,2'-bipyridine)ruthenium (II) chloride hexahydrate (Ru$(bpy)_3$); erythrosine B; fluorescein; eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; rhodamine B; rhodamine 6G; sulfur rhodamine; m-cresol; thymol blue; xylenol blue; cresol red; chlorophenol blue; bromocresol green; bromcresol red; bromothymol blue; 4-nitrophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorecsein; carboxynaphtofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; and dioctadecylcycloxacarbocyanine; or combinations thereof.

In certain embodiments, the first polymer and the luminophore can be selected in combination so as to provide a nanofiber-based sensor that is substantially resistant to photobleaching. In some embodiments, the first polymer and the luminophore can be selected in combination so as to provide a nanofiber-based sensor that exhibits a rate of photobleaching of 0.016%/min or less of the original intensity under continuous illumination.

The sensor can be present in varying amounts within the first polymer. For example, in some embodiments, the weight ratio of the oxygen sensor to the first polymer in the nanofiber core can be at least about 1:1000 (e.g., at least about 1:950; at least about 1:900; at least about 1:850; at least about 1:800; at least about 1:750; at least about 1:700; at least about 1:650; at least about 1:600; at least about 1:550; at least about 1:500; at least about 1:450; at least about 1:400; at least about 1:350; at least about 1:300; at least about 1:250). In some embodiments, the weight ratio of the oxygen sensor to the first polymer in the nanofiber core can be about 1:200 or less (e.g., about 1:250 or less, about 1:300 or less, about 1:350 or less, about 1:400 or less, about 1:450 or less, about 1:500 or less, about 1:550 or less, about 1:600 or less, about 1:650 or less, about 1:700 or less, about 1:750 or less, about 1:800 or less, about 1:850 or less, about 1:900 or less, or about 1:950).

The weight ratio of the oxygen sensor to the first polymer in the nanofiber core can range from any of the minimum values described above to any of the maximum values described above. For example, in some embodiments, the weight ratio of the sensor to the first polymer in the nanofiber core is from about 1:1000 to about 1:200.

If desired for a particular application, a sensor can also be dispersed in the second polymer.

If desired for a particular application, the nanofibers can further comprise a transducer molecule. Transducer molecules include molecules that can react with an analyte of interest present in a liquid and/or gas sample contacting the nanofiber to form or influence the concentration of a surrogate species that can be detected and/or quantified by the sensor in the nanofiber. For example, in some embodiments, the nanofiber can comprise an oxygen sensor and an oxidant (i.e., a transducer molecule) that can reacts with an analyte of interest present in a liquid and/or gas sample contacting the nanofiber. When the oxidant reacts with the analyte of interest, the concentration of oxygen (i.e., a surrogate species) in and/or around the nanofiber changes in proportion to the concentration of the analyte of interest. The oxygen sensor can be used to determine the oxygen concentration in and/or around the nanofiber, and, by extension, to detect and/or quantify the analyte of interest.

If desired for a particular application, the nanofibers can further comprise one or more sensitizers.

Such sensitizers can either up- or down-convert optical wavelengths, for example to permit for excitation of sensors using more advantageous wavelengths of light and/or to transmit sensory responses at energies that can be sensed more easily. Representative upconverting compositions include $NaYF_4$:Yb,Er and $La_2O_3$:Yb,Er and $La_2(MoO_4)_3$:Yb,Er. Representative downconverting compositions may include $Y_{1-x}[(REi)_a(RE_2)_b(RE_n)]_xVO_4$, where $RE_n$ is one or more of the RE downconverting emitters such as $Ce^{3+}$, $Sm^{3+}$, $Eu^{3+}$, $Gd^{3+}$, $Tb^{3+}$, $Er^{3+}$, $Ho^{3+}$, $Tm^{3+}$, $Pr^{3+}$, $Nd^{3+}$, and $Dy^{3+}$. By incorporating sensitizers, core-shell nanofibers can be prepared that operate in tissue-penetrating wavelengths in the "near-infrared therapeutic window" (e.g., from 650 to 1400 nm, bounded roughly by the absorbance of melanin and hemoglobin at shorter wavelengths and the absorbance of water at long wavelengths).

Figure 16:
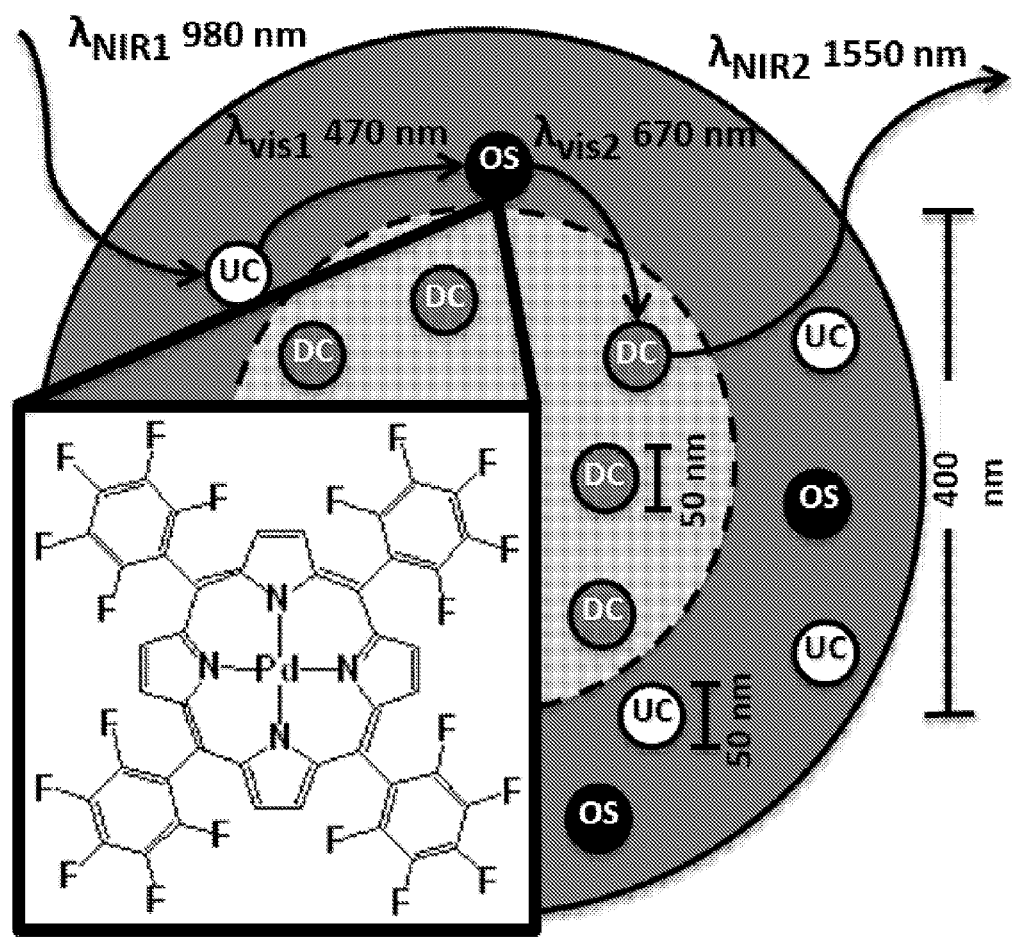
FIG. 16 is a schematic illustration of a core-shell nanofiber containing sensitizers.

By way of example, sensitizers can be incorporated into core-shell nanofibers to prepare nanofiber-based sensors for use in biological applications (e.g., in vitro and in vivo). An example core-shell nanofiber comprising sensitizers is schematically illustrated in FIG. 16. The 'shell' contains both upconverting (UC) nanoparticles and oxygen-sensing luminophores, while the 'core' contains downconversion (DC) nanoparticles. Due to its ability to easily penetrate soft tissues and cell layers with minimal damage, NIR light of wavelength $\lambda_{NIR1}$ (typically 980 nm) can be used as the excitation source for UC nanoparticles located within the shell of the fiber. These will subsequently emit visible light of wavelength $\lambda_{vis1}$. This wavelength will match the excitation peak (e.g., 470 nm) of oxygen-sensing molecules in the shell. The oxygen sensing molecules will emit a second visible wavelength $\lambda_{vis2}$ (typically 670 nm) absorbed by DC nanoparticles located within the fiber core. These downconverters will then emit $\lambda_{NIR2}$ (1300-1550 nm) that can penetrate through tissue or cells. The net output in the NIR range can be measured externally using an InGaAs NIR spectrometer to determine oxygen concentration in real time. This combination of photonic up- and down-converting particles and oxygen-sensing molecules will provide electrospun fibers with unique sensing-reporting capabilities. Such fibers could serve as a scaffold for tissues or cells that then allows for in vitro monitoring of oxygen concentration without placing the sensing molecules in direct contact with cells or tissue.

The nanofibers are in the form of continuous filaments or discrete elongated pieces of material, that typically have average diameters, as determined by scanning electron microscopy, of less than or equal to about 1000 nanometers. The dimensions of the nanofiber can be selected in view of a number of factors, including the desired application for the nanofiber-based sensors, the nature of the sensor dispersed in the first polymer, and the nature of the analyte being detected, identified, and/or quantified by the sensor, and the identity of the first polymer and the second polymer.

The nanofiber can be any suitable diameter between about 100 nm to about 1000 nm. For example, the diameter of the nanofiber can be between about 100 nm to about 1000 nm; about 200 nm to about 900 nm; about 300 nm to about 700 nm; about 400 nm to about 600 nm. The diameter of the nanofiber can be greater than about 100 nm; greater than about 200 nm; greater than about 30 nm; greater than about 400 nm; greater than about 500 nm; greater than about 600 nm; greater than about 700 nm; greater than about 800 nm; or greater than about 900 nm. For example, the diameter of the nanofiber can be between about 400 nm to about 600 nm; about 640 nm to about 1280 nm; about 317 nm to about 707 nm; about 270 nm to about 532 nm; about 378 nm to about 762 nm. The average diameter of the nanofiber can be between about 401 nm to about 960 nm. For example, the average diameter of the nanofiber can be about 401 nm±131 nm; about 512 nm±195 nm; about 570 nm±192 nm; about 960 nm±320 nm.

The diameter of the core in the nanofiber can be between about 100 nm to about 999 nm. For example, the diameter of the core in the nanofiber can be between about 100 nm to about 999 nm; about 200 nm to about 900 nm; about 300 nm to about 700 nm; about 400 nm to about 600 nm. The diameter of the core in the nanofiber can be greater than about 100 nm; greater than about 200 nm; greater than about 30 nm; greater than about 400 nm; greater than about 500 nm; greater than about 600 nm; greater than about 700 nm; greater than about 800 nm; or greater than about 900 nm. For example, the diameter of the core in the nanofiber can be between about 400 nm to about 600 nm; about 640 nm to about 1280 nm; about 317 nm to about 707 nm; about 270 nm to about 532 nm; about 378 nm to about 762 nm. The average diameter of the core in the nanofiber can be between about 401 nm to about 960 nm. For example, the average diameter of the core in the nanofiber can be about 401 nm±131 nm; about 512 nm±195 nm; about 570 nm±192 nm; about 960 nm±320 nm.

The diameter of the shell in the nanofiber can be between about 100 nm to about 999 nm. For example, the diameter of the shell in the nanofiber can be between about 100 nm to about 999 nm; about 200 nm to about 900 nm; about 300 nm to about 700 nm; about 400 nm to about 600 nm. The diameter of the shell in the nanofiber can be greater than about 100 nm; greater than about 200 nm; greater than about 30 nm; greater than about 400 nm; greater than about 500 nm; greater than about 600 nm; greater than about 700 nm; greater than about 800 nm; or greater than about 900 nm. For example, the diameter of the shell in the nanofiber can be between about 400 nm to about 600 nm; about 640 nm to about 1280 nm; about 317 nm to about 707 nm; about 270 nm to about 532 nm; about 378 nm to about 762 nm. The average diameter of the shell in the nanofiber can be between about 401 nm to about 960 nm. For example, the average diameter of the shell in the nanofiber can be about 401 nm±131 nm; about 512 nm±195 nm; about 570 nm±192 nm; about 960 nm±320 nm.

The core-shell nanofibers described herein can be fabricated using any suitable method for the production of core-shell nanofibers known in the art. For example, in some embodiments, electrospinning techniques can be used to generate the core-shell nanofibers. Electrospinning uses an electrical charge to draw fine fibers (e.g., nanofibers) from a liquid (e.g., a polymer solution or melt). Typically, electrospinning techniques make use of a high-voltage power supply, a spinneret (e.g., a hypodermic needle), and an electrically-conductive collector (e.g., aluminum foil). During the electrospinning process, an electrospinning liquid (e.g., a melt or solution of a polymer that will be used to form the nanofiber) is loaded into a syringe and is then fed at a specific rate set by a syringe pump. In some cases, a well-controlled environment (e.g., humidity, temperature, and atmosphere) can be used to achieve a smooth, reproducible operation of electrospinning The nanofiber core may be produced by electrospinning a solution or melt that comprises a sensor, the first polymer, and optionally a suitable solvent. The method may include combining the sensor with a solvent to form a sensor solution. A variety of solvents may be used. For example, the solvent and/or solvent system can include, but are not limited to, water, acetic acid, acetone, acetonitrile, alcohol (e.g., methanol, ethanol, propanol, isopropanol, butanol, 1,1,1,3,3,3-hexafluoro-2-propanol, and the like), dimethyl formamide, alkyl acetate (e.g., ethyl acetate, propyl acetate, butyl acetate, etc.), polyethylene glycols, propylene glycol, butylene glycol, ethoxydiglycol, hexylene glycol, methyl ethyl ketone, alkanes, tetrahydrofuran, chloroform, dimethyl acetamide, dimethyl sulfoxide, acetonitrile, acetic acid, formic acid, or mixtures thereof. The first polymer can then be combined with the sensor solution to form an electrospinning solution. The uniformly mixed electrospinning solution can then be electrospun according to procedures know in the art.

The core-shell nanofibers may be prepared by simultaneous co-axial electrospinning of a core electrospinning solution (e.g., comprising a sensor, the first polymer, and optionally a suitable solvent) and a shell electrospinning solution (e.g., comprising the second polymer and optionally a suitable solvent) through two concentric blunt needles. For example, a core polymer solution may be prepared, as described above, by combining the sensor with a solvent to form a sensor solution. The first polymer may be combined with the sensor solution to form a first electrospinning ('core polymer') solution. A shell polymer solution may be prepared by combining the second polymer with a solvent to form a second electrospinning ('shell polymer') solution. The first and second electrospinning solutions are then simultaneously, co-axially electrospun through two concentric blunt needles. In one embodiment, the applied voltage can be about 25 kV.

The relative flow rate of the first and second elestrospinning polymer solutions during electrospinning is a factor in controlling the formation of core-shell nanofiber and final sensing properties of the core-shell fibers. In one embodiment, the relative core and shell flow rates may be fixed at a ratio of 1:4.

Methods of Use

Also provided are methods for detecting, identifying, and/or quantifying an analyte in a sample. The methods comprise contacting the sample comprising an analyte with a core-shell nanofiber described herein; and interrogating the sensor in the nanofiber to determine the sensor's responses to the analyte. Methods can further involve analyzing the sensor's response to elucidate the presence of an analyte, to identity an analyte, to determine the concentration of an analyte, or combinations thereof. Appropriate devices and/or methods for interrogating the sensor and analyzing the one or more sensor responses can be selected in view of a number of factors, including the nature of the sensor present in the nanofiber core.

By way of example, in some embodiments, the sensor can be a molecule that exhibits a spectroscopically observable change (e.g., a colorimetric and/or fluorometric response) in the presence of the analyte of interest. In some embodiments, the sensor can be a luminophore. The spectroscopically observable change can be a change in the absorbance of the sensor (i.e., color), a change in the fluorescence of the sensor, a change in the phosphorescence of the sensor, or a combination thereof.

In these cases, methods for detecting, identifying, and/or quantifying an analyte in a sample can comprise (a) contacting the sample comprising an analyte with a core-shell nanofiber described herein; and (b) evaluating the optical properties of the sensor to elucidate the presence of an analyte, to identity an analyte, to determine the concentration of an analyte, or combinations thereof. In certain embodiments, the sensor can comprise an oxygen sensor (e.g., a fluorescent oxygen sensor), and the methods can comprise evaluating the optical properties of the oxygen sensor to determine the oxygen content of a same.

In some cases, one or more spectroscopically observable changes in a sensor are qualitatively observed to detect the presence of an analyte in a sample. For example, the absorbance of the sensor (i.e., color) of the fluorescence of the sensor (under irradiation by, for example a UV blacklight) can be observed by the naked eye to qualitatively assess the presence of an analyte in a sample. In other embodiments, one or more spectroscopically observable changes in a sensor are measured as part of an assay to quantify the amount of analyte in a sample.

In certain embodiments, the core-shell nanofibers are use used in a fluorescence-based assay for the detection and/or quantification of an analyte. Fluorescence assays involve the observation and/or measurement of changes in the fluorescence of a sensor in the nanofiber (e.g., a fluorescent oxygen sensor present in the nanofiber core) upon contact with an analyte. The change may take one or more of several forms, including a change in emission spectra, a change in the intensity of the fluorescence (i.e., fluorescence quantum yield), and a change in the fluorescence lifetime. These changes may be either in the positive or negative direction and may be of a range of magnitudes, which preferably will be detectable as described below.

The emission spectra of a fluorophore sensor can be measured using a spectrofluorometer. The spectrofluorometer uses a high intensity light source with a particular wavelength (or interval of wavelengths) to excite the fluorophore. The spectrofluorometer then measures the intensity of light emitted by the fluorophore at a range of different wavelengths, called an emission spectra. Changes in the maximum emission wavelength or the shape of the emission spectra that are caused by an analyte of interest in a sample may be used to determine the presence or concentration of the analyte of interest in the sample.

In embodiments where an analyte is detected or quantified by measuring the change in the maximum emission wavelength of the sensor, the sensor can be designed to exhibit a large change in maximum emission wavelength upon exposure to the analyte of interest. In some embodiments, the maximum emission wavelength of the sensor shifts by more than 50 nm, more preferably by more than 75 nm, most preferably by more than 100 nm upon exposure to the analyte of interest.

Changes in the maximum emission wavelength can also be observed with the naked eye, for example with the use of a handheld blacklight, to qualitatively determine the presence of the analyte of interest in a sample.

The fluorescence quantum yield of a sensor can be measured using methods known in the art. See, for example, Lakowicz, J. R. "Principles of Fluorescence Spectroscopy", $2^{nd}$ Ed., Plenum Press, New York, 1999. Generally, the fluorescence quantum yield of the sensor is obtained by comparison of the integrated area of the corrected emission spectrum of the sensor with that of a reference solution.

A change in the fluorescence quantum yield of the sensor upon exposure to an analyte of interest may be used as the basis for detecting the presence of the analyte of interest in a sample, and may optionally be used to determine the concentration of the analyte of interest in a sample.

In some embodiments, the sensor will preferably be selected so as to exhibit a large change in fluorescence quantum yield upon exposure to the analyte of interest. In some embodiments, exposure of the sensor to the analyte of interest results in at least a 10% reduction in the fluorescence quantum yield of the sensor (e.g., at least a 25% reduction in the fluorescence quantum yield of the sensor, at least a 50% reduction in the fluorescence quantum yield of the sensor, at least a 75% reduction in the fluorescence quantum yield of the sensor, or at least a 90% reduction in the fluorescence quantum yield of the sensor).

In other embodiments, exposure of the sensor to the analyte of interest can result in at least a 25% increase in the fluorescence quantum yield of the sensor (e.g., at least a 50% increase in the fluorescence quantum yield of the sensor, at least a 75% increase in the fluorescence quantum yield of the sensor, at least a 100% increase in the fluorescence quantum yield of the sensor, at least a 500% increase in the fluorescence quantum yield of the sensor, or at least a 1000% increase in the fluorescence quantum yield of the sensor).

The fluorescence lifetime of a sensor can also be measured using methods known in the art. Changes in the fluorescence lifetime of a sensor upon exposure to an analute can also be used to determine the presence or concentration of an analyte in the sample.

In one embodiment, a core-shell nanofiber comprising a fluorescent oxygen sensor immobilized in the core of the nanofiber is provided. Specifically, the fluorescent oxygen sensor can be a ruthenium (II) complex. The ruthenium (II) complex can exhibit a reduction in fluorescence quantum yield (i.e., quenching) and a change in fluorescence lifetime when contacted with oxygen. These core-shell nanofibers can be used to quantify and/or monitor oxygen concentration. In certain embodiments, methods can involve monitoring the fluorescence emission intensity of the ruthenium (II) complex. In certain embodiments, methods can involve monitoring the fluorescence lifetime of the ruthenium (II) complex. The change in the emission intensity and/or lifetime of the ruthenium (II) complex can be correlated to the oxygen partial pressure. Through comparison to standard curves, measurements of emission intensity and/or fluorescence lifetime of the ruthenium (II) complex can be used to determine (or monitor) the partial pressure of oxygen in a sample.

The nanofibers described herein can be inexpensive, sensitive, robust, efficient, rapid, and can detect low concentrations of analyte. As such, the nanofibers are well suited for use in numerous sensing applications. For example, the nanofibers can be used for real time analysis of analyte concentration, for example oxygen, in a sample.

In some embodiments, the nanofiber-based sensor can exhibit a fast response time to a change in analyte within less than about 10 seconds. Response time can be controlled by choice of fiber diameter. For example, in the case of certain oxygen-sensing nanofibers, 810 nm fiber diameters can exhibit a response time of 0.80±0.16 s, 460 nm fiber diameters can exhibit a response time 0.36±0.06 s. Linear extrapolation leads to the conclusion that a 200 nm diameter fiber would exhibit a response time of 0.1-0.2 s, and 100 nm fiber would exhibit a response time of 0.05-0.1 s.

In some embodiments, the nanofiber-based sensor can exhibit a response time of less than about 0.5 seconds. In one particular embodiment, the nanofiber-based sensor comprises an oxygen sensing nanofiber that exhibits a response time to a change in oxygen content within less than about 10 seconds, for example, less than about 0.5 seconds. In certain cases, the nanofibers can be used to measure/monitor in real time, the oxygen content level of a sample.

The core-shell nanofibers can optionally be fashioned into articles that can be used to detect, identify, and/or quantify an analyte of interest. For example, the core-shell nanofibers can be incorporated and/or formed into a fabric (e.g., a non-woven fabric or a woven fabric) that can be used as component in wound dressings. Problematically, current wound assessment and therapeutic methods require the removal of dressings, resulting in further disruptions to the surgical site or wound bed that can lead to discomfort, compromised healing and complications. To address these needs, a transparent wound dressing can be fashioned using the core-shell nanofibers described herein. When placed in contact with a wound, the core-shell nanofibers in the wound dressing can be interrogated to provide real-time measurements of analytes within the wound. By monitoring analytes associated with wound healing and infection, the core-shell nanofibers in the wound dressing can be interrogated to provide real-time information regarding the status of wound healing. For example, using oxygen-sensing core-shell nanofibers, wound dressings can be constructed that provide real-time maps of tissue oxygenation and other parameters across entire wounds, surgical beds or burn sites for direct, continuous monitoring of tissue health throughout the healing process.

In some examples, core-shell nanofibers described herein comprising oxygen sensors can be integrated into or used in conjunction with cell culture plates or bioreactors to provide critical information about the local oxygen content of adherent cells or tissue. As such, the core-shell nanofibers can be used, for example, in cancer cell research and engineered tissue growth.

In some examples, core-shell nanofibers described herein comprising oxygen sensors can be used in wastewater treatment applications. For example, core-shell nanofibers described herein comprising oxygen sensors can be used to measure the biochemical oxygen demand (BOD) exerted by bacteria in treated or partially treated wastewater. As such, the core-shell nanofibers can be used, for example, to assess the degree of organic pollution of water. In some examples, core-shell nanofibers described herein comprising oxygen sensors can be used to monitor the efficacy of wastewater treatment operations in real-time. Platform fabrication can involve the use of multiple oxygen-sensing fluorophores allowing highly accurate determination of both 'low' and 'high' dissolved oxygen contents during biochemical oxygen consumption. Core-shell technologies can protect and preserve the sensing element to allow for sensing of the envisioned disposable element out to 30 days or longer.

In this context, electrospinning as a manufacturing process has distinct benefits as it can fabricate 100×100 cm sheets yielding up to 1,000 individual 1×1 cm sensor elements after only a few minutes of deposition. This can allow for rapid, low-cost fabrication of individual sensor components, as well as the overall nanofiber platform upon which these sensors will be positioned. Electrospinning can also be used to easily fabricate nanofibers containing a wide variety of sensors. Different sensors can easily be added into the large sheets thus enabling 'multiplex' sensing of specific chemical, thermal or biological influences. For example, quantum dots can be incorporated into electrospun fiber specifically to provide temperature sensing.

Multilayer fabrication provides another advantage for wastewater treatments. Multilayer non-woven or woven fiber constructs can be made to contain pores, so as to produce highly efficient filters for both bacteria and dissolved solids in wastewater, thus preventing the migration of bacteria and dissolved solids through isolated nanofiber layers. Such highly efficient barriers to bacterial migration can be used to prevent bacterial proliferation inside the plane of the nanofiber sensor array thus ensuring that bacterial overlayers do not form inside the sensing chamber where they could complicate the analysis. Thus, effective removal of even 300 nm *Mycoplasma* bacteria can be achieved without decreasing $O_2$ diffusion. *Escherichia coli*, a bacterium of average size, ranges from 1.1-1.5 µm wide to 2.0-6.0 µm long; bacteria will not be able to pass through the underlying filter base. This allows both the wastewater and the nanofiber sensing chamber to retain identical oxygen levels in spite of the presence of multiple intervening nanofiber layers.

Multilayer fabrication also enables the incorporation of time- and resource-saving steps that allow fewer materials and less preparation/training for a successful BOD test. Nitrification inhibitors can be used to avoid oxidation of nitrogenous compounds that lead to inaccurate values of BOD. Such inhibitors (such as 2-chloro-6-(trichloro methyl) pyridine (TCMP)) can be easily spun into the nanofiber in the platform as a specific layer that elutes the inhibitor within the test chamber, making additions by the operator unnecessary. Finally, multilayer fabrication can also allow for the incorporation of bacterial 'seeds' into the platform. This creates opportunities for pre-seeding the platform with desired bacteria to standardize BOD response. This provides another method of eliminating the need for operator intervention.

In some embodiments, particularly for use in wastewater treatment applications, the core shell nanofiber can comprise a core comprising a polyurethane and an oxygen sensor dispersed therein; and (b) a shell comprising polyethylene (e.g., ultrahigh molecular weight polyethylene) disposed coaxially around the core. Electrospun polyurethane as a fluorophore-carrying 'core' can withstand exposure to room temperature environments for periods of up to 30 days without loss of integrity or fluorophore. The use of ultrahigh molecular weight polyethylene (UHMWPE) as a protective 'shell' for the polyurethane 'core' to take advantage of polyethylene's well known resistance to the wastewater environment. UHMWPE powder (GUR 415 Hoechst; mw=$6.3 \times 10^6$ kg/kmol) can be dissolved in a mixture of p-xylene and cyclohexanone and spun as the 'shell' using procedures developed previously.

In some examples, core-shell nanofibers described herein comprising sensors for $H_2S$ and/or $SO_2$ can be used to detect and/or quantify the amount of $H_2S$ and/or $SO_2$ in water samples taken from wells, municipal water sources, and natural water sources, for example to ensure water quality and safety. Core-shell nanofibers described herein comprising sensors for $H_2S$ and/or $SO_2$ can also be used to detect and/or quantify $H_2S$ and/or $SO_2$ in liquid effluents and gas emissions industrial settings, including paper and pulp mills, asphalt plants, and sewage treatment facilities. Core-shell nanofibers described herein comprising sensors for $H_2S$ and/or $SO_2$ can also be used to detect and/or quantify $H_2S$ and/or $SO_2$ in gaseous fuel streams. Examples of gaseous fuel streams include biogas, frac gas, gasified biomass, gasified coal/bitumen, gases from natural gas and oil wells, gases from tar sands, landfill gases, syngas, flare gas, and gases from agricultural and livestock operations.

Figure 15:
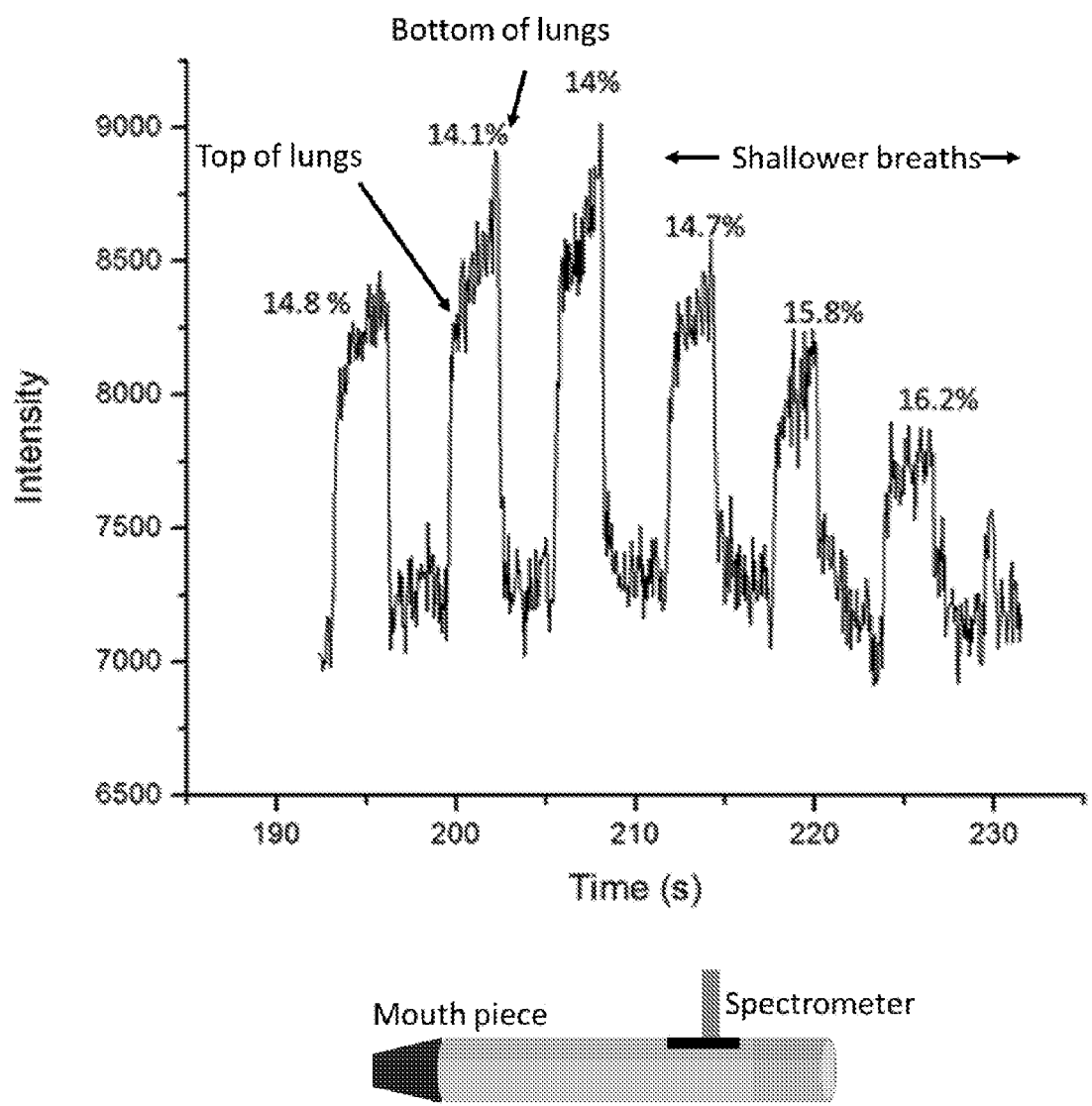
FIG. 15 is a plot of the fluorescence intensity of oxygen-sensing core-shell nanofibers exposed to human breath as a function of time. Core-shell nanofibers were placed in a tube attached to a mouthpiece. The fluorescence of the nanofibers was monitored as a human subject inhaled and exhaled over a period of 3 minutes.

The core-shell nanofibers can also be used as sensors for analytes in exhaled mammalian breath. For example, core-shell nanofibers comprising oxygen sensors can be used to measure the oxygen/carbon dioxide ratio in real time of exhaled mammalian breath in real time. Such systems can be used, for example, to monitor the performance of athletes or pilots. By way of example, FIG. 15 is a plot of the fluorescence intensity of oxygen-sensing core-shell nanofibers exposed to human breath as a function of time. Core-shell nanofibers were placed in a tube attached to a mouthpiece. The fluorescence of the nanofibers was monitored as a human subject inhaled and exhaled over a period of 3 minutes. As shown in FIG. 15, these sensors can monitor the net oxygen content of exhaled breath in real time. In a similar manner, a carbon dioxide sensor, such as m-cresol, can be incorporated into the core-shell nanofibers to rapidly, accurately and continuously determine the $CO_2$ content of exhaled breath. Using these sensors in common, the ratio of oxygen to carbon dioxide in human breath (which is known to directly correspond to overall levels of fatigue) can be monitored in real time.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Rapid Response Oxygen-sensing Nanofibers

A fiber-based platform with an oxygen sensitive ruthenium compound was combined to develop a nanofiber based optical oxygen sensor. The sensor is capable of responding rapidly to changes in the oxygen content of surrounding gaseous/aqueous environment. This nanofiber could easily be applied to a variety of matrices and probes and can be readily integrated to tissue culture plates or bioreactors, providing an alternative to the standard optical oxygen sensor family.

Materials and Methods

Polycaprolactone ($M_n$=70,000-90,000) and dichloromethane were purchased from Sigma-Aldrich (St. Louis, Mo., USA) and polyethersulfone was obtained from Goodfellow (Huntingdon, England). Tris(4,7-diphenyl-1,10-phenanthroline) ruthenium(II) dichloride was acquired from Alfa Aesar (Ward Hill, Mass., USA). 1,1,1,3,3,3-hexafluoro-2-propanol (HFP) was obtained from Oakwood Products Inc. (West Columbia, S.C., USA).

Preparation of Oxygen Sensitive Fibers

The oxygen sensitive probe, $[Ru(dpp)_3]^{2+}$, was dissolved into HFP; the resulting orange-colored solution was stirred at room temperature for 20 min to fully dissolve the probe. The electrospinning solution was prepared by continuously stirring either 5 wt. % PCL or 8 wt. % PES polymer pellets into the HFP solution at 55° C. until the polymer completely dissolve. The weight ratio of the oxygen probe and carrier polymer was held constant at 1:1000. After cooling to room temperature, the uniformly mixed solution was electrospun. The large diameter PCL fibers were fabricated by using dichloromethane (DCM) as the solvent. The typical sample thickness (approximately 100 µm) for sensing applications was held constant by fixing the deposition time at 400 s. The as-spun fiber sheet was then placed in a vacuum overnight to remove residual solvent.

A "shell" containing no luminophore was added to these oxygen sensitive fibers by simultaneous co-axial electrospinning of two polymer solutions through two concentric blunt needles. 5 wt. % Ru probe-containing PES solution (Ru:PES=1:1000 ratio by weight) was electrospun as the "core" while 5 wt. % PCL solution was electrospun as the "shell." The flow rates for PES and PCL solutions were both 4 mL/h and the applied voltage 25 kV. For comparison, conventional film-based sensors were also prepared using the same polymer and probe solutions by casting onto a glass slide. All samples were stored within completely dark containers prior to characterization or testing.

Microscopy and image analysis: Scanning electron microscopy (SEM; XL30 ESEM, FEI Company, Hillsboro, Oreg., USA) was used to examine the morphology of the probe containing fibers following the application of a 100 angstrom-thick gold coating by a sputter coater (Pelco, Clovis, Calif., USA). The luminescent properties of the fibers were studied by capturing fluorescent images on a fluorescence microscope (Eclipse, Nikon Inc. Melville, N.Y., USA) with a filter set for red fluorescence (EX: 530-560 nm, DM: 570 nm, BA: 590-650 nm). The exposure time for each image was 400 ms and the fluorescence intensity of the red channel in the images was measured in randomly selected areas using NIH ImageJ.

Optical spectroscopy: The fluorescence spectrum measurements of the fibers and the continuous monitoring of the emission peak were conducted by a fluorescence spectrometer (JAZ, Ocean Optics Inc., Dunedin, Fla., USA). Blue LED light at 470 nm used as the excitation wavelength was guided through 600 µm VIS-NIR fibers. The optic fiber probe was positioned perpendicular to the electrospun mats and the collected signal delivered to the spectrometer to either display the resulting spectrum or to conduct time-based measurements at a particular wavelength.

Measurements of gaseous oxygen: Sensing of the nanofiber was first examined by monitoring atmospheric oxygen. Electrospun fiber mats were glued to the inner wall of fixed cuvettes with the probe of the spectrometer oriented perpendicularly to the sample. A glass tube connected to a gas mixer (Omega Engineering, USA) was inserted and placed at the bottom of the cuvette. The oxygen gas concentration was controlled by adjusting the relative flow rates of oxygen and nitrogen gas. As oxygen flow rates increased from 0 to 100% at 10% increments the emission spectra was recorded. To examine reversibility and response time, the cuvette was filled with pure oxygen and was then alternated with pure nitrogen at 20 s intervals. Gas flow rates of 1450 cc/min were used to rapidly alter the atmosphere around the sample and minimize measurement error. The intensity of the emission peak was measured continuously as a function of time.

Measurements of dissolved oxygen: Oxygen sensitivity tests of the fibers in aqueous solutions were then conducted in a transparent chamber containing a 1×1 cm sample of oxygen sensing fiber. The desired oxygen concentrations were controlled by sparging defined ratios of mixed gases into the water within the chamber. Oxygen and nitrogen gases were merged to a tube inserted in the chamber and flow rates maintained by a proportioner for 30 min prior to measurement to ensure equilibrium. Real-time dissolved oxygen concentration was monitored using a commercial oxygen meter (Hach Company, Loveland, Colo., USA) to provide calibration. The position of the gas outlet was ~2 cm away from both the oxygen meter probe and the sample to reduce interference effects potentially generated by the gas flow. The change in fluorescence intensity was monitored by the fluorescence spectrometer at the emission peak. For tests of reversibility, water was bubbled and saturated with either pure nitrogen or pure oxygen. The fluorescence intensity change was determined by measuring the images taken by the fluorescence microscope.

Cell culture experiments: The cytotoxicity of the oxygen sensing fibers to cells was investigated. Cell culture experiments were performed with glioblastoma cell lines U251MG and CNS1. U251MG cells were cultured in Dulbecco's modified Eagle's medium (containing 4.5 g/L glucose) while CNS1 cells were cultured in RPMI-1640 medium (containing 2 mM L-glutamine). In both cases, the medium was supplemented with 10% fetal bovine serum, 50 IU/mL penicillin and 50 µg/mL streptomycin. Cells were gently dissociated when they reached 80% confluence and seeded at an average density of 10,000 cells/well in 24-well plates with PCL alone or probe-containing PCL (Ru-PCL) nanofiber-coated plates. Cells were cultured for 48 h and subsequently stained with Calcein-AM (1 µg/mL, Invitrogen) and propidium iodide (0.5 µg/mL, Invitrogen), following standard protocols. The cells were analyzed by fluorescence microscopy to identify live (calcein-positive, green fluorescence) and dead (PI-positive, red fluorescence) cells. Image analysis and quantification were performed using ImageJ (v.1.47) software.

Figure 1B:
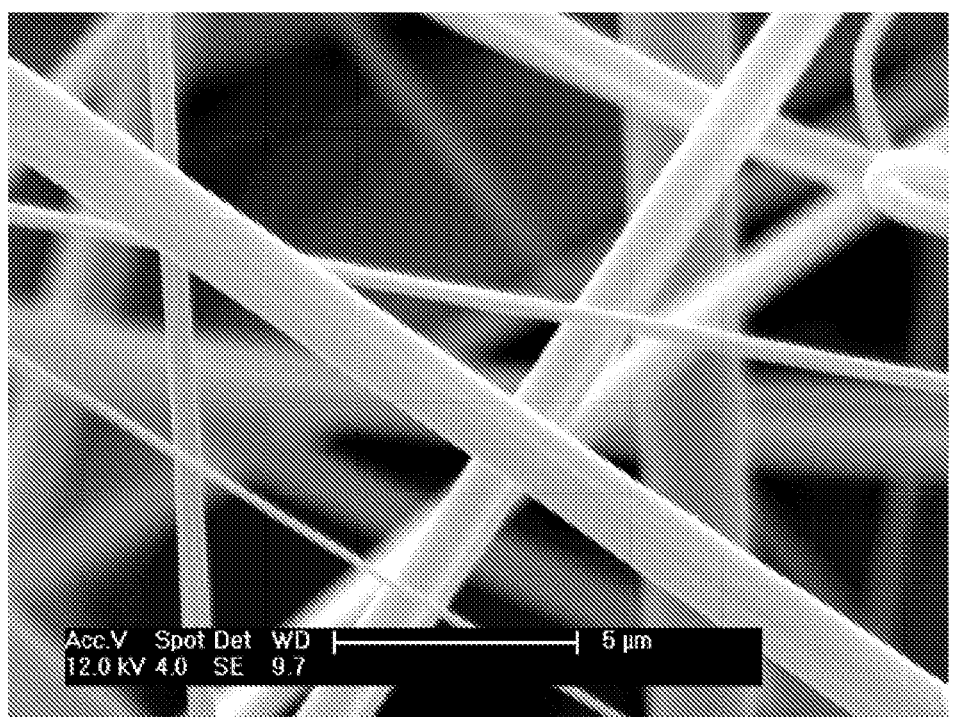
Figure 1C:
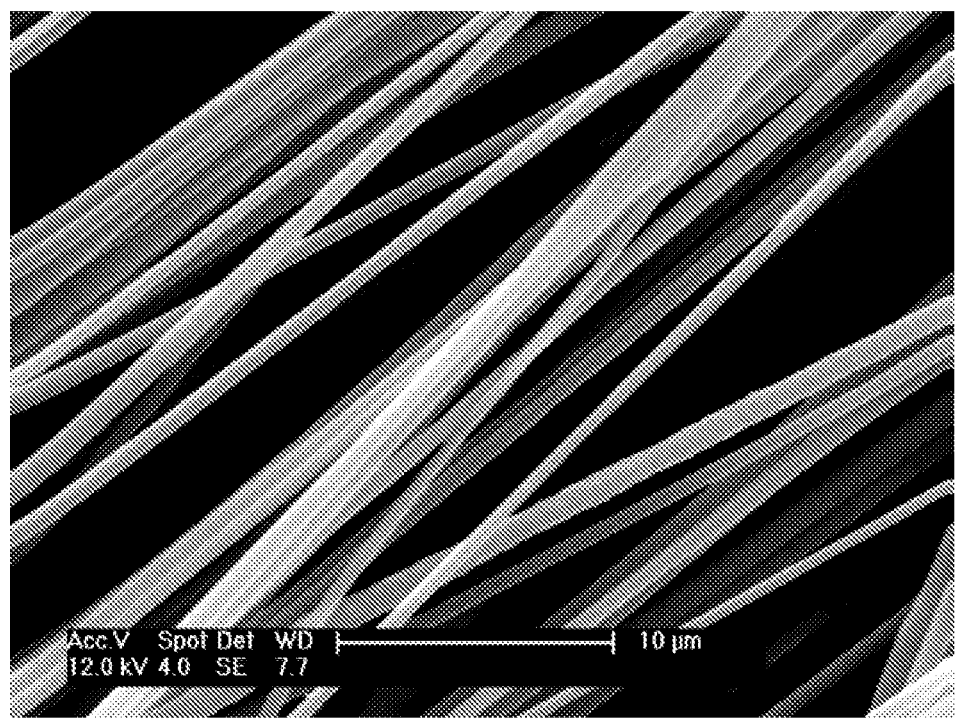

Results and Discussion:

Morphology and dimensions of Ru probe-containing fibers: The Ru probe was very soluble in HFP and a uniformly orange colored solution was formed when the Ru probe and polymer pellets were fully dissolved. Electrospinning created nano- and micro-scaled fibers (Table 1) containing the Ru oxygen sensitive probe in a single-step process. Fibers could be formed either as a randomly oriented structure (FIG. 1A-1B) or in an aligned format (FIG. 1C) depending on the set-up employed for the electrospinning process. The probe-containing fiber diameters can be adjusted by varying polymer concentrations. The morphology of the oxygen-sensitive fibers were similar to that of the probe-free fibers. SEM images (FIG. 1A-1B) show the typical high porosity associated with electrospun fibermats. The PES fibers displayed slightly larger interfiber spacing. The increased surface-to-volume ratios (compared to traditional film-based sensors) reduce barriers to efficient oxygen diffusion as the fiber diameter provides a relatively small barrier. However, such 3D structure is also important for application in reporting localized oxygen levels near individual cells as these nanofibrous structures simulate the extracellular matrix (ECM) topography to allow for close interaction of cells with the matrix and the incorporated oxygen-sensitive probes.

TABLE 1

Fiber composition, diameter, response time, and recovery time.

| Fiber | Solvent | Polymer concentration | Diameter (μm) | Response time (s) | Recovery time (s) |
|---|---|---|---|---|---|
| PCL | HFP | 5 wt. % | 0.53 ± 0.32 | 0.9 ± 0.12 | 1.98 ± 0.37 |
| PES | HFP | 8 wt. % | 0.72 ± 0.43 | 2.17 ± 0.28 | 2.43 ± 0.18 |
| PES-PCL core shell | HFP | 5 wt. %/ 5 wt. % | 0.96 ± 0.32 | 2.91 ± 0.33 | 3.33 ± 0.48 |
| Larger diameter PCL | DCM | 10 wt. % | 7.01 ± 1.37 | 1.79 ± 0.23 | 2.29 ± 0.13 |
| PCL film | HFP | 5 wt. % | NA | ~150 | ~400 |

Figure 1D:
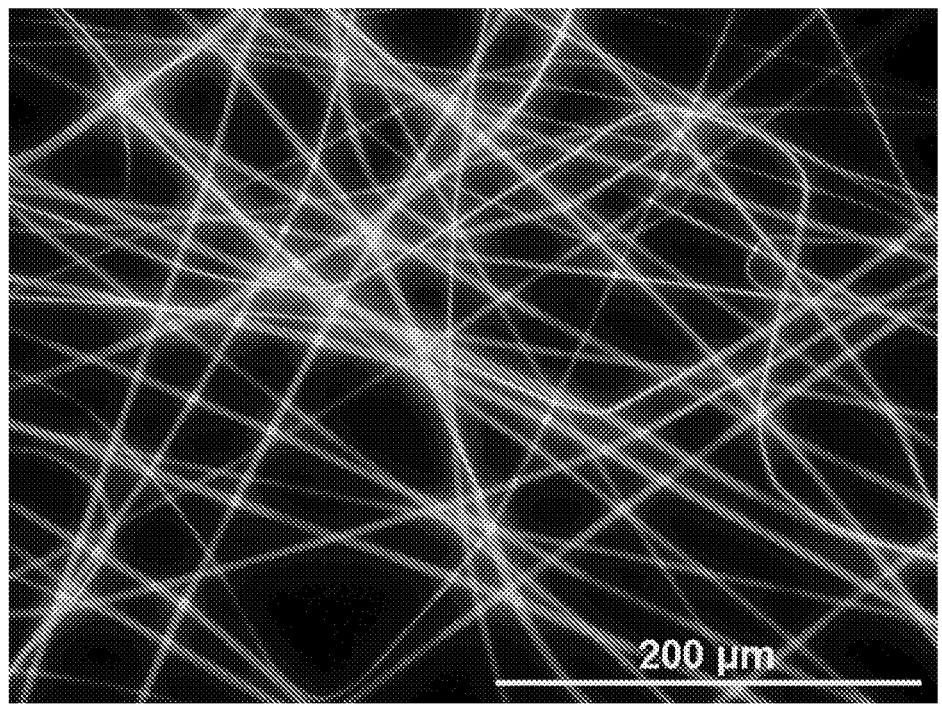
Figure 2A:
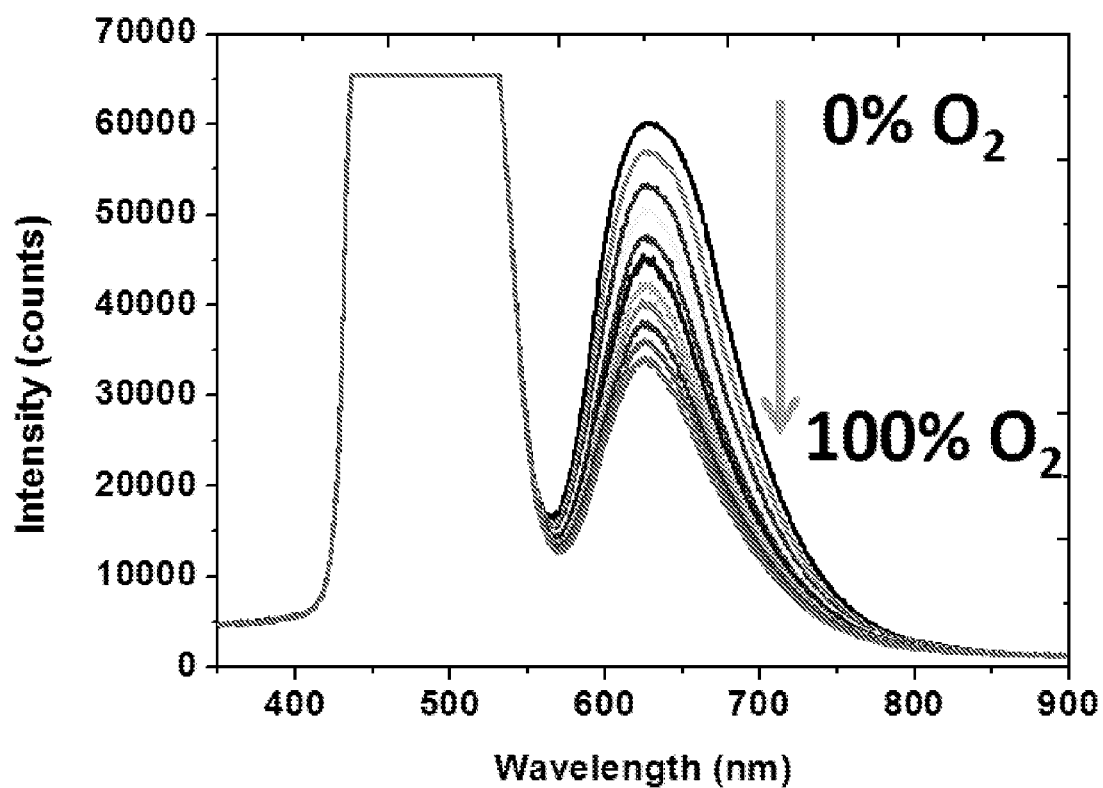
FIGS. 2A-2B are graphs showing the fluorescence response of a PCL fiber (FIG. 2A) and a PES fiber (FIG. 2B) following exposure to the various concentrations of oxygen (0-100% $O_2$).
Figure 2B:
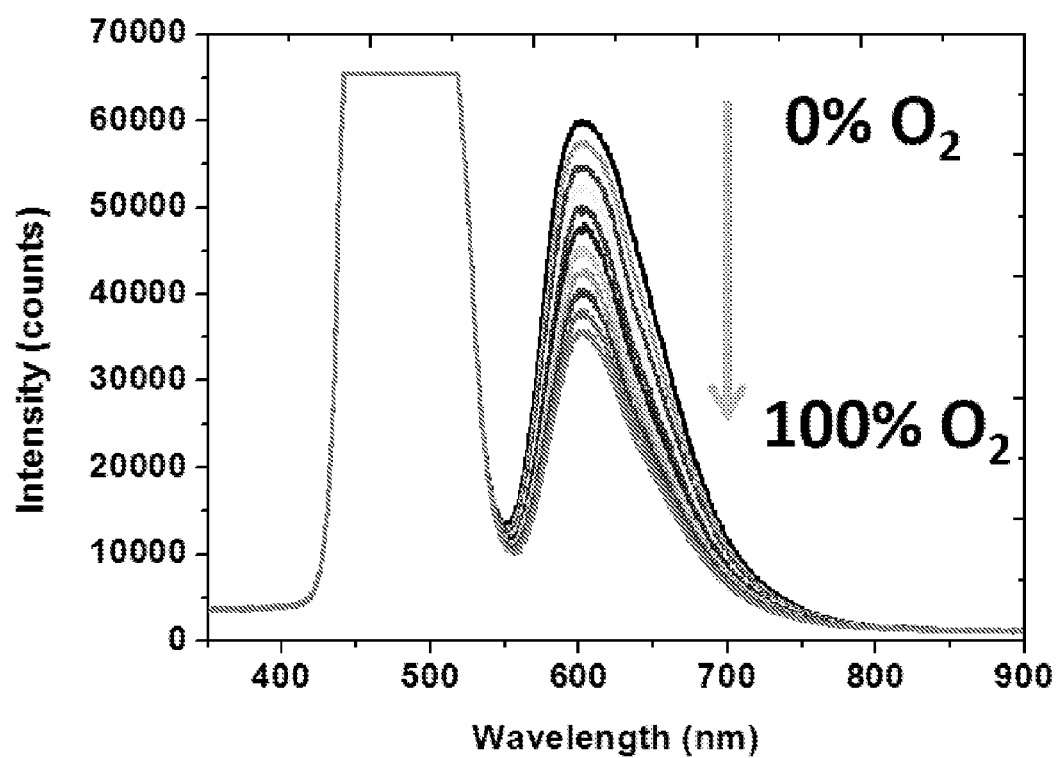
Figure 3:
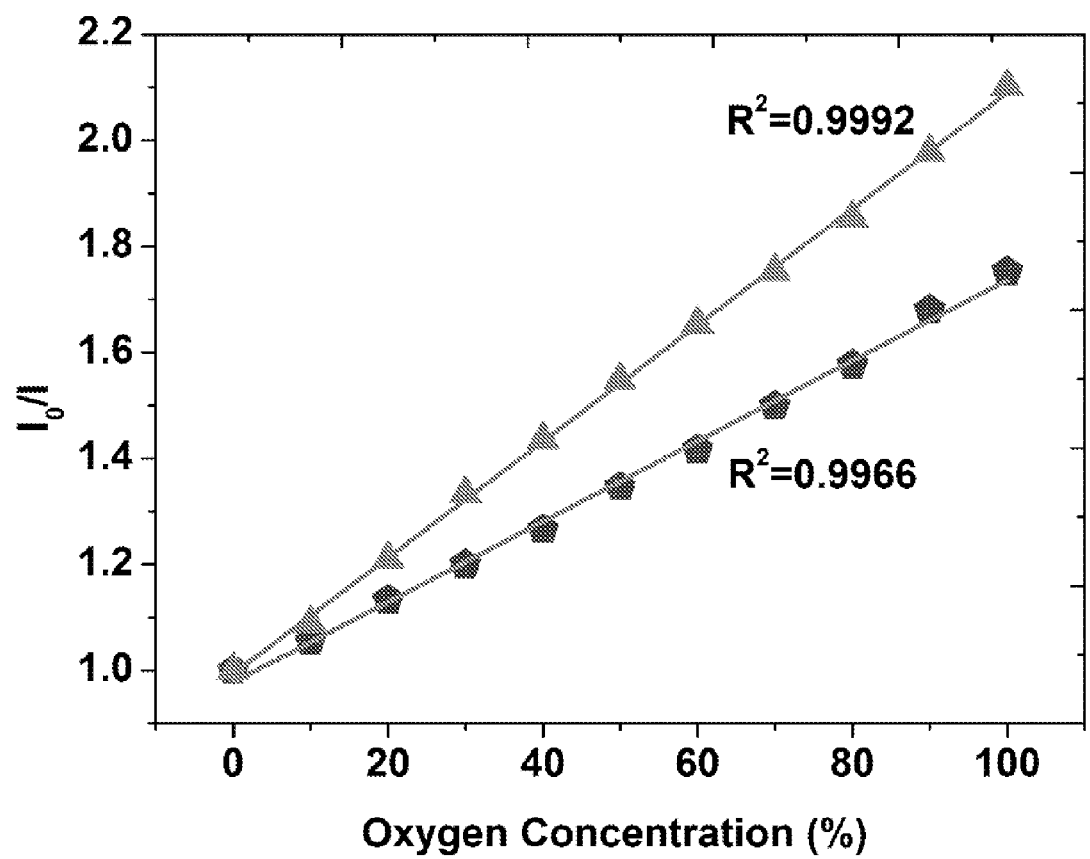
FIG. 3 is a Stern-Volmer plot representing a PCL fiber in gaseous oxygen before (pentagons) and after (triangles) 50° C. heat treatment.

Oxygen sensing in gaseous environments: The dynamic spectral response of the PCL and PES fibers to gaseous oxygen is shown in FIGS. 2A-2B. The saturated peak visible at 470 nm originates from the excitation light source. Ruthenium probe incorporated in the polymer fibers was excited by the excitation light and emitted the observed red fluorescence (FIG. 1D) wavelengths. The emission peak of the Ru probe, dissolved in ethanol, is located at 613 nm; when the fluorescent behavior of the probe was evaluated in these polymer matrices, shifts in the emission peak were observed. For the PCL matrix, an emission peak at 626 nm was observed; for the PES matrix, a peak at 604 nm was observed. The illumination-triggered fluorescence of the ruthenium probe is attributed to a metal-to-ligand charge transfer (MLCT) process in which an electron from a metal d orbital is promoted to a ligand $\pi^*$ orbital. The associated emission peak is gradually quenched as the oxygen concentration increases from 0 to 100%. The ruthenium compounds have a relatively long triplet state lifetime and display sufficient triplet-triplet energy transfer to oxygen molecules diffusing through the polymer matrix. The decreased emission intensity versus increased oxygen concentration is caused by the growing number of oxygen molecules available for energy transfer/quenching. Based on FIG. 2, the total degree of quenching observed during the transition from pure nitrogen to pure oxygen ($I_0/I_{100}$) is slighter larger for PCL fibers than that of the PES fibers. This quenching response ($I_0/I_{100}$) is closely related to the gas permeability of the polymer matrix. The quenched percentage obtained is less than those of highly gas permeable polymer such as silicones and some fluoropolymers. However, the selected PCL matrix has comparable oxygen permeability with the commonly used polystyrene matrix but greater bio-affinity in both in vitro and in vivo applications. The quenching responses of PCL and PES sensors were further examined over a range of oxygen concentrations. The relative intensity change as a function of oxygen concentration follows the Stern-Volmer equation [6]:

$$I_0/I = 1 + K_{SV}[O_2]$$

where $I_0$ and $I$ are the measured intensity in the absence of oxygen and the presence of different oxygen concentrations, $K_{SV}$ is the Stern-Volmer quenching constant and $[O_2]$ the oxygen concentration. The Stern-Volmer plot for PCL fibers in various gaseous oxygen concentrations (FIG. 3) yields a fitting coefficient $R^2$=0.9966. Excellent linearity helps avoid the use of more complex modified Stern-Volmer equations and enables easy calibration. Interestingly, after the probe-containing PCL fibers were heated to 50° C. for 12 h, both the sensitivity and linearity noticeably were improved (FIG. 3). The $I_0/I$ value at 100% oxygen concentration for the sintered PCL fibers increased by 19.9% and $R^2$ increased to 0.9992. This change in sensing efficiency is attributed to an increase in the degree of crystallinity for this relatively low-melting polymer following this exposure. As a larger fraction of the polymer chains assume a more regular, closely packed structure, any embedded Ru probe molecules would see this more uniform structure/site. Alternatively, the elevated temperature exposure could increase crystallization to reject probe molecules into the surrounding amorphous phase. This could both decrease what little multi-site occupancy exists and improve sensitivity by concentrating the probe molecules in the amorphous regions more easily permeated by oxygen. The linearity of the Stern-Volmer plot for the fiber-based sensors facilitates accurate calibration of the sensors prior to application in cell culture. A downward slope in the Stern-Volmer plot at high $O_2$ levels is often attributed to the different quenching behaviors of the luminophores on different sites.

Figure 4A:
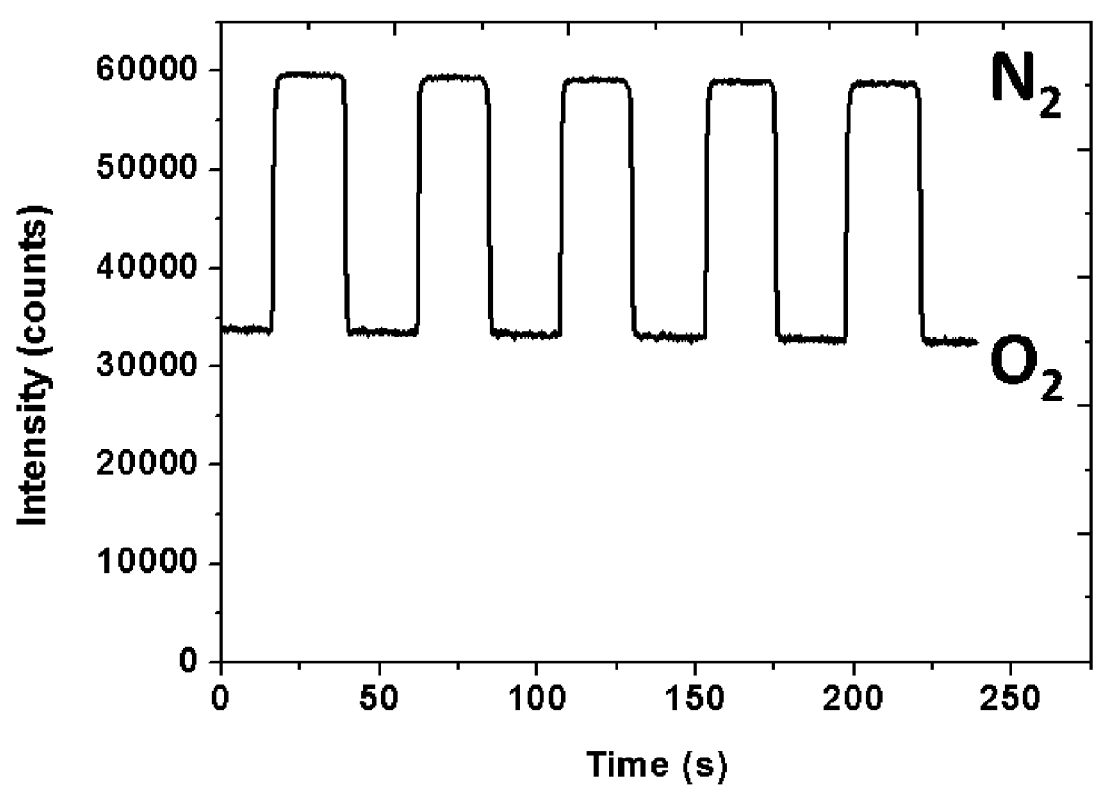
FIGS. 4A-4B shows the response of PCL fiber (FIG. 4A) and PES fiber (FIG. 4B) to cyclic exposure to $O_2$ and $N_2$.
Figure 4B:
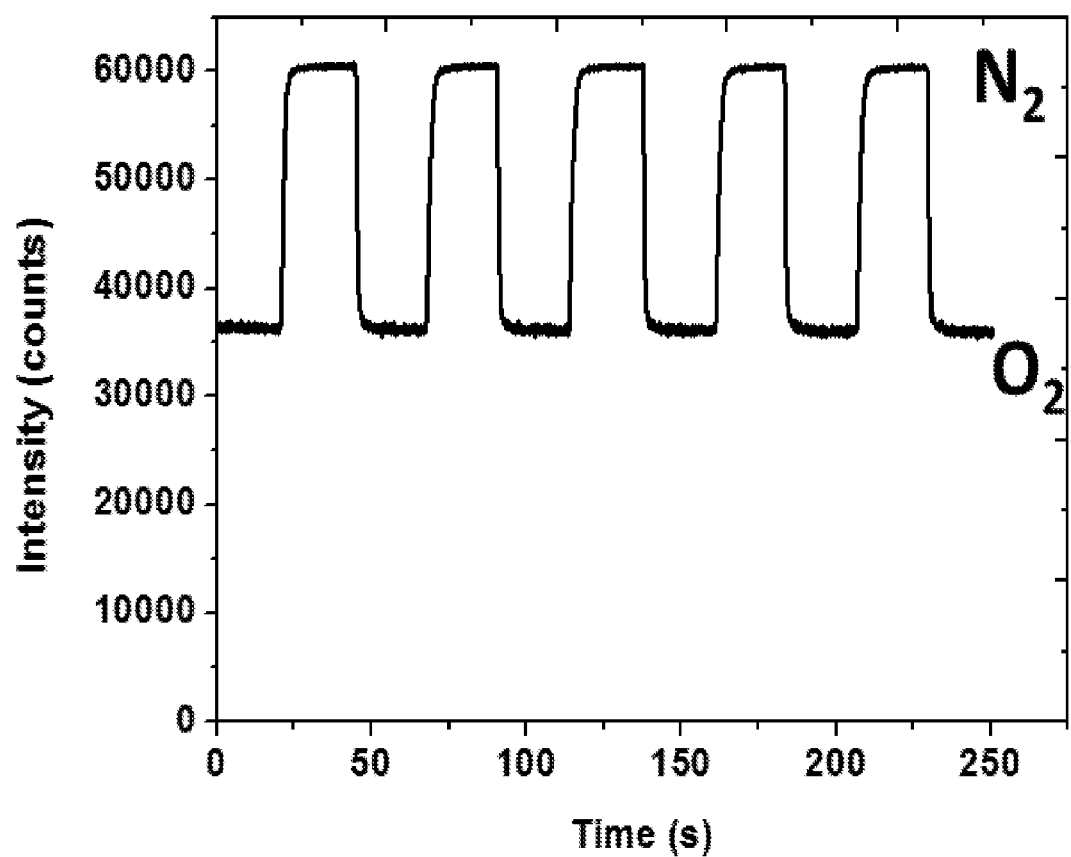

Response time: The response time was determined based on reversibility. The intensity of the emission peak for each sensor was continuously monitored and plotted in FIG. 4 for (a) PCL and (b) PES as the environment alternated from 0 to 100% $O_2$. No hysteresis was observed during these oxygen/nitrogen cycles in the gaseous state. Both the response and recovery times are defined as time required for a 95% change in intensity. This $t_{95}$ time is 0.9±0.12 s (mean±standard deviation) for PCL fibers and 2.17±0.28 s for PES following the switch from 100% $N_2$ to 100% $O_2$. Conversely, the recovery time from oxygen to nitrogen is 1.98±0.37 s and 2.43±0.18 s, respectively, likely reflecting the greater permeability of the polymer matrix for $O_2$. The response and recovery time measurements also include the time required to exchange gases with the surrounding environment. The net changes in peak intensities incurred during the transition from $N_2$ to $O_2$ are similar for PCL and PES. For comparison, the response of Ru probe-containing PCL matrix films to oxygen conditions was also measured. The matrix film reversibility was different. The $t_{95}$ value for the film was at least two orders of magnitude greater than that of the electrospun fiber matrices. The effective area of a dense film for oxygen to diffuse into is equivalent only to the net surface area of the film. In contrast, the specific surface area of electrospun nanofibers is orders of magnitude larger than their 2D film counterparts. The small diameter and porous nature of the electrospun fibers tends to provide a faster response time compared to 2D film sensors. Diffusion limitations preventing easy access to the probe are significantly minimized as the necessary depth of penetration of oxygen into the matrix is greatly reduced. Fast response times are critical to real-time monitoring of oxygen concentrations in targeted biological applications.

Figure 5A:
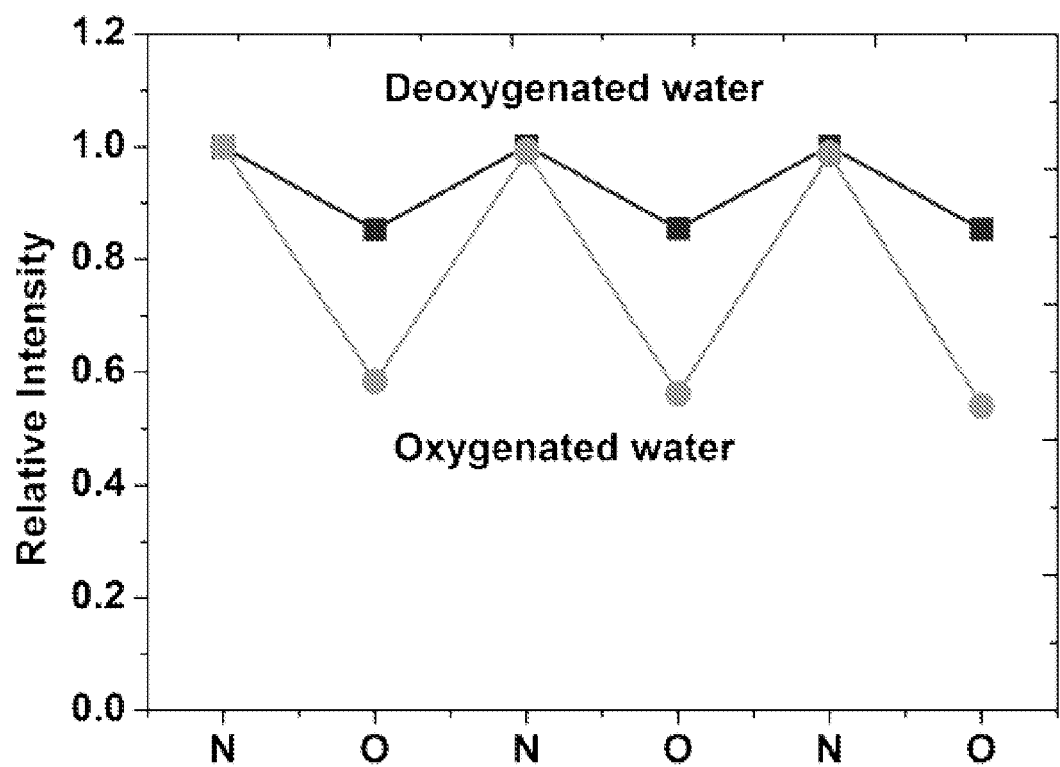
FIGS. 5A-5B are line graphs illustrating the reversibility of various fibers and the Stern-Volmer derived plots.

Response to changes in dissolved oxygen: Fiber response to changes in dissolved oxygen in aqueous solution was tested by altering the aqueous environment of the samples between nitrogen-saturated and oxygen-saturated water. To attain complete saturation, ~30 min of continuous bubbling of each gas in the chamber was used to ensure equilibrium prior to measurement. For each sample, the fluorescence images were taken each time the aqueous condition was changed (in either the oxygenated or deoxygenated conditions) and the measured image intensity normalized relative to the initial intensity. Similar to the gaseous environments, the fluorescence intensity of Ru probe in the fibers decreased as the nitrogen-saturated solution was flushed with oxygen. All samples showed good reversibility as the intensity of the sample repeatedly changed from the initial value to a specific quenched value dependent upon on polymer identity when switching between deoxygenated and oxygenated water. About 44% of the intensity is quenched for PCL sample after full equilibrium when the bubbled oxygen was reached; for PES this value is much smaller, around 18% (FIG. 5A).

Figure 5B:
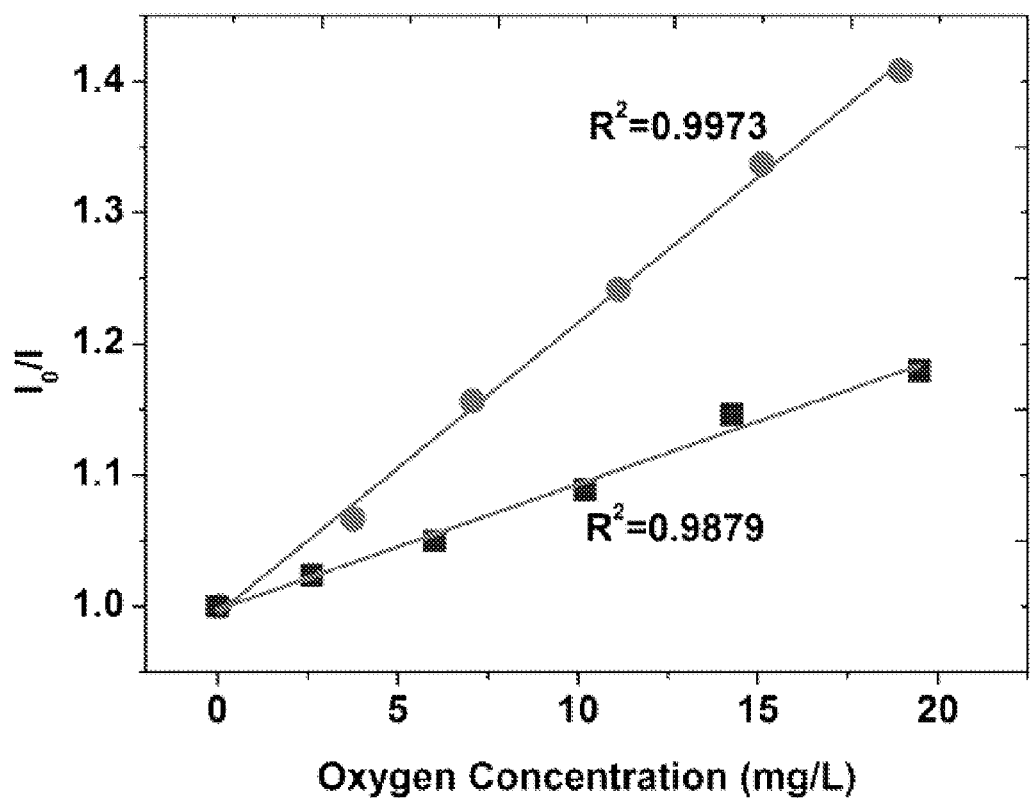

Both PCL and PES sensors display a good linear fit to the Stern-Volmer equation (FIG. 5B) over the full range of the experiment (0-20 mg/L) with fitting coefficients ($R^2$) of 0.9973 and 0.9879, respectively. The Stern-Volmer constant calculated from the fitted plot is $2.2 \times 10^{-2}$ (mg/L)$^{-1}$ for PCL and $1.1 \times 10^{-2}$ (mg/L)$^{-1}$ for PES fibers. The linear fit of the data facilitates the calibration of the sensor to real dissolved oxygen contents. The linear relationship covers the entire range of oxygen concentrations expected in cell culture (0-9.1 ppm). The good linearity of the Stern-Volmer plot indicates that the quenching compound, oxygen in this case, is readily and equally available to luminophores embedded in the matrix. Electrospun sensors produce a clearly linear dependence due to their small diameters and lack of multiple luminophore sites. SEM images reveal these small diameters and the porous nature of the overall assembly allowing easy diffusive access. Therefore oxygen molecules, in either the gaseous state or dissolved in aqueous solution, can freely diffuse into the electrospun mats and reach the embedded luminophores by penetrating the polymer fiber through radii of only 260-360 nm. The pathway lengths allowing access in these fibers are relatively short compared to conventional film sensors. The easy accessibility of oxygen to the probe molecules results in quick responses as well as excellent Stern-Volmer linearity.

In addition to easy accessibility, this linear relationship also provides indicates uniform probe distribution within the polymer matrix. Heterogeneity involving three different scales is thought to be the main contributor to non-linear Stern-Volmer plots: a) macroheterogeneity due to unsatisfactory fabrication b) microheterogeneity due to either matrix crystallization, cracking or phase separation of the polymer and c) nanoheterogeneity due to molecular scale orientation or structure differences that could alter local oxygen diffusion. Under electrospinning fabrication conditions such heterogeneities are clearly absent. Before electrospinning, Ru probe molecules are uniformly dispersed in polymer/solvent solution. Luminophores in liquid solvents are exposed to identical environments on average time scales and exhibit linear Stern-Volmer plots. During electrospinning, a high electrostatic voltage is applied to the precursor solution. The high repulsive force within the charged solution stretches the solution to form a jet and the solvent rapidly evaporates before the jet deposits on the grounded metal collector. This process happens over such a short time scale that polymer chain rearrangement is restricted and probe molecules are likely "frozen" into place within the polymer matrix. Therefore, it is assumed that the uniformity of the environment surrounding the probe molecules in the resulting fibers is similar to that in the liquid especially when compared to literature reports of multi-site occupancy in thin polymer film matrices.

Effects of fiber diameter: The diameters of the oxygen sensitive fibers were measured from the SEM images. The diameters of 50 randomly selected fibers were measured for each polymer matrix. HFP-spun PCL fibers averaged 0.53±0.32 µm; PES 0.72±0.43 µm. To investigate the effects of fiber diameters on sensing performance, a PCL/Ru probe solution was fabricated using dichloromethane (DCM) instead of HFP while maintaining the same PCL/Ru ratio and electrospun under the same conditions. DCM as an electrospinning solution produces PCL fibers with much larger diameters (7.01±1.37 µm) and pore sizes allowing easy cell infiltration. The oxygen sensitivity of Ru-containing DCM fibers was tested using the same atmospheric oxygen/nitrogen mixtures as before to determine quenching behavior and response time. The total magnitude of the quenched emission peak for DCM fibers cycled from $N_2$ to $O_2$ ($I_0/I_{100}$) is 4.0±1.7% smaller than that of the smaller diameter HFP fibers. The response time and recovery times for these DCM fibers are 1.79±0.23 s and 2.29±0.13 s, respectively. These values are 0.89 s and 0.31 s slower, respectively, than those of the smaller diameter HFP-fabricated fibers. An order of magnitude increase in PCL fiber diameter evidently reduces the sensitivity and increases the necessary response time; conversely, decreases in fiber diameter to less than 0.5 µm would likely decrease response times even further if needed. An increase in diameter imposes easily detected limits on oxygen diffusion through the polymer matrix.

Figure 6A:
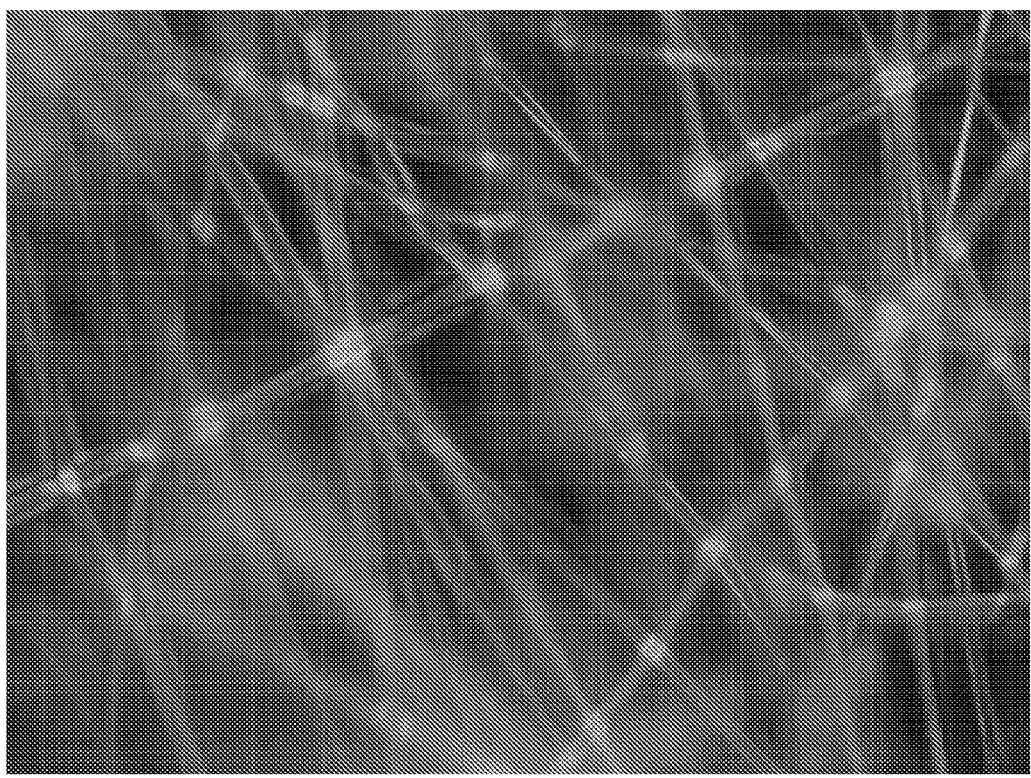
FIGS. 6A-6C show representation of a PES-PCL core shell fiber and response of the fibers to cyclic $N_2$—$O_2$ gas exposures.
Figure 6B:
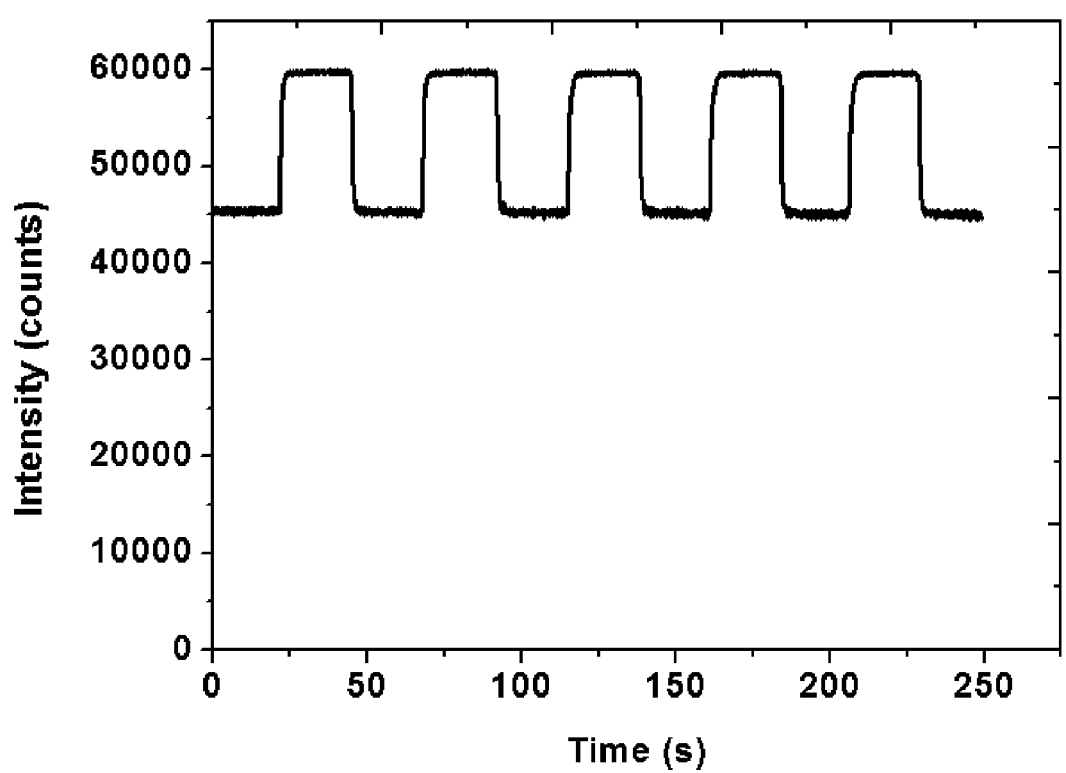

PES-PCL core shell fiber: A core-shell configuration of the electrospun oxygen-sensitive fibers was explored with the probe containing PES serving as the 'core' and pure (i.e., not probe-containing) PCL acting as the 'shell'. The core-shell fiber being investigated improves sensor performance in several respects: (1) the PES provides greater mechanical support for the sensor; (2) the PES core better protects the probe from photobleaching; (3) the PCL shell improves biocompatibility versus PES alone; and (4) the addition of a probe-free shell structure could potentially slow probe leaching within the polymer matrix. The morphology typical of electrospun fiber is retained and the core-shell fibers have diameters of 0.96±0.32 µm. To prove that the desired core-shell structure was achieved, a bright field microscope image and a corresponding red fluorescence image were obtained and merged (FIG. 6A). The green portion of the image of the fibers represents the auto fluorescence of the PCL shell under bright field illumination and the orange region represents the probe embedded in the PES core. The core-shell structure shows defined boundaries between the fluorescent core and the PCL shell. In terms of sensing performance—as shown in FIG. 6B—the fiber exhibits good fluorescence intensity reversibility when cycled between $N_2$ and $O_2$ gases. However, the response time is slightly reduced (by ~15% from 2.17±0.28 s to 2.91±0.33 s) compared to PES fibers alone. Although the core-shell fibers provide relatively low sensitivity, this technique could potentially be applied to sensor production involving any two polymers that can be electrospun to ideally combine the preferred properties of each polymer to both biologically and mechanically tailor overall sensor behavior.

Oxygen sensors in different forms have been found applications in cell culture devices or even inside cells. An oxygen sensitive microwells sensor was developed by embossing polystyrene and platinum(II) octaethylporphyrin ketone thin films and used this system to monitor oxygen tensions around kidney cells. Other work conducted shows fabrication of biocompatible fluorescent nanoparticles capable of reporting oxygen ratiometrically and applied the nanoparticles inside the living human hepatocellular liver carcinoma(HepG2) cells. Compared to such sensors, nanofiber based oxygen sensors are promising for their excellent biocompatibility and the possibility that they can be easily integrate into standard cell or tissue culture device. Electrospun fibers have a wide range of applications in tissue engineering for their controllable nano-scaled dimensions and features. Core-shell structure platform could maintain the biological advantages of the shell while including other functional ingredient inside the core. These nanofibers are also applicable to electrospun fiber based cell culture plates for the study of local oxygen gradients while cells are migrating.

Figure 6C:
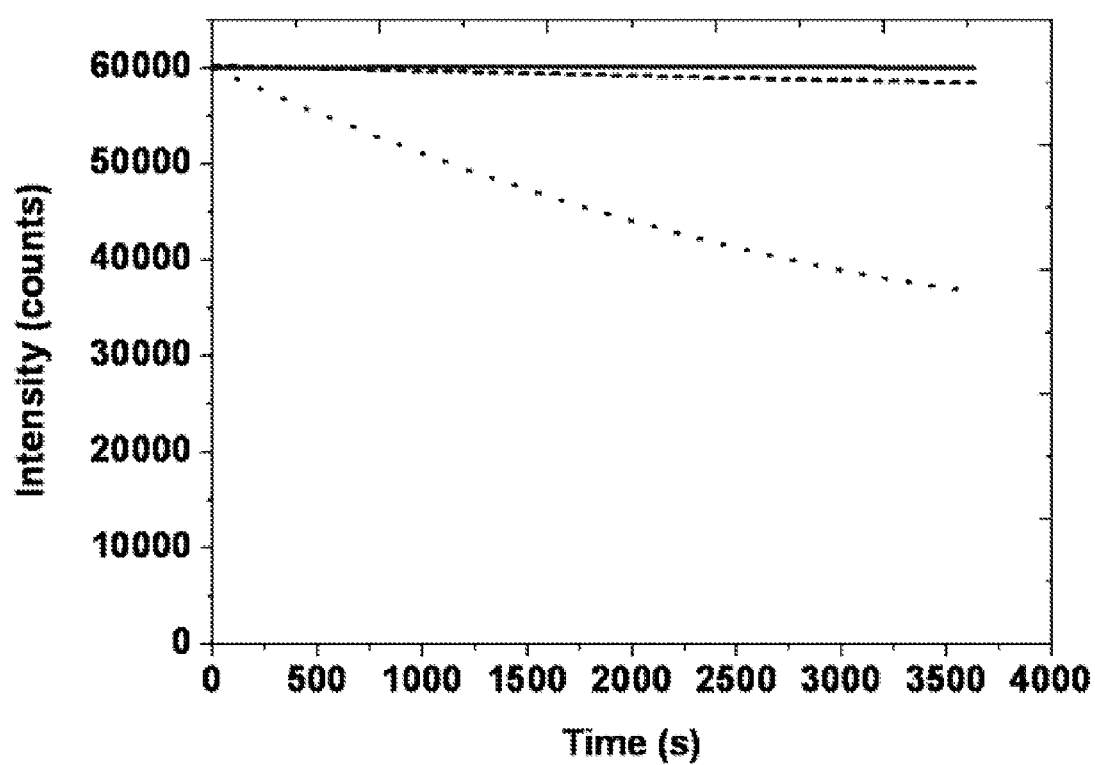

Photobleaching: Photobleaching and photochemical destruction of the fluorophore from light exposure was investigated. Under continuous excitation using the blue LED, the intensity of the emission peak for each sensor was monitored to examine photostability. During 3600 s of intensive illumination, PCL fibers exhibit obvious signal decay (FIG. 6C). However, for PES fibers no noticeable photobleaching was observed throughout the duration of the test. PES is a heat-resistant, transparent, tough and rigid polymer with higher glass transition temperature that likely better limits the migration and aggregation of probe molecules. The high thermal and chemical stability makes PES a good matrix material for sensors having steady output and resistance to harsh conditions. A similar polymer, polysulfone, has been shown to function as an appropriate matrix polymer that could withstand autoclaving at 135° C. for 60 min without any major changes in sensing abilities. The 3600 s exposure tests in this work show that PES efficiently protects the embedded Ru probe and avoids significant photobleaching. Similarly, PES-PCL core-shell fibers show satisfactory photostability and only slight intensity losses during the same 3600 s exposure (FIG. 6C).

Figure 7A:
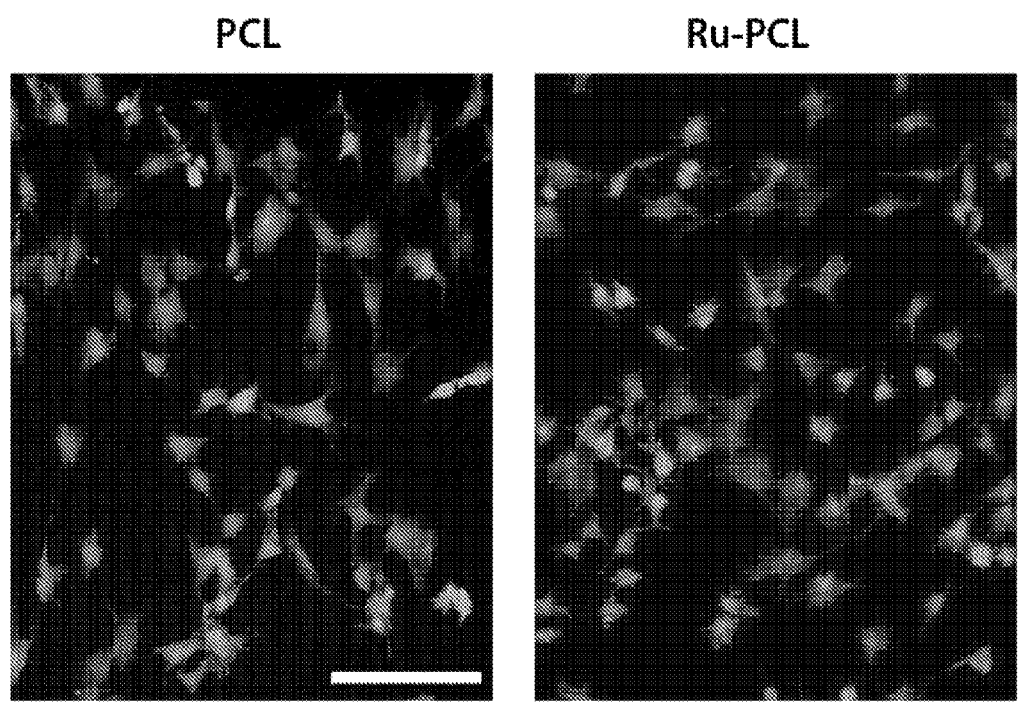
FIGS. 7A-7B show images and graphs of the quantification of cell density and percentage dead cells of two different glioblastoma cell lines.
Figure 7B:
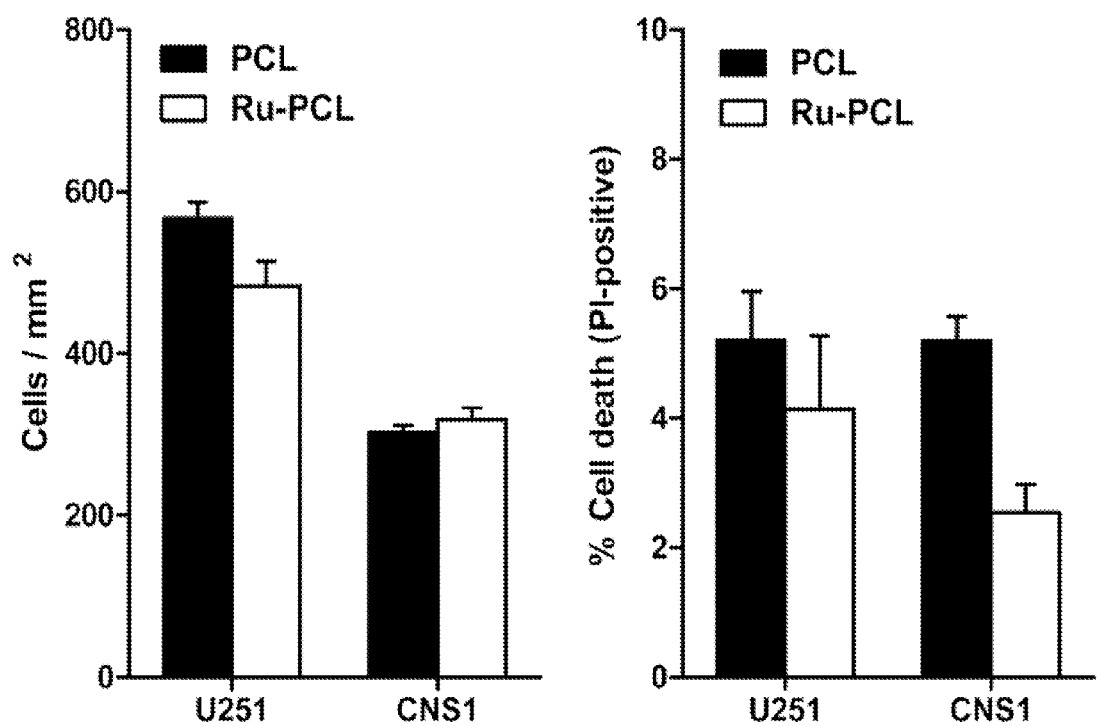

Oxygen-sensing nanofiber cytotoxicity: To investigate cytotoxicity potentially caused by the presence of the Ru probes within these nanofiber sensors, both electrospun PCL without any probe molecules and the Ru probe-containing PCL nanofiber sensors were investigated using adherent cultures of glioblastoma cells. In FIG. 7A, the observed cell morphologies and association of the cells on the different types of fibers are essentially identical. As shown in FIG. 7B, cell attachment (cells/mm$^2$) and viability (% dead/total cells) on Ru probe-containing nanofibers are not statistically different from probe-free PCL nanofibers, indicating that the fluorophore did not cause any significant toxicity on cultured cells.

Conclusions

In this study, it was demonstrated that nanofiber-based sensor systems can achieve a highly linear range of net fluorescence emission versus oxygen content. The apparently small number of sites upon which the probe sits in this system relative to film-based systems allows for minimal deviations from Stern-Volmer linearity that contrasts sharply with film-based polymer carriers. Further improvements in accuracy/linearity can apparently be achieved by thermal exposure. Larger fiber diameters provide enough of a diffusion barrier to decrease sensitivity while having relatively little effect on recovery time likely due to the more limited interactions of $N_2$ with the polymer matrix. Comparing PES to PCL shows that composition has stronger effects on both response and recovery time than PCL diameter. PES more efficiently protects the probe from photobleaching. The combination of a PCL shell with a PES core allows utilization of PES's advantages in protecting the probe while providing a more biocompatible surface. The use of electrospun core-shell fibers as oxygen sensors has practical advantages over monolithic fibers while both exhibit substantial advantages over thin films. Finally, even the non-core shell compositions containing the Ru oxygen probe result in no apparent cytotoxicity in adherent glioblastoma cell populations. Future work will focus on other polymer and probe combinations to improve the sensitivity and the use of cell culture plates with built-in nanofiber sensors that monitor local oxygen contents.

Example 2

Polydimethylsiloxane Core—Polycaprolactone Shell Nanofibers as Biocompatible, Real-time Oxygen Sensors PDMS-PCL core-shell nanofibers comprising oxygen probes inside the PDMS core were fabricated. The PCL shell helps maintain the fiber morphology prior to and during cross-linking while adding biocompatibility for cell attachment and migration. Three oxygen-sensitive probes and two different PDMS matrices were fabricated to establish the effects on properties associated with oxygen sensing in biological systems. The three sensing probes comprised ruthenium-based complexes and platinum-based porphyrin sensors. In addition, CNS1, U251 and GBM34 cell lines were cultured on these as-spun core shell fibers to determine whether the presence of the porphyrin dyes within the core carried with it significant cytotoxic effects. The resulting electrospun fiber platform was both biocompatible and has the capability to report local oxygen contents to provide valuable information establishing the relationship between cell migration and locally variable hypoxicconditions.

Materials and Methods:

Materials: Polycaprolactone (Mn=70,000-90,000) was purchased from Sigma-Aldrich (St. Louis, Mo., USA). Silastic®T-2 two-part silicone was obtained from Dow Corning Corporation (Midland, Mich., USA) and Permatex® one-part moisture cure room-temperature vulcanizing (RTV) silicone was purchased from Illinois Tool Works Inc. (Hartford, Conn., USA). Oxygen sensing probes, tris(4,7-diphenyl-1,10-phenanthroline) ruthenium(II) dichloride (Ru(dpp)(Cl)), tris(4,7-diphenyl-1,10-phenanthroline) ruthenium(II) tetraphenylboron(Ru(dpp)(PB)) and platinum (II) octaethylporphine (PtOEP) were acquired from Alfa Aesar (Ward Hill, Mass., USA). 1,1,1,3,3,3-hexafluoro-2-propanol (HFP) was obtained from Oakwood Products Inc. (West Columbia, S.C., USA). Dichloromethane (DCM) and toluene were also obtained from Sigma-Aldrich.

Instruments: Scanning electron microscopy (SEM) (FEI Company, Hillsboro, Oreg., USA) was used to examine the morphology of the electro-spun core-shell following the application of a thin gold coating. Luminescence images of the fibers were captured on a fluorescence microscope (Nikon Inc. Melville, N.Y., USA) using a filter set for red fluorescence (EX: 530-560 nm, DM: 570 nm, BA: 590-650 nm). The luminescence spectra of the core-shell fibers and the strip chart for the emission peak as function of time were recording using a fluorescence spectrometer (Ocean Optics Inc., Dunedin, Fla., USA). Blue LED light at 470 nm was guided through the 600 μm VIS-NIR fibers to act as the excitation source. The optic probe of the spectrometer was fixed to directly point at the experimental samples.

Fabrication of electrospun core-shell fibers: The PCL solution used for the shell of electrospun fibers was fabricated by dissolving 5 wt % PCL in HFP to form a uniform, clear solution. Solutions intended for the oxygen-sensitive core of the fibers were made by dissolving the luminescence probes in appropriate solvents containing the corresponding silicones. Typical weight ratios of probe to silicone for Ru(dpp)(Cl) in T-2 PDMS were 1:1000 and the two part silicone solution (base: curing agent=10:1 by weight) concentration in DCM/toluene mixture (3:2 by weight) was 20 wt %. For the RTV silicone solution, 5 mg Ru(dpp)(B) was dissolved in 20% RTV silicone solution containing 1 g silicone. The same 1:200 dye-polymer weight ratio and polymer concentration were applied for PtOEP/RTV silicone system with chloroform as the solvent for PtOEP and PDMS. Core-shell fibers were produced by a simultaneous co-axial electrospinning of two polymer solutions through two concentric blunt needles. In all cases a flow of 1 mL/h was used for the 'core' and 4 mL/h for the 'shell' solution. A high voltage DC power supply (Glassman High Voltage, Inc., High Bridge, N.J., USA) set to be 25 kV and a 20 cm tip-to-substrate distance was used for all electrospinning processes. As-spun Silastic® 'core' fibers were held at room temperature for 24 h before use to allow the core to fully cure. For the Permatex® moisture cure silicone, the samples were placed in a sealed container maintained at a relative humidity >80%.

Gaseous oxygen sensing performance: The sensing fiber mats were cut into 1×1 cm squares and glued on edge to the inner wall of a glass bottle. The oxygen gas concentration was controlled by adjusting the relative flow rates of oxygen and nitrogen by a gas mixer (Omega Engineering, USA). Spectra were recorded by the Spectra Suite software of the spectrometer when the environmental oxygen reached equilibrium. The reversibility and response time were revealed from the intensity change of the emission peak as the environment was cycled between pure nitrogen and oxygen.

Dissolved oxygen sensing performance: A similar arrangement involving a large glass container was used to immerse the sample into water to measure the intensity changes in response to variations in dissolved oxygen. The glass bottle was contained within a water bath so that temperature could be precisely controlled. The desired gas mixtures emerging from the gas proportioner were used to sparge the water for a sufficiently long (~30 min) time to ensure that equilibrium was reached prior to measurement. A commercial oxygen meter (Hach Com-pang, Loveland, Colo., USA) was used to correlate the intensity of the core-shell fiber with the real oxygen content measured by the meter. The reversibility and photobleaching data in solution were obtained by continuously monitoring the emission peak versus the dissolved oxygen level and time.

Cell culture experiments: To establish whether these oxygen-sensing fibers were cytotoxic to cells representative of the intended application, cell culture experiments were performed with two well-established glioblastoma cell lines (U251MG and CNS1) as well as a primary culture of glioblastoma stem-like cells (GBM34). U251MG cells were cultured in Dulbecco's modified Eagle's medium (DMEM, containing 4.5 g/L glucose and 10% v/v fetal bovine serum) while CNS1 cells were cultured in RPMI-1640 medium (containing 2 mM 1-glutamine and 10% v/v fetal bovine serum. GBM34 cells were cultured in DMEM containing F-12 nutrient mixture (DMEM/F12), supplemented with 2 mM 1-glutamine, 20 ng/mL human epidermal growth factor, 20 ng/mL human basic fibroblast growth factor, 2 μg/mL porcine heparin, and the vitamin supplement B27 (Invitrogen). All media included 50 UI/mL penicillin and 50 μg/mL streptomycin to prevent bacterial growth. To assess viability, 15 mm round glass coverslips were coated with PCL or PDMS(PtOEP)-PCL nanofibers and placed in 24-wellplates. Wells were washed with phosphate buffered saline and coated with bovine fibronectin (5 μg/mL, Invitrogen) for 2 h at room temperature. Cells were gently dissociated when they reached 80% confluence and seeded at an average density of 10,000 cells/well. Cells were cultured for 48 h and subsequently co-stained with Calcein-AM (1 μg/mL, Invitrogen) and propidium iodide (0.5 μg/mL, Invitrogen), following standard protocols. Fluorescence microscopy was used to quantify live (calcein-positive, green fluorescence) and dead (PI-positive, red fluorescence) cells. Image analysis and automated cell counting were performed using ImageJ (v.1.47) software. To quantify cell migration on nanofibers, cells were trypsinized and cultured at low density in ultralow-attachment 96-well plates (Corning) for 48 h, in order to form suspended tumorspheres (350-400 μm diameter). Tumorspheres were individually seeded n nanofiber coated-slides and imaged by fluorescence microscopy to analyze cell migration. The dispersion of the cells after 48 h was measured and used to calculate the cell migration index (t48/t0).

Results and Discussion
Results

Compositions of PDMS-PCL fibers containing oxygen sensitive probe: Three combinations of sensing probe and PDMS fibers were fabricated and the specifications are listed in Table 2. For sample S1, only 0.1% of Ru(dpp)(Cl) was loaded into the two-part PDMS core of the fibers without delaying curing. On the other hand, for sample S2, 0.5% weight of the sensor was added. The same probe 0.5% concentration was used for moisture cured PDMS fibers containing PtOEP (S3).

TABLE 2

Specifications of PDMS-PCL core-shell fibers.

| Sample | Probe | PDMS | Ratio | Diameter (nm) | Emission peak (nm) |
|---|---|---|---|---|---|
| S1 | Ru(dpp)(Cl) | two-part | 1:1000 | 512 ± 195 | 618 |
| S2 | Ru(dpp) (PB) | moisture cure | 1:200 | 401 ± 131 | 622 |
| S3 | PtOEP | moisture cure | 1:200 | 570 ± 192 | 645 |

Figure 8A:
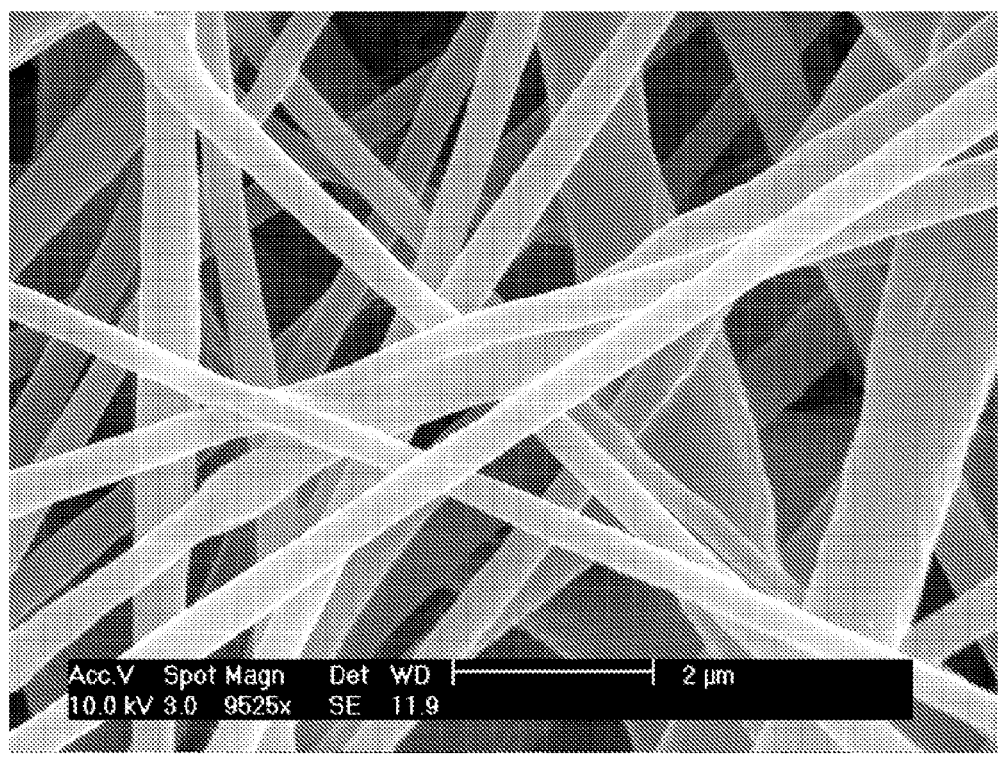
FIGS. 8A-8F are SEM (left) and fluorescent (right) images of PDMS-PCL fibers.
Figure 8B:
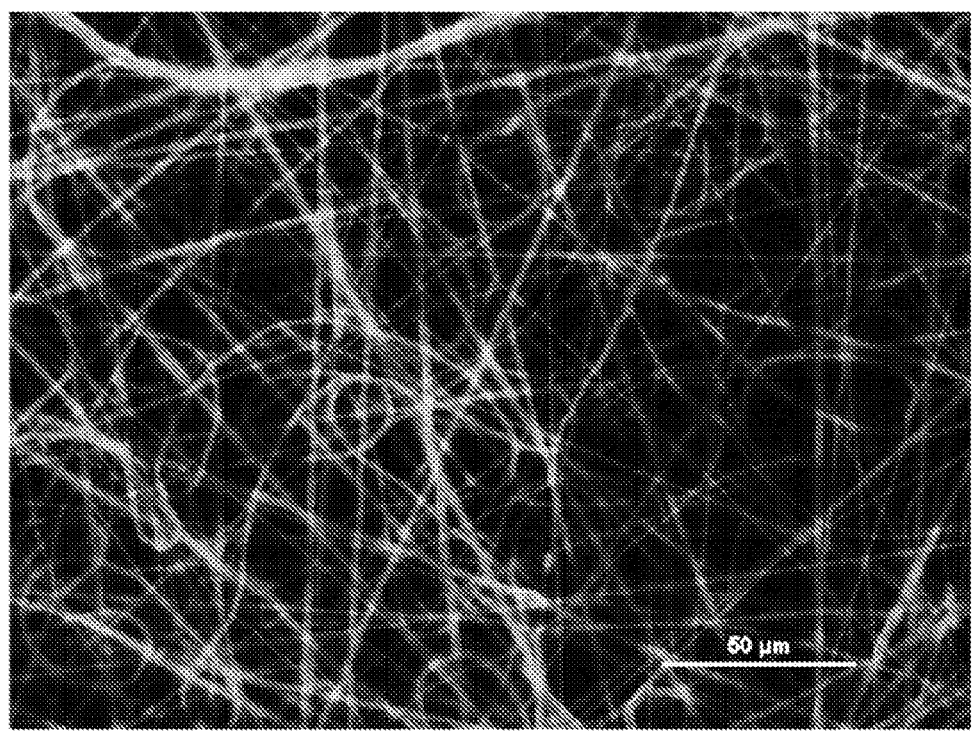
Figure 8C:
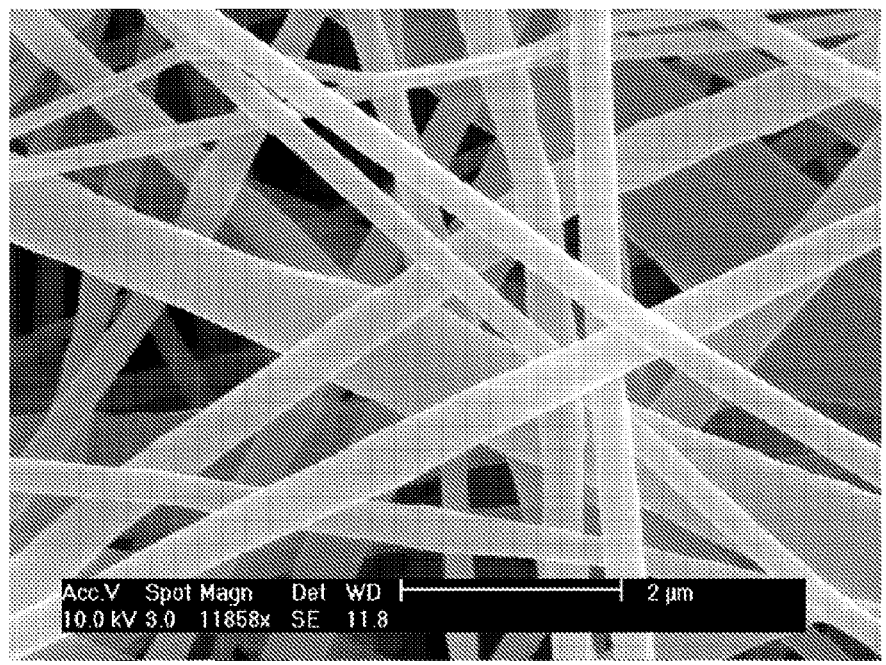
Figure 8D:
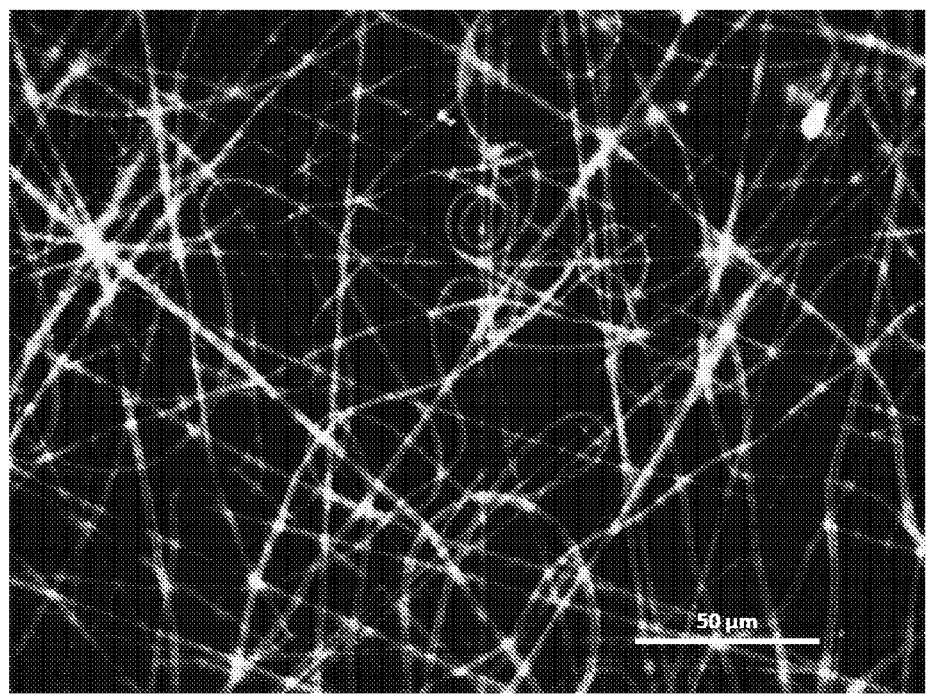
Figure 8E:
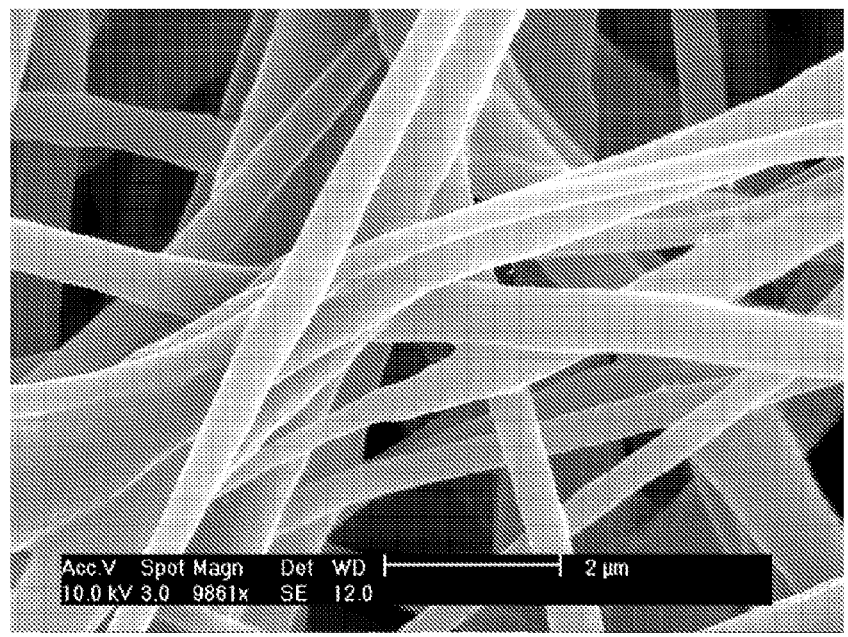
Figure 8F:
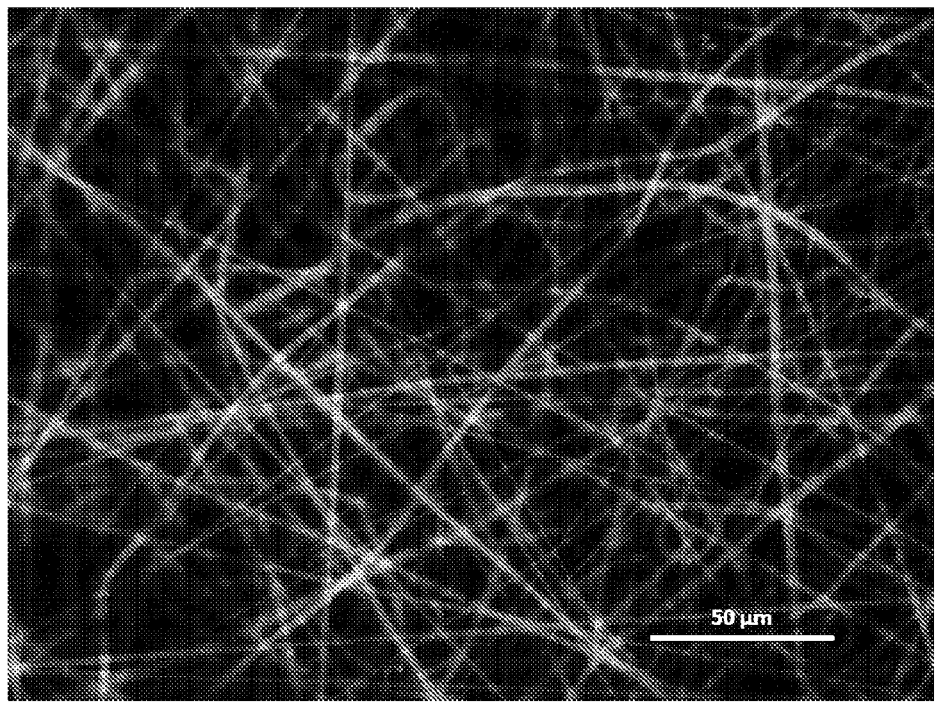

Morphology of the core-shell fibers: The morphology and luminescence of electrospun PDMS core, PCL shell fibers containing Ru(dpp)(Cl) in the core (S1) is shown in FIGS. 8A and 8B. The relative flow rate of the core and shell polymer solutions during electrospinning is a factor controlling the formation of PDMS-PCL fibers and final sensing properties of the core-shell fibers. The PDMS core as-spun is in its viscous state and would normally produce a film under these deposition conditions. The high PCL shell flow rate helps ensure the 'electrospinnability' of these core-shell fibers. However, a too-thick PCL shell would increase the diffusion path length of oxygen in the PCL shell that has lower permeability than the PDMS core. In this example, the relative core and shell flow rates were fixed at a ratio of 1:4. Similar fibers could also be achieved for S2 and S3 samples as shown in the SEM (FIGS. 8C and 8E) and fluorescent images (FIGS. 8D and 8F). Higher probe solubility makes individual fibers of S2 brighter than S1. Comparable fluorescent images could be obtained for both samples but with different acquisition times (600 ms for S1 and 200 ms for S2). There is no significant morphological difference for these PDMS-PCL core-shell fibers compared to PCL fibers (images not shown). The fiber diameters (average±standard deviation) of all three samples are also listed in Table 2.

Figure 9A:
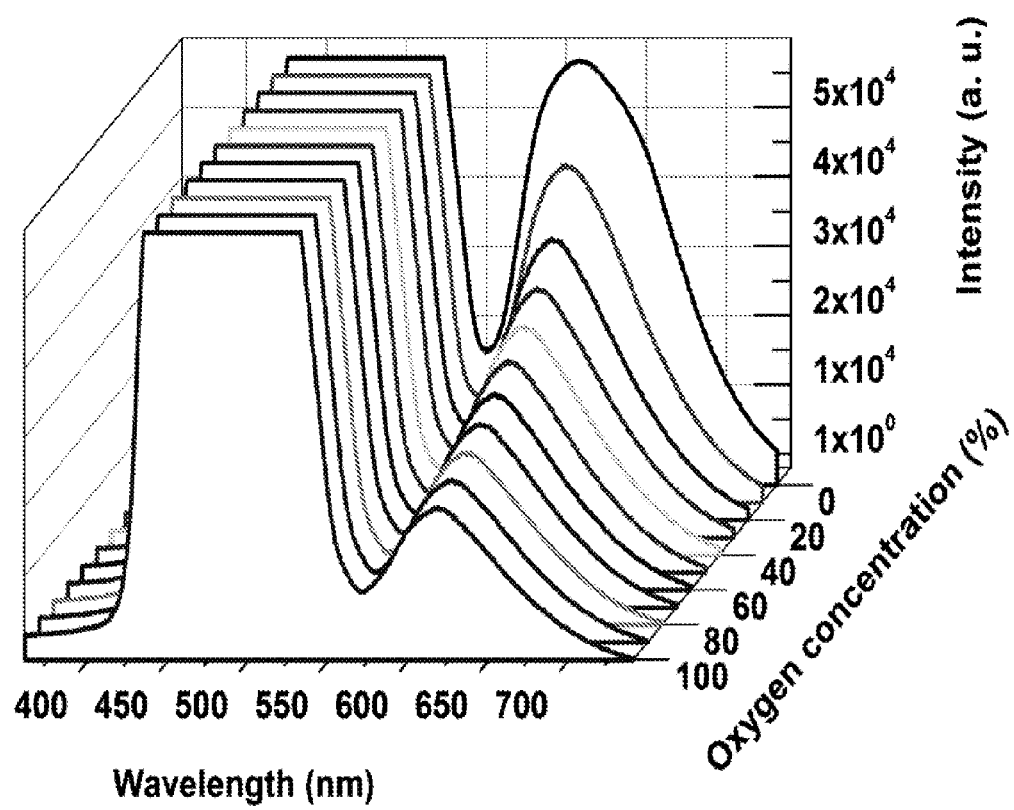
FIGS. 9A-9F are graphs illustrating spectral response to gaseous oxygen (left) and corresponding Stern-Volmer plot (right) for PDMS-PCL fibers.

Sensitivity to gaseous phase oxygen: Gaseous oxygen concentration was gradually increased (in 10% intervals) and the corresponding spectra of emission plotted in FIG. 9. The Ru(dpp)(Cl) in S1 core-shell fibers absorb visible light at 455 nm and emit red luminescence at 618 nm. The intensity of the emission peak of core-shell fibers was efficiently quenched as the oxygen concentration increased gradually from 0 to 100% as in FIG. 9A. No peak shift was observed when increased levels of oxygen were introduced into the environment. The saturated peak on the left originates from the blue LED light excitation. A similar spectral response is observed in FIG. 9C for sample S2 along with a higher degree of quenching and a red shift to 622 nm. Due to the higher probe concentration, the emission peaks of sample S2 exhibited less overlap with the light source peak. The same test of sample S3 generated significantly different spectral shapes and responses to gaseous oxygen (FIG. 9E). The emission peak for S3 is at 645 nm and is sharper compared to samples with Ru probe. The dynamic quenching process could be described by the Stern-Volmer equation.

Figure 9B:
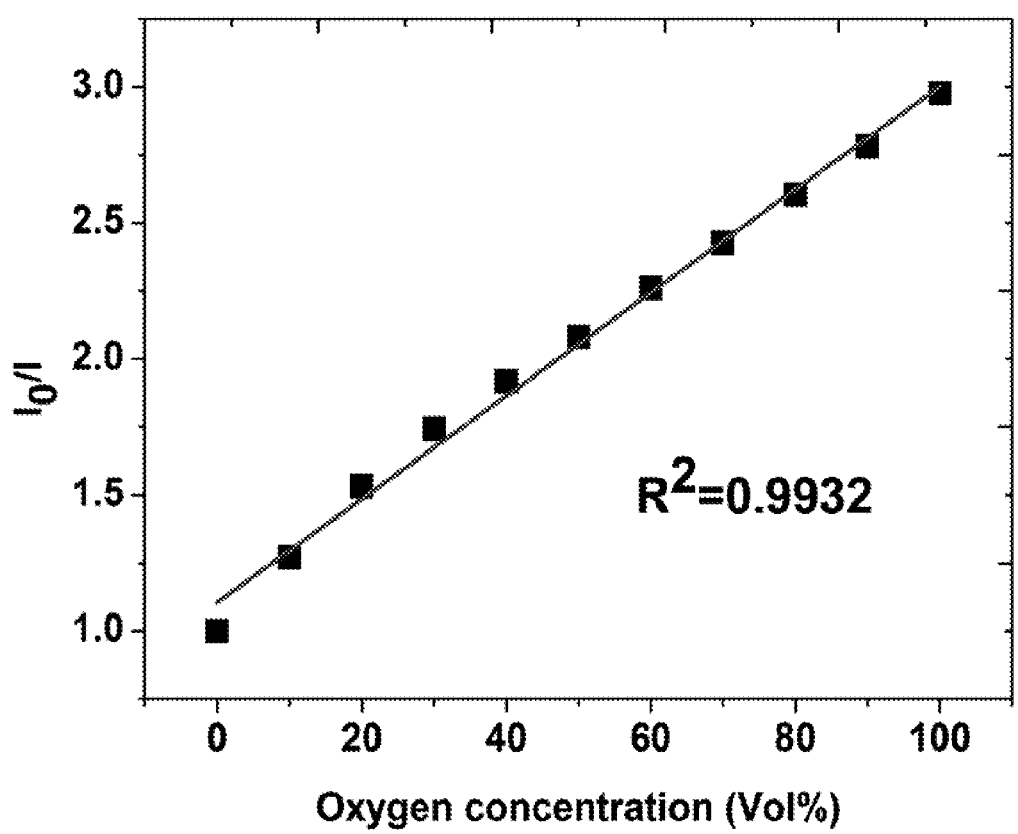
Figure 9C:
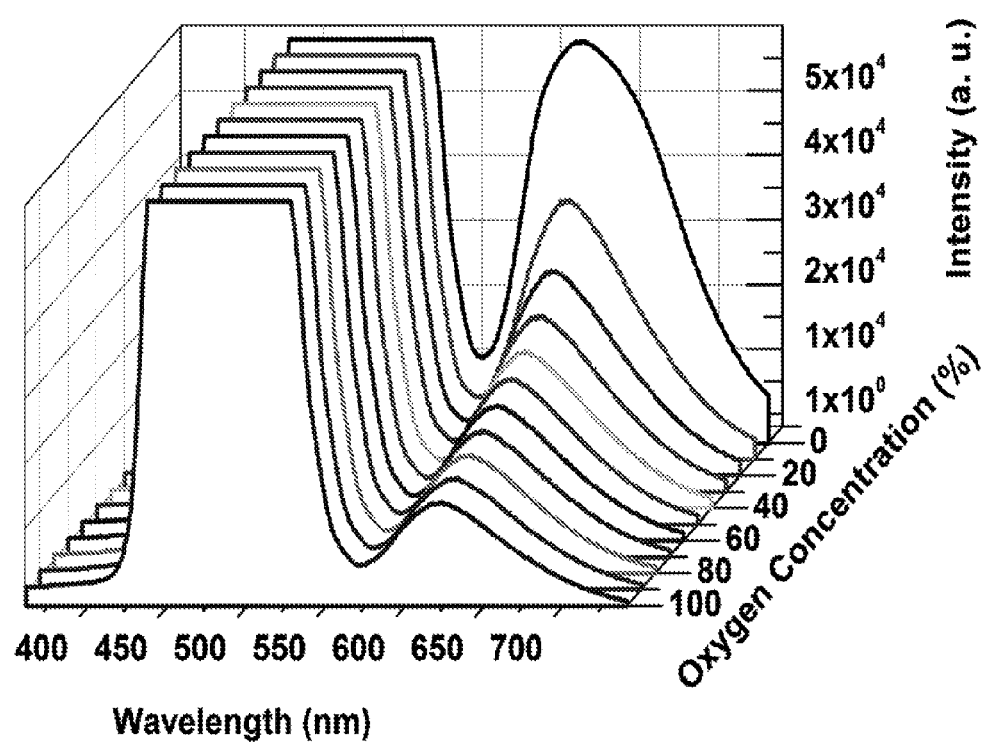
Figure 9D:
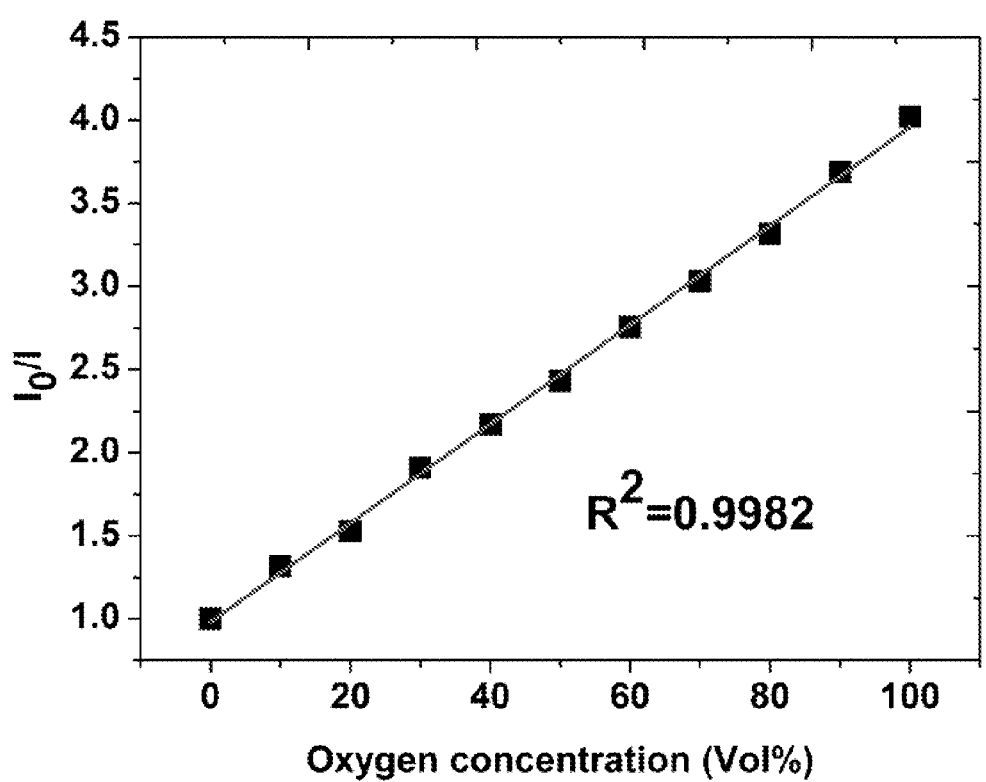
Figure 9E:
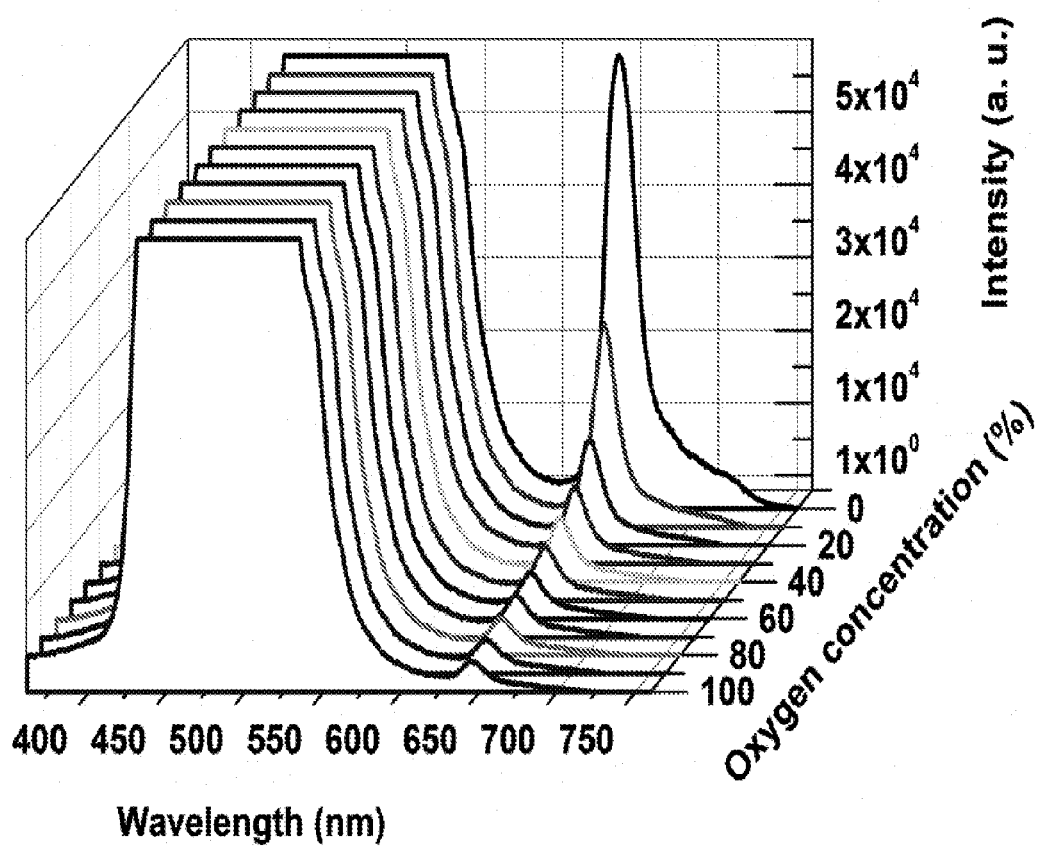
Figure 9F:
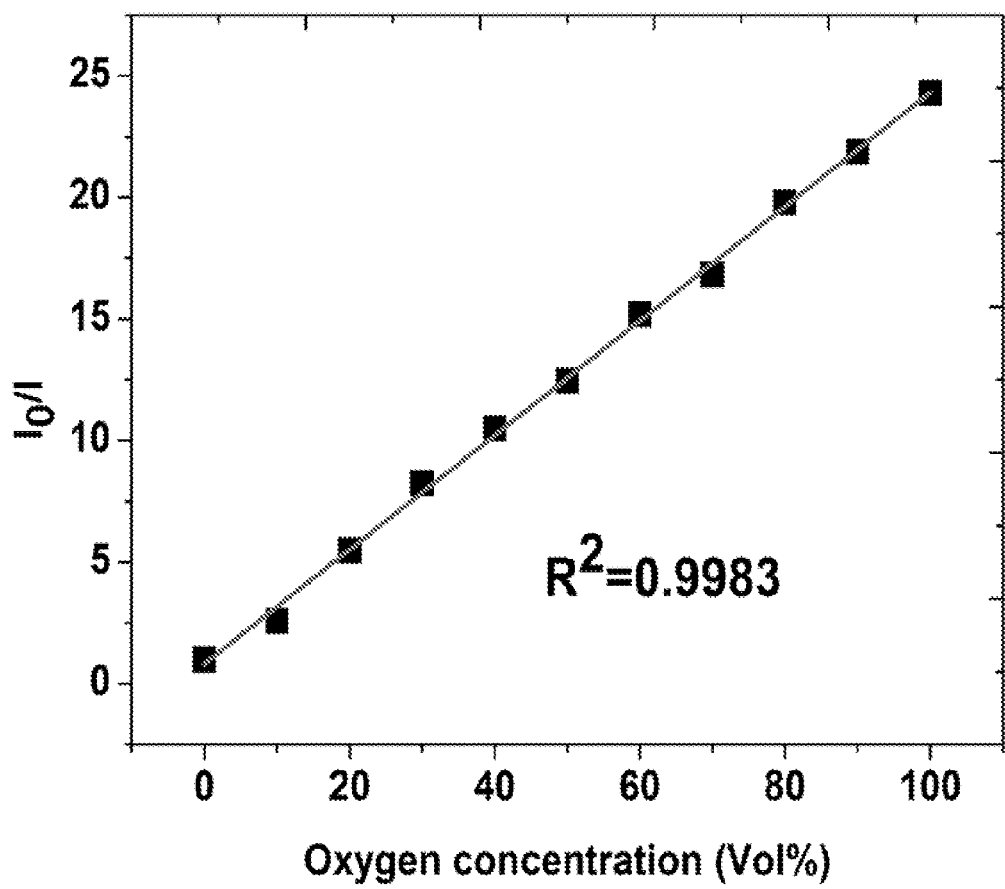

FIGS. 9B, 9D and 9F show the Stern-Volmer data of PDMS-PCL fibers S1-S3 by monitoring the intensity of emission peaks at various oxygen concentrations. Also included are their linear fits. A simple representation of the sensitivity of the sensors could be the intensity ratio of the sensors when exposed to an oxygen-free environment or pure oxygen $I_0/I_{100}$. For sample S1, the $I_0/I_{100}$ value is 2.97 and the coefficient ($R^2$) for the linear fitting is 0.9932. Both sensitivity and linear fitting are improved for S2 with $I_0/I_{100}$ of 4.10 and $R^2$ of 0.9982. For PtOEP probe containing S3 sample, a six-fold higher $I_0/I_{100}$ value of 24 is obtained, a significant improvement in sensitivity. The linear calibration fitting is also very good ($R^2$=0.9983).

Figure 10A:
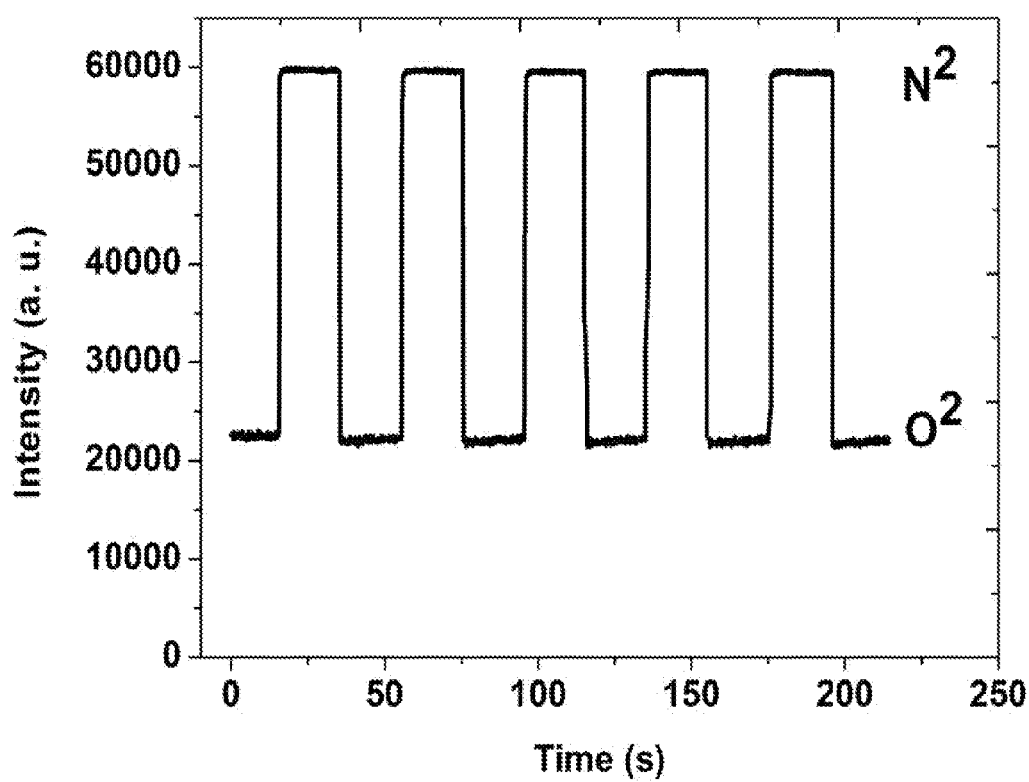
FIGS. 10A-10C are graphs illustrating the reversibility of PDMS-PCL sensors for S1 (FIG. 10A), S2 (FIG. 10B), and S3 (FIG. 10C) to alternating nitrogen and oxygen gas.
Figure 10B:
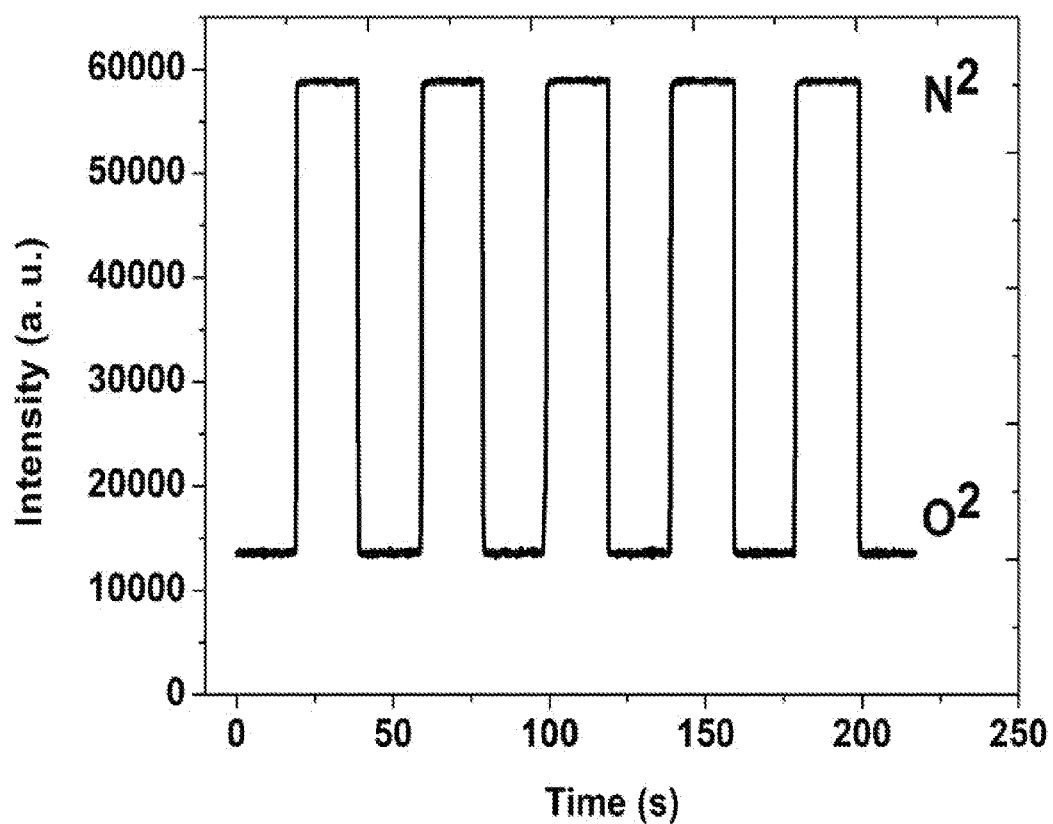
Figure 10C:
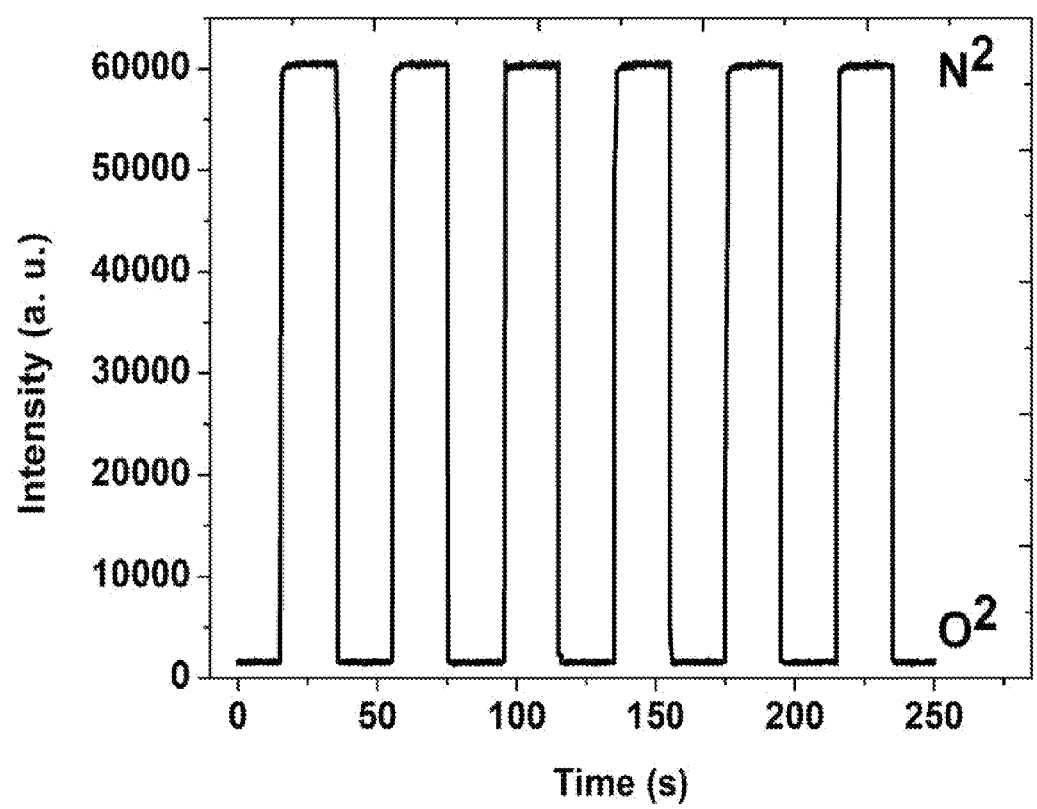

Reversibility, response time and recovery time to gaseous phase oxygen: When the sample was continuously monitored in rapidly alternated gaseous atmospheres, the intensity dropped and fully recovered when the environment was switched between pure nitrogen to oxygen as shown in FIG. 10. All three samples show good intensity reversibility and prompt response. S1 PDMS-PCL core-shell fibers showed 0.36±0.05 s response time and 0.72±0.27 s recovery time. Similar fast response and recovery were also observed for the two other samples. The response time was 0.28±0.08 s for S2 and its recovery time was 0.51±0.15 s. For sample S3, response and recovery time were 0.49±0.13 s and 0.70±0.15 s, respectively.

Figure 11A:
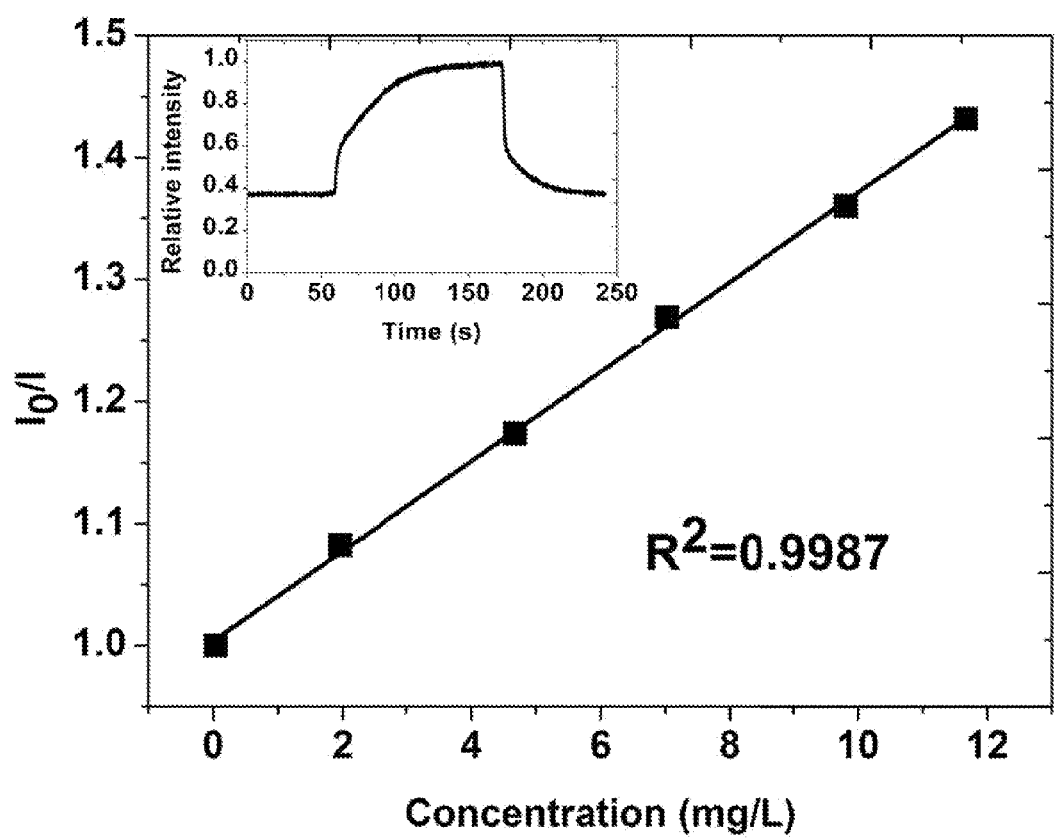
FIGS. 11A-11C are Stern-Volmer plots of PDMS-PCL sensor response to dissolved oxygen for S1 (FIG. 11A), S2 (FIG. 11B), and S3 (FIG. 11C). The figure insets report their continuous responses when water was consecutively saturated by oxygen/nitrogen/oxygen etc.
Figure 11B:
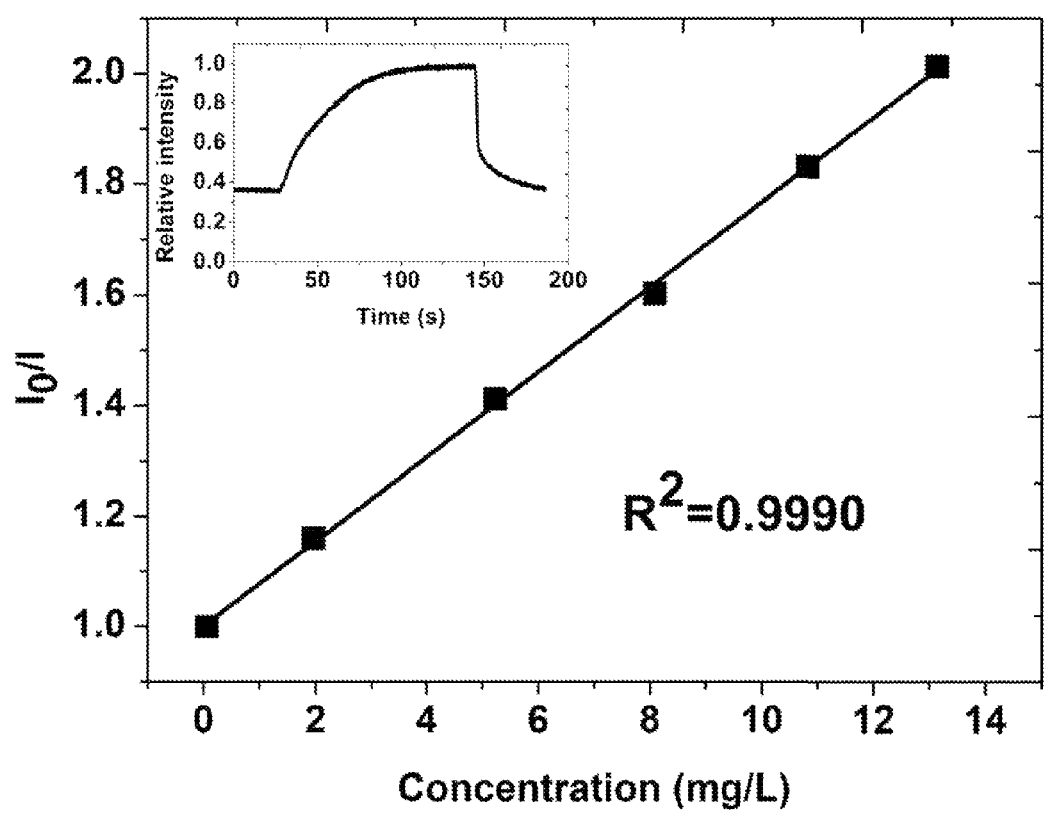
Figure 11C:
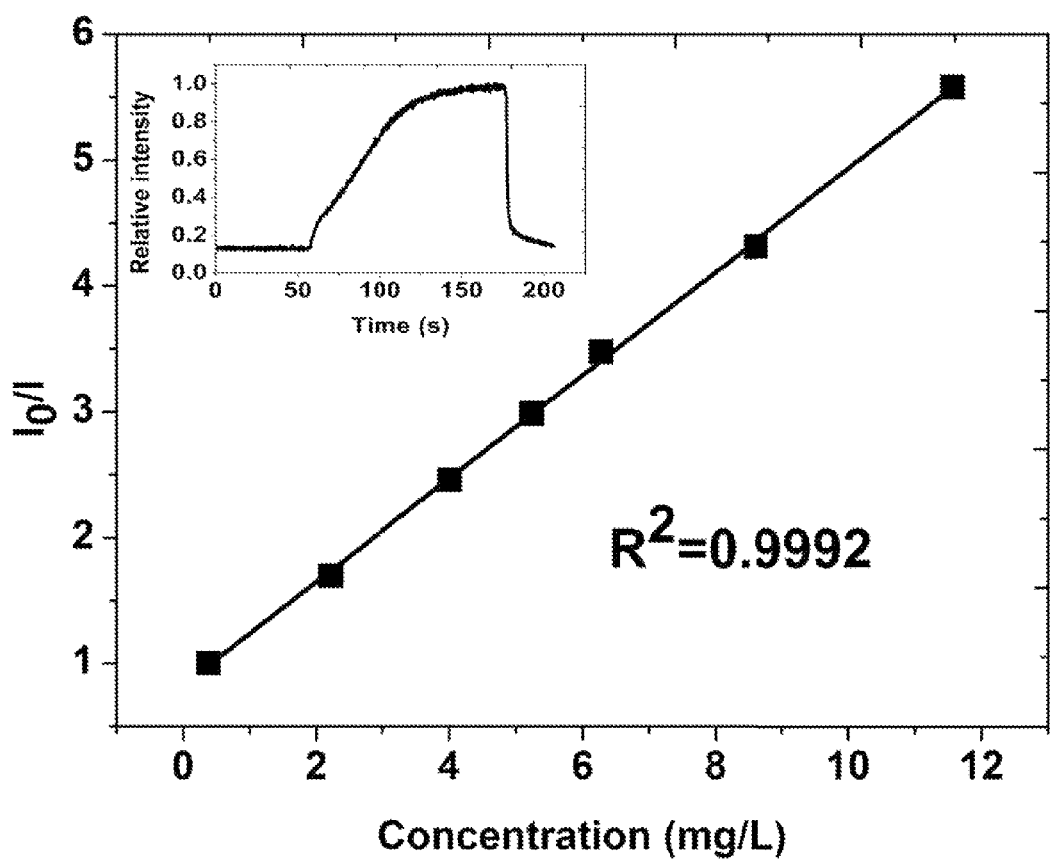

Sensing performance-dissolved oxygen: FIG. 11 shows the Stern-Volmer response of the core-shell fibers to dissolved oxygen. The oxygen concentration (independently measured in parallel using the commercial meter) was varied over a biologically-relevant range. The nanofiber sensors revealed excellent response to even very small variations in dissolved oxygen. Stern-Volmer constants ($K_{SV}$) for S1-S3 are 0.04, 0.08 and 0.41 (mg/L)$^{-1}$, respectively. Similar to the trends for gaseous oxygen, S3 showed significantly higher sensitivity than S1 and S2. The fitting coefficients are equivalently high for all three fibers: $R^2$(S1)=0.9987, $R^2$(S2)=0.9990 and $R^2$(S3)=0.9992. Intensity was then continuously monitored when alternating oxygen and nitrogen as shown in the insets of FIG. 11. The fibers showed reversible luminescence change in water but the response and recovery time were longer than the gas phase tests. The delay was apparently caused by the time required to saturate the solution with the appropriate gas. This is proven by the fact that the pattern of response/recovery could be altered significantly if the gas flow rate was varied.

Figure 12:
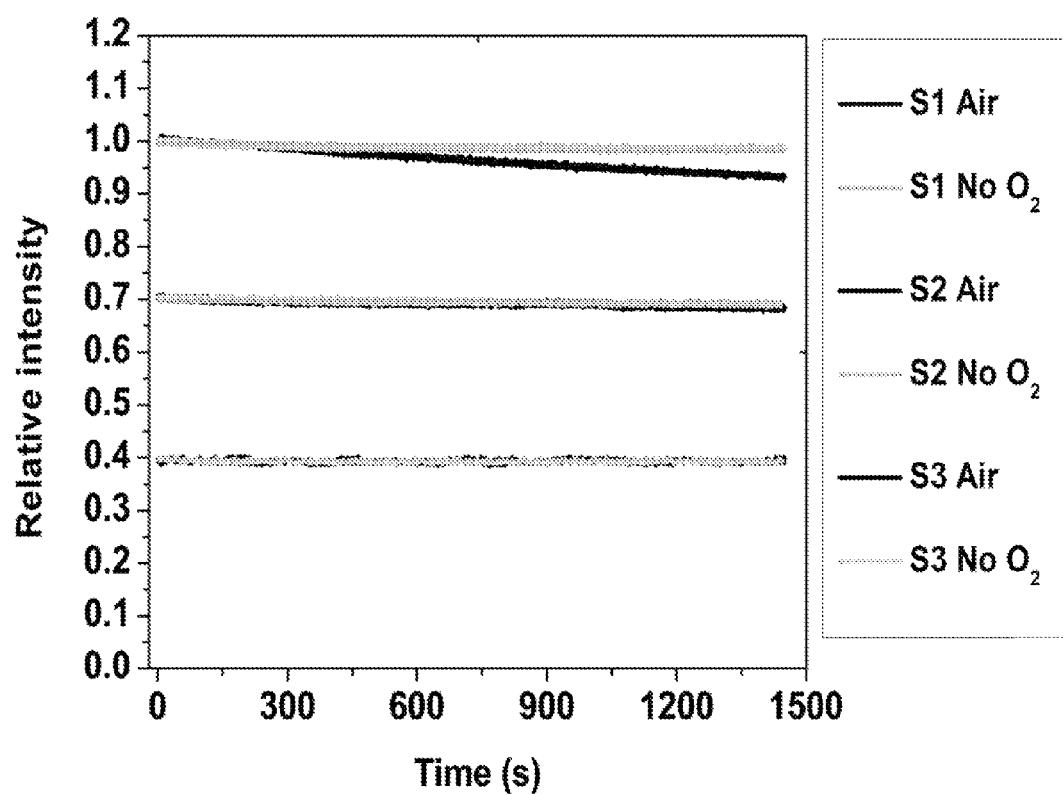
FIG. 12 is a graph illustrating the photostability tests for PDMS-PCL core-shell fibers in air saturated and oxygen-free water

Stability: The PDMS-PCL fibers were placed in water and were continuously illuminated by the blue LED light to record the signal change as function of time. To examine the effects of oxygen to photobleaching, tests were conducted in both oxygen-free and air-saturated water (FIG. 5, 'No $O_2$' vs. 'Air') for easy representation and comparison, data of all samples are shown in the same plot and the initial relative intensities are set to 1, 0.7 and 0.4 for S1-S3, respectively. As shown in FIG. 12, only sample S1 shows some noticeable intensity decay under continuous excitation. S1 in air-saturated water exhibited a faster rate of decrease (0.28% per min) than the same sample measured in oxygen-free water (0.06% per min). Less than 1% total intensity decay could be measured for S2 in both conditions after completion of the experiment. For sample S3, virtually no intensity decrease was detected following the light exposure.

Figure 13A:
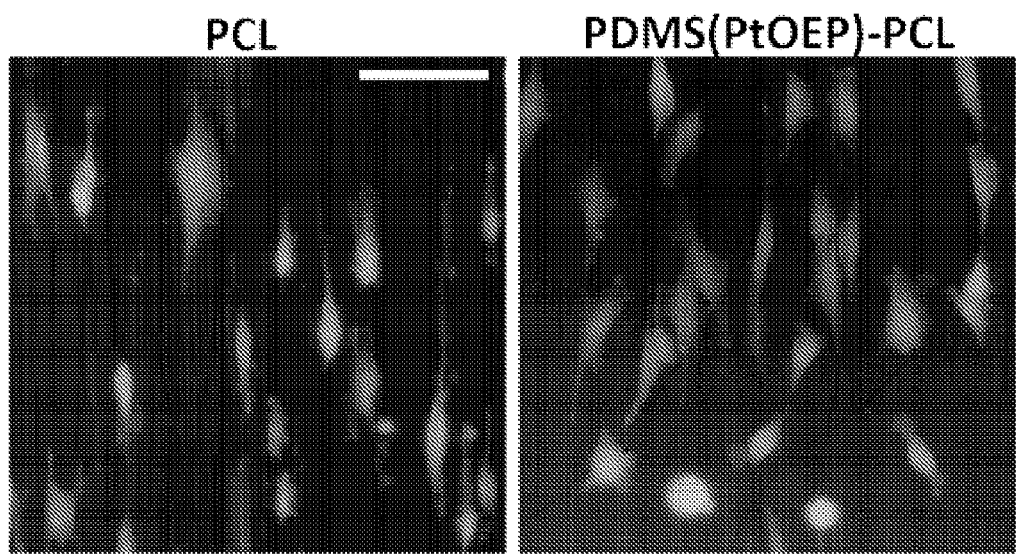
FIGS. 13A-13B are images showing the cell morphology and dispersion on PCL nanofibers versus PDMS(PtOEP)-PCL nanofibers.
Figure 13B:
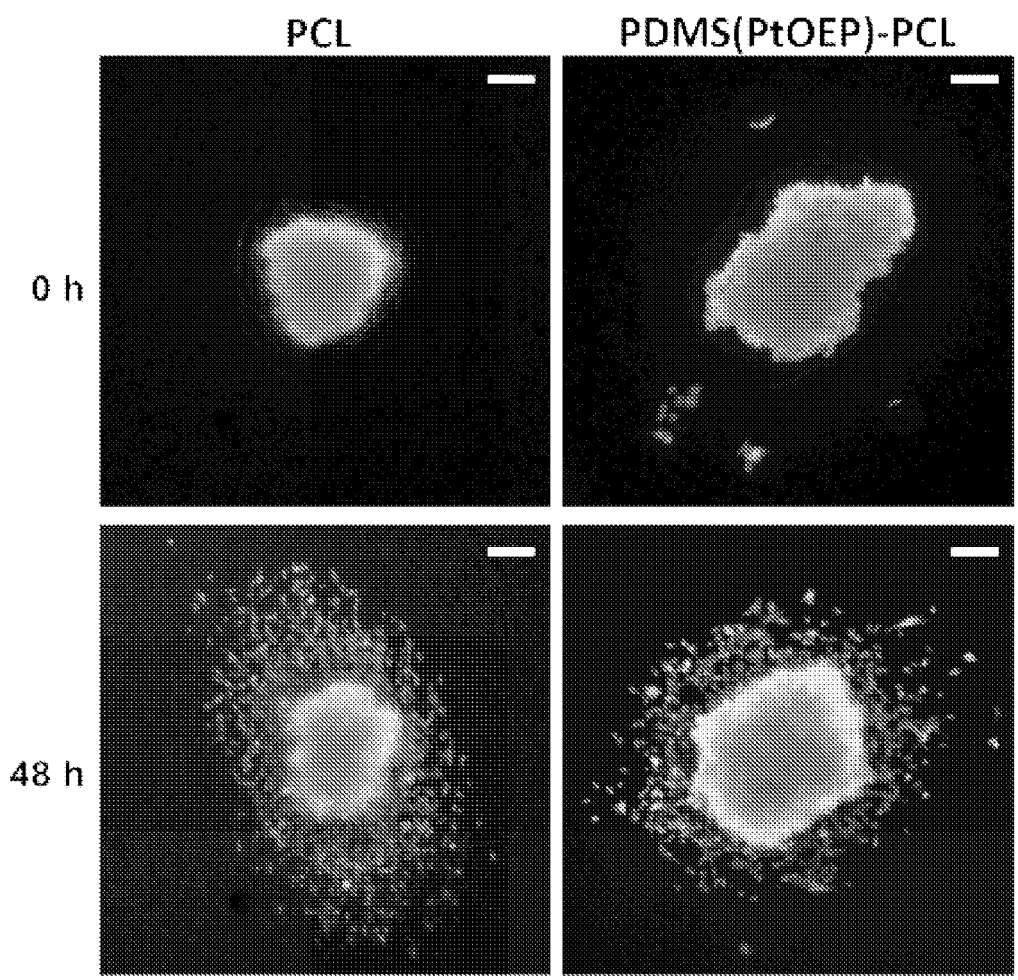
Figure 14A:
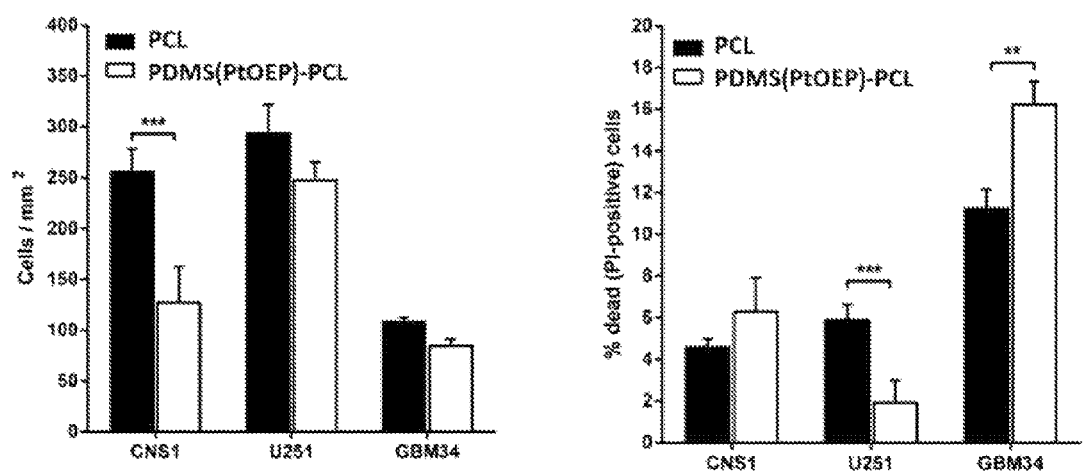
FIGS. 14A-14B are bar graphs showing cell viability and migration in PCL and PDMS(PtOEP)-PCL nanofibers.
Figure 14B:
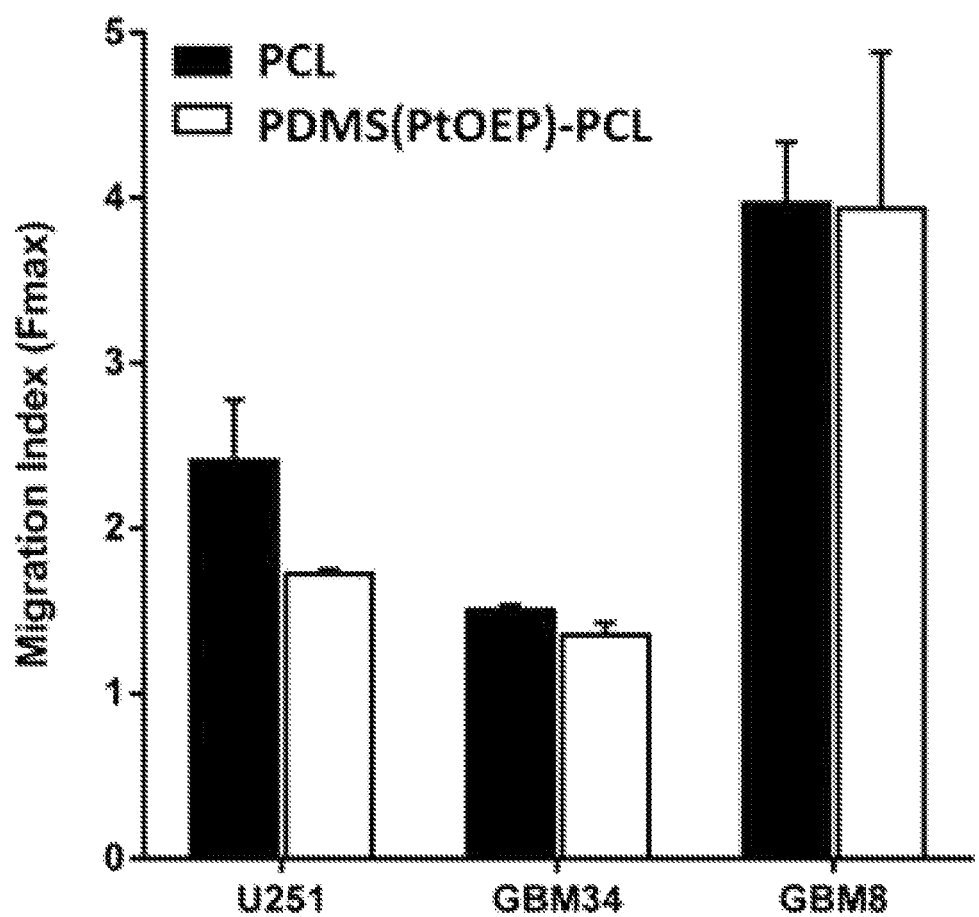

Oxygen-sensing nanofiber cytotoxicity: To investigate cytotoxicity potentially caused by the presence of the Pt porphyrin within the PDMS core of these nanofiber sensors, both electrospun PCL without any probe molecules and the Pt probe-containing PDMS(PtOEP)-PCL nanofiber sensors (S3) were investigated using adherent cultures of different glioblas-toma cell types, including highly-sensitive primary cultures of glioblastoma stem-like cells. Cell morphology on aligned versions of the different fiber compositions was essentially identical and there were no evident differences in cell stretching over the fibers (FIG. 13A). Cell dispersion was also undistinguishable between PCL and PDMS (PtOEP)-PCL fibers, indicating that cell adhesion and motility had not been affected by the Pt compound (FIG. 13B). Quantitative analysis of cell viability (FIGS. 14A and 14B) and cell migration indicated that number of adhered cells per mm$^2$, proportion of viable cells, and cell migration index, were largely identical between PtOEP-containing nanofibers and PCL nanofibers, with minor differences that did not follow a common trend for the different cells analyzed. Overall, the presence of the platinum porphyrin within the PDMS core did not lead to consistent, significant cytotoxicity.

Discussion

Electrospinning of PDMS-PCL fibers: Few reports of PDMS electrospinning exist and all involve relatively complex procedures. In this case, however, PDMS can be electrospun to form the unique core-shell structure in a single step due to the advantages conferred by containment within the PCL shell. When the falling fibers successfully reach the grounded collector, the PCL shell covering the uncured PDMS plays a role as it efficiently confines the relatively mobile liquid containing the uncured PDMS solution and prevents film formation. The cross-linking reactions (catalyzed either by the curing agent or by water) follow and morphologically stable PDMS-PCL core-shell fibers based optical oxygen sensors are created. Based on the SEM images, PDMS-PCL fibers show typical electrospun fiber morphology and dye loading has little influence on the structure of the core-shell fiber. Fiber diameters are generally in the range of 400-600 nm. The order of fiber diameter for the three samples is S2<S1<S3. Electrospun fiber diameter and morphology are dependent on various parameters such as polymer identity, solvent, solution concentration, applied voltage and flow rate. The cross-linking reaction for the two-part PDMS is initiated by the catalyst and occurs between PDMS base and curing agent. Although there is virtually no shrinkage during the reaction due to a lack of byproducts, the reaction rate is apparently decreased when the ruthenium complex is present. The evidence for this is the fact that attempts to use the same PDMS solution for S1 with high probe concentration to generate solid films instead maintained their liquid state for several days after addition of the curing agent, an observation we attribute to an unfavorable chemical interaction between the dye and the curing agent.

The curing of one-part moisture cure PDMS for S2 and S3 requires only the participation of ambient moisture and is virtually insensitive to the presence of the oxygen probe molecules. The porous nature of the fibers combined with the very high surface area assists in the curing process catalyzed by the ready availability of ambient moisture.

While improved curing allows for increased probe concentrations, another important factor concerns the solubility of the probe in the matrix. Ru(dpp)(Cl) is a chloride salt and is hydrophilic in nature and therefore solubility is limited in the hydrophobic PDMS matrix. Other work has shown that the hydrophilicity of the salt is mostly determined by the counterion and thus the Ru(dpp)complex can become lipophilic if the chloride is replaced by a hydrophobic counterion such as tetraphenylborate (PB). In addition, the luminescence properties of the Ru complex with the hydrophobic counterion are virtually the same as its chloride salt-based counterpart and the sensing ability should not be influenced by modification of the ion pair. As a result, the high Ru(dpp)(PB) probe doping in S2 does not cause any noticeable agglomeration while increasing the emission signal of the fibers. Similarly, high PtOEP could also be embedded in S3 without causing any problem either for curing or for probe dispersion.

Luminescence of PDMS-PCL fibers: The luminescence of the Ru based complexes used in S1 and S2 involves promotion of an electron from the metal d orbitals to a ligand antibonding orbital, a process known as metal-to-ligand charge transfer (MLCT). After excitation, a triplet state could be reached from an excited singlet state by intersystem crossing having a rate coefficient close to unity. Thus, fluorescence from the excited singlet to the ground state is rarely observed and emissions are mainly phosphorescent and have relatively long life-times. Quenching of the phosphorescence via dynamic collision with oxygen molecules is then used to report environmental oxygen concentrations. As shown in FIG. 9, the emission peaks of S1 and S2 have a similar shape due to the incorporation of the same Ru complex cation responsible for the luminescence. The hydrophobic counterion tetraphenylboron allows for higher dye concentrations in PDMS for S2 and also shifts the emission peak to 622 nm compared to low probe concentration S1 sample's 618 nm peak. The oxygen sensitive probe PtOEP used in S3 has a lifetime of 75 µs (versus 6.4 µs for the Ru probe), larger Stokes shift and greater photostability. The absorption in the visible range originates from the $\pi$ to $\pi^*$ transition and the intersystem crossing to the triplet state enabling long-lived phosphorescence emission. The emission peak (645 nm) is well separated from the excitation wavelength (535 nm). This efficiently eliminates the influence of the excitation source. The hydrophobic nature of PtOEP also allows its higher loading within the PDMS matrix at the same concentrations as in the S2 sample.

Sensitivity to gaseous oxygen: Since the triplet to ground state transition (emission of phos-phorescence) is spin forbidden, the lifetime of phosphorescence is relatively long and is therefore susceptible to environmental deactivation (such as quenching) due to molecular oxygen. Sensitivity can be directly observed from the spectral response when the samples are exposed to environments gradually varying from 0 to 100% oxygen. Due to the improved chemical accommodation of hydrophobic Ru(dpp)(PB), sample S2 shows higher $I_0/I_{100}$ (4.10) compared to 2.97 $I_0/I_{100}$ value obtained from S1 sample containing the hydrophilic chloride salt of the same complex. PtOEP has even longer lifetimes and therefore generally better sensitivity and much lower detection limits. The observed $I_0/I_{100}$ of 24 for sample S3 constitutes a dramatic improvement relative to Ru based oxygen detection in the same core-shell fibers. The sensing performance of oxygen sensors depends on probe properties, matrix identity, probe-matrix interactions and the overall sensor form. The sensitivity of other non-fibrous sensor systems spans a large range in which $I_0/I_{100}$ values vary from 1.1 to several hundred. The fibers incorporating Ru probes in the current study show sensitivity comparable to the physically embedded form of the same probe in either mesoporous silica or polystyrene film. The sensitivity of PDMS-PCL fibers is increased compared to previously studied fibers composed of PCL alone. On the other hand, the sensitivity ($I_0/I_{100}$ value) of PtOEP in the nanofibers appears to be higher than that observed when the same probe is dispersed in polystyrene (4) and polyethylmethacrylate films but is lower than that observed in sol-gel produced carriers. A major advantage of nanofibers over widely used films is that all three PDMS-PCL fibers exhibited excellent linearity over the entire range of oxygen concentrations (0-100%). In contrast, a downward Stern-Volmer curvature is observed in a variety of literature-based systems especially those based on silicone. Accordingly, to produce a linear calibration curve, a multi-site Stern-Volmer model is often used. In such cases, the probe is believed to present both its molecularly uniform state and an aggregated form each having distinct quenching constants. The ratio of these two forms will vary depending on the compatibility between the host polymer and the sensing probe. The slightly lower fitting coefficient of S1 compared to S2 is attributed to the lower solubility of the hydrophilic version of the Ru complex in PDMS. An excellent linearity for Pt dye in the PDMS system indicates an excellent compatibility as observed by other studies. A single quenching constant Ksv can only be obtained when the sensing probe molecules are evenly dispersed in the matrix materials and have the equivalent opportunity for oxygen access. The excellent linear behavior of the PDMS-PCL fibers occurs because the speed of the electrospinning and evaporation process probably locks the solvated probe distribution in place. The curing reaction rate for moisture cure PDMS is also accelerated due to the small fiber dimensions that provide constant, easy moisture access. This increased curing rate is relevant because in other studies that involve a longer curing time necessary for film formation (especially at elevated temperatures), probe molecules have been observed to migrate and aggregate to form regions having lower/different sensitivities.

Reversibility, response time and recovery time in gas phase oxygen: PDMS-PCL core-shell fibers show short response times (less than 0.5 s) owing to the high surface-area-to-volume ratio that significantly reduces the barrier for oxygen diffusion to the molecular probe. In contrast, typical response times of film-based sensors varies from less than 1 s to tens of seconds depending upon the matrix. Gas exchange for sensing films is limited to the 2D external surface and increasing film thickness (to enhance signal strength) increases diffusion depth and worsens the response time. However, the response time of PDMS-PCL core-shell fibers does not change as mat thickness increases due to the inherently high porosity of electrospun fibers. Rapid response and recovery also attests to the oxygen permeability of PDMS and its suitability for inclusion as the core. This is additionally demonstrated by comparison to similar fiber-based systems that utilized Cu-or Eu-based fluorophores but display 4-10 times longer response times. The room temperature oxygen diffusivity in PDMS is $4.1 \times 10^5$ cm$^2$/s, almost twice the diffusivity of oxygen in water ($2.1 \times 10^5$ cm$^2$/s) under the same conditions. When used as sensor matrix in water, PDMS therefore provides relatively little barrier to oxygen diffusion to the probe and allows real-time reporting of oxygen levels. The recovery time is longer than the response time likely due to the fact that $N^2$ gas permeability and diffusivity in polymers is less than that of $O_2$. The response time of the PDMS-PCL sensors is also related to the fiber diameter due to the observation that the order of response times for the three samples is the same as that of the fiber diameter (S2<S1<S3).

Sensor performance to dissolved oxygen: The dissolved oxygen concentration range explored (FIG. 11) covers a variety of circumstances that cells may encounter in vivo. Although 21% oxygen enters the lungs, dissolved oxygen in the body averages only 3-5%, depending on the tissue. The fibers show high quenching constant $K_{SV}$ and excellent linear fit, which enables precise quantitative determination of oxygen concentration in the range of interest without the need for complex calibration equations. Due to the hydrophobic nature of PDMS, the embedded probe molecules are shielded from ionic species by the permeation selective nature of the surrounding matrix. Dissolved oxygen molecules must first escape from aqueous solution and penetrate the polymer matrix to reach the probe. The partial pressure of gaseous oxygen is in equilibrium with the dissolved oxygen and related by Henry's Law. Therefore, the order of the three samples in terms of sensitivity is the same as the gas phase tests (S3>>S2>S1) and the excellent Stern-Volmer data fittings still hold for all dissolved oxygen measurements. The examination of real time PDMS-PCL response is critical for the sensor's future application so the same reversibility test was conducted in deionized water by again alternating nitrogen and oxygen exposure. While the environment itself took time to become saturated with $N_2/O_2$, the full sensor response only required about 10 s (FIG. 11). Considering the very fast response togas phase oxygen (shown in FIG. 10), we can assume that ~95% of the time needed for the sensor to fully respond/recover is due mainly to the slowness of oxygen removal/dissolution and not the sensor itself.

Stability: FIG. 12 shows that (a) photobleaching rate is faster in the presence of oxygen for S1; (b) S2 PDMS-PCL fibers show slower decay rate even though they have higher probe concentration than S1; (c) S3 is the most photostable sensor in the currently studied core-shell fiber systems. The rate of photobleaching generally increases with increasing oxygen concentration due to the generation of reactive singlet oxygen, a dynamic quenching by-product believed to be responsible for the photooxidation of probe molecules. During the consumption of oxygen by adherent cells, the real photobleaching rate of the sensors applied in cell culture should fall somewhere between the 'Air' and 'No $O_2$' curves in FIG. 12. When oxygen-sensitive probes are dissolved in polymer matrix materials, the probe-probe and probe-host inter-actions not only determine the final sensing performance of the sensor but also the stability of the luminescence emission. It has been observed that when incorporated probe concentrations reach a critical value, the probes suffer from concentration quenching and triplet state annihilation. This could explain the different photobleaching behaviors observed for S1 and S2. Although the probe concentration in S1 is lower than S2, poor solubility of the probe in PDMS matrix could cause local probe aggregation to accelerate photobleaching. S3 shows the best resistance to photobleaching among all three samples due both to the higher photostability of PtOEP and likely—excellent dispersion. It should be noted that for general applications of these sensors in cell culture, the total light exposure time needed to acquire oxygen concentrations will be far less than the duration of the tests in this study. In addition, these probes remain stable and active in the core-shell fibers during sensor fabrication, testing, storage and cell culture. The highly hydrophobic PDMS matrix and the protective PCL shell appear to prevent water penetration that might interfere with the performance of the probes. Cell viability and the lack of cytotoxicity also demonstrate the utility of incorporating probes inside these fibers.

Biocompatibility: As shown in FIG. 13, glioma cell morphology, association with the different types of fibers, and pattern of cell dispersion were essentially identical, with only slight visual differences. Since cell viability was not consistently affected (FIG. 14) it was hypothesize that these small differences likely reflect differences in cell response to nanofiber modulus rather than effects of the nanofiber chemistry on the cells. It has been shown that the presence of a PDMS 'core' inside of a PCL 'shell' results in a higher modul-us that can affect glioma cell adhesion and migration. This could explain the slightly more rounded morphology of glioma cells on PDMS-PCL and reduced cell adhesion of the CNS1 line (FIG. 14). These differences, however, had no effect on migratory behavior, as indicated by the identical migration indexes of all cells analyzed on different fiber compositions. Cell viability, measured as the proportion of PI-positive to total cells showed an inconsistent pattern with one cell line unaffected (CNS1), another line showing reduced cell death in PDMS-PCL fibers (U251), and the third cell culture showing increased death (GBM 34). Again, these differences are likely a result of the differential response of the cells following adhesion to fibers of different modulus. It should be noted that cell death for established cell lines was consistently low (below 8% of total cells) while primary glioblastoma stem-like cells were considerably more affected, as expected. This strongly suggests a cell-specific response to the physical differences of the substrate rather than any consistent cytotoxicity due to the Pt porphyrin compound embedded in the fibers.

CONCLUSIONS

A new optical oxygen sensor is fabricated by the core-shell electrospinning of highly oxygen permeable polydimethylsiloxane within an envelope of biocompatible polycaprolactone. Fluorescent oxygen sensitive probes, tris(4,7-diphenyl-1,10-phenanthroline)ruthenium(II) and platinum octaethylporphyrin, are incorporated into this PDMS core. Fiber sensitivity can be adjusted depending on the chemistry, dispersion and inherent photon yield of the probes themselves. All sensors show rapid responses less than 0.5 s due to the porous nature of electrospun fibers coupled with the relatively trivial diffusion barrier presented by the PDMS matrix. Linear calibration is achieved for both gaseous and dissolved oxygen over biologically relevant ranges. Sensing probes embedded in the fiber were shown to be stable throughout all tests and assessments. Glioma cell viability and migration experiments on these fibers show negligible biological effects of the sensing probes on the cells. These unique fiber-based sensors could be readily integrated to standard cell culture plates or bioreactors to provide critical oxy-gen information for both cancer cell research and engineered tissue growth.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A core shell nanofiber comprising (a) a core comprising a first polymer and an oxygen sensor dispersed therein; and (b) a shell comprising a second polymer disposed coaxially around the core,
    wherein the nanofiber has a diameter of about 1000 nm or less.

2. The nanofiber of claim 1, wherein the first polymer is oxygen permeable.

3. The nanofiber of claim 2, wherein the first polymer has an oxygen diffusivity greater than water.

4. The nanofiber of claim 1, wherein the nanofiber is substantially resistant to photobleaching and heat.

5. The nanofiber of claim 1, wherein the second polymer is biocompatible.

6. The nanofiber of claim 1, wherein the first polymer is selected from the group consisting of polyethersulfone and polydimethylsiloxane.

7. The nanofiber of claim 1, wherein the second polymer is polycaprolactone.

8. The nanofiber of claim 1, wherein the oxygen sensor comprises a luminophore.

9. The nanofiber of claim 8, wherein the luminophore exhibits an emission peak of from about 570 nm to about 670 nm.

10. The nanofiber of claim 8, wherein the oxygen sensor is selected from the group consisting of tris (4,7-diphenyl-1,10-phenanthroliine) ruthenium (II) dichloride, (4,7-diphenyl-1,10-phenanthroliine) ruthenium (II) tetraphenylboron, platinum (II) octaethylporphinedialkylcarbocyanine, and diocadecylcycloxacarbocyanine.

11. The nanofiber of claim 1, wherein the nanofiber has a diameter of from about 400 nm to about 600 nm.

12. The nanofiber of claim 1, wherein the the nanofiber has a diameter of from about 401 nm to about 960 nm.

13. The nanofiber of claim 1, wherein the oxygen sensor and the first polymer are present in the core at weight ratio of the oxygen sensor to the first polymer of from about 1:1000 to about 1:200.

14. A method for measuring oxygen content in a sample, comprising
    (a) contacting the sample with a nanofiber of claim 1; and
    (b) evaluating the optical properties of the oxygen sensor to determine the oxygen content of the sample.

15. The method of claim 14, wherein the optical property of the oxygen sensor is luminescence.

16. The method of claim 15, wherein the luminescence is fluorescence.

17. The method of claim 14, wherein the change in optical property includes a change in intensity of an emission signal.

18. The method of claim 14, wherein the sample is an aqueous solution.

19. The method of claim 14, wherein the sample comprises a biological sample.

20. The method of claim 19, wherein the biological sample comprises cells.

21. The method of claim 14, wherein the nanofiber monitors the oxygen content level of the sample in real time.

22. The method of claim 14, wherein the nanofiber exhibits a response time of less than about 10 seconds to a change in oxygen content.

23. The method of claim 22, wherein the response time is less than about 0.5 seconds.

* * * * *